(12) United States Patent
Jiang et al.

(10) Patent No.: US 11,059,792 B2
(45) Date of Patent: Jul. 13, 2021

(54) IMIDAZOLYL TRICYCLIC ENONES AS ANTIOXIDANT INFLAMMATION MODULATORS

(71) Applicant: REATA PHARMACEUTICALS, INC., Irving, TX (US)

(72) Inventors: Xin Jiang, Coppell, TX (US); Bradley William Caprathe, Livonia, MI (US); Chitase Lee, Ann Arbor, MI (US); Gary Bolton, Ann Arbor, MI (US); Christopher F. Bender, Garland, TX (US); Melean Visnick, Irving, TX (US)

(73) Assignee: REATA PHARMACEUTICALS, INC., Irving, TX (US)

( * ) Notice: Subject to any disclaimer, the term of this patent is extended or adjusted under 35 U.S.C. 154(b) by 387 days.

(21) Appl. No.: 15/548,909

(22) PCT Filed: Feb. 12, 2016

(86) PCT No.: PCT/US2016/017769
§ 371 (c)(1),
(2) Date: Aug. 4, 2017

(87) PCT Pub. No.: WO2016/130927
PCT Pub. Date: Aug. 18, 2016

(65) Prior Publication Data
US 2018/0127380 A1     May 10, 2018

Related U.S. Application Data

(60) Provisional application No. 62/115,247, filed on Feb. 12, 2015.

(51) Int. Cl.
| | |
|---|---|
| *C07D 235/08* | (2006.01) |
| *A61P 29/00* | (2006.01) |
| *C07D 235/02* | (2006.01) |
| *C07D 235/10* | (2006.01) |
| *C07D 235/12* | (2006.01) |
| *C07D 401/04* | (2006.01) |
| *C07D 403/04* | (2006.01) |
| *C07D 403/10* | (2006.01) |
| *C07D 403/14* | (2006.01) |
| *C07C 235/02* | (2006.01) |

(52) U.S. Cl.
CPC ............ *C07D 235/08* (2013.01); *A61P 29/00* (2018.01); *C07C 235/02* (2013.01); *C07D 235/10* (2013.01); *C07D 235/12* (2013.01); *C07D 401/04* (2013.01); *C07D 403/04* (2013.01); *C07D 403/10* (2013.01); *C07D 403/14* (2013.01)

(58) Field of Classification Search
CPC .. C07D 235/08; C07D 235/02; C07D 235/10; C07D 235/12; C07D 401/04; C07D 403/04; C07D 403/10; C07D 403/14; A61P 29/00
See application file for complete search history.

(56) References Cited

U.S. PATENT DOCUMENTS

| | | | |
|---|---|---|---|
| 6,326,507 B1 | 12/2001 | Gribble et al. |
| 6,552,075 B2 | 4/2003 | Gribble et al. |
| 6,974,801 B2 | 12/2005 | Honda et al. |
| 7,176,237 B2 | 2/2007 | Honda et al. |
| 7,288,568 B2 | 10/2007 | Gribble et al. |
| 7,435,755 B2 | 10/2008 | Konopleva et al. |
| 7,678,830 B2 | 3/2010 | Honda et al. |
| 7,714,012 B2 | 5/2010 | Honda et al. |
| 7,795,305 B2 | 9/2010 | Konopleva et al. |
| 7,863,327 B2 | 1/2011 | Gribble et al. |
| 7,915,402 B2 | 3/2011 | Anderson et al. |
| 7,943,778 B2 | 5/2011 | Jiang et al. |

(Continued)

FOREIGN PATENT DOCUMENTS

| | | |
|---|---|---|
| WO | WO 1999/065478 | 12/1999 |
| WO | WO 2002/047611 | 6/2002 |

(Continued)

OTHER PUBLICATIONS

Anderson 'The Process of Structure-Based Drug Design' Chemistry and Biology, vol. 10, 787-797, 2003.*

(Continued)

*Primary Examiner* — Jared Barsky
(74) *Attorney, Agent, or Firm* — Parker Highlander PLLC

(57) ABSTRACT

Disclosed herein are compounds of the formula: (I), wherein the variables are defined herein. Also provided are pharmaceutical compositions thereof. In some aspects, the compounds and compositions provided herein may be used as antioxidant inflammation modulators. In some aspects, the present disclosure provides methods wherein the compounds and composition described herein are used for the treatment of diseases and disorders associated with inflammation and cancer.

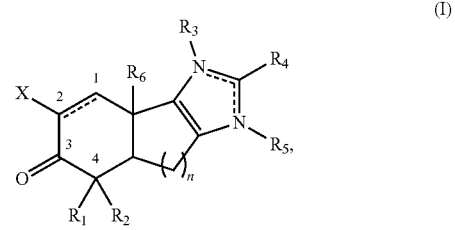

(I)

9 Claims, No Drawings

(56) References Cited

U.S. PATENT DOCUMENTS

| | | |
|---|---|---|
| 8,034,955 B2 | 10/2011 | Gribble et al. |
| 8,067,394 B2 | 11/2011 | Honda et al. |
| 8,067,465 B2 | 11/2011 | Honda et al. |
| 8,071,632 B2 | 12/2011 | Jiang et al. |
| 8,088,824 B2 | 1/2012 | Walling et al. |
| 8,124,656 B2 | 2/2012 | Anderson et al. |
| 8,124,799 B2 | 2/2012 | Anderson et al. |
| 8,129,429 B2 | 3/2012 | Sporn et al. |
| 8,258,329 B2 | 9/2012 | Anderson et al. |
| 8,299,046 B2 | 10/2012 | Sporn et al. |
| 8,309,601 B2 | 11/2012 | Walling et al. |
| 8,314,137 B2 | 11/2012 | Honda et al. |
| 8,338,618 B2 | 12/2012 | Jiang et al. |
| 8,394,967 B2 | 3/2013 | Jiang et al. |
| 8,440,820 B2 | 5/2013 | Anderson et al. |
| 8,440,854 B2 | 5/2013 | Anderson et al. |
| 8,455,544 B2 | 6/2013 | Sporn et al. |
| 8,513,436 B2 | 8/2013 | Anderson et al. |
| 8,586,775 B2 | 11/2013 | Gribble et al. |
| RE45,288 E | 12/2014 | Anderson et al. |
| 8,921,340 B2 | 12/2014 | Sporn et al. |
| RE45,325 E | 1/2015 | Anderson et al. |
| 8,993,640 B2 | 3/2015 | Anderson et al. |
| 9,000,188 B2 | 4/2015 | Honda et al. |
| 9,090,574 B2 | 7/2015 | Anderson et al. |
| 9,102,681 B2 | 8/2015 | Anderson et al. |
| 9,174,941 B2 | 11/2015 | Anderson et al. |
| 9,233,998 B2 | 1/2016 | Anderson et al. |
| 9,249,089 B2 | 2/2016 | Jiang et al. |
| 9,278,912 B2 | 3/2016 | Jiang et al. |
| 9,290,536 B2 | 3/2016 | Anderson et al. |
| 9,464,082 B2 | 10/2016 | Donner et al. |
| 9,796,668 B2 | 10/2017 | Anderson et al. |
| 9,884,809 B2 | 2/2018 | Anderson et al. |
| 2002/0042535 A1 | 4/2002 | Gribble et al. |
| 2003/0119732 A1 | 1/2003 | Konopleva et al. |
| 2003/0232786 A1 | 12/2003 | Honda et al. |
| 2003/0236303 A1 | 12/2003 | Gribble et al. |
| 2004/0002463 A1 | 1/2004 | Honda et al. |
| 2005/0288363 A1 | 12/2005 | Gribble et al. |
| 2007/0155742 A1 | 7/2007 | Honda et al. |
| 2008/0220057 A1 | 9/2008 | Gribble et al. |
| 2008/0233195 A1 | 9/2008 | Sporn et al. |
| 2008/0261985 A1 | 10/2008 | Honda et al. |
| 2009/0048204 A1 | 2/2009 | Walling et al. |
| 2009/0048205 A1 | 2/2009 | Meyer et al. |
| 2009/0060873 A1 | 3/2009 | Sporn et al. |
| 2009/0093447 A1 | 4/2009 | Konopleva et al. |
| 2009/0326063 A1 | 12/2009 | Sporn et al. |
| 2010/0041904 A1 | 2/2010 | Jiang et al. |
| 2010/0048887 A1 | 2/2010 | Anderson et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0281955 A1 | 11/2011 | Meyer et al. |
| 2012/0071684 A1 | 3/2012 | Walling et al. |
| 2012/0101149 A1 | 4/2012 | Honda et al. |
| 2012/0196880 A1 | 8/2012 | Anderson et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0252776 A1 | 10/2012 | Anderson et al. |
| 2012/0283450 A1 | 11/2012 | Anderson et al. |
| 2013/0089526 A1 | 4/2013 | Sporn et al. |
| 2013/0122053 A1 | 5/2013 | Sporn et al. |
| 2013/0237721 A1 | 9/2013 | Gribble et al. |
| 2013/0274480 A1 | 10/2013 | Honda et al. |
| 2013/0317007 A1 | 11/2013 | Anderson et al. |
| 2013/0324599 A1 | 12/2013 | Anderson et al. |
| 2013/0345276 A1 | 12/2013 | Sporn et al. |
| 2014/0051739 A1 | 2/2014 | Anderson et al. |
| 2014/0066408 A1 | 3/2014 | Jiang et al. |
| 2014/0088163 A1 | 3/2014 | Jiang et al. |
| 2014/0088188 A1 | 3/2014 | Jiang et al. |
| 2014/0100227 A1 | 4/2014 | Bender et al. |
| 2014/0179928 A1 | 6/2014 | Anderson et al. |
| 2014/0275618 A1 | 9/2014 | Gribble et al. |
| 2014/0377235 A1 | 12/2014 | Sporn et al. |
| 2015/0080465 A1 | 3/2015 | Chin et al. |
| 2015/0148384 A1 | 5/2015 | Anderson et al. |
| 2015/0152071 A1 | 6/2015 | Jiang et al. |
| 2015/0225397 A1 | 8/2015 | Donner et al. |
| 2015/0259377 A1 | 9/2015 | Anderson et al. |
| 2016/0130220 A1 | 5/2016 | Anderson et al. |
| 2016/0145200 A1 | 5/2016 | Anderson et al. |

FOREIGN PATENT DOCUMENTS

| | | |
|---|---|---|
| WO | WO 2003/059339 | 7/2003 |
| WO | WO 2004/064723 | 8/2004 |
| WO | WO 2006/089406 | 8/2006 |
| WO | WO 2008/064132 | 5/2008 |
| WO | WO 2008/064133 | 5/2008 |
| WO | WO 2008/136838 | 11/2008 |
| WO | WO 2009/023232 | 2/2009 |
| WO | WO 2009/023845 | 2/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2012/083306 | 6/2012 |
| WO | WO 2012/125488 | 9/2012 |
| WO | WO 2013/163344 | 10/2013 |
| WO | WO 2013/188818 | 12/2013 |
| WO | WO 2014/040056 | 3/2014 |
| WO | WO 2014/040060 | 3/2014 |
| WO | WO 2014/040073 | 3/2014 |
| WO | WO 2015/027206 | 2/2015 |
| WO | WO 2015/112792 | 7/2015 |

OTHER PUBLICATIONS

Theil 'Structure-aided drug design's next generation' Nature Biotechnology, 22(5), p. 513-519, 2004.*

Albini and Sporn, "Opinion: the tumour microenvironment as a target for chemoprevention," *Nature Reviews Cancer*, 7: 139-147, 2007.

Andresen and Margaretha, "Preparation of Dialkyl 2-Cyanocycloalk-2-en-1-ones," *J. Chem. Research* (S), 332, 1994.

Caron et al., "Versatile Strategy to access tricycles related to quassinoids and triterpenes," *Org. Letters*, 12(3) 508-511, 2010.

Chadalapaka, et al., "Structure-dependent inhibition of bladder and pancreatic cancer cell growth by 2-substituted glycyrrhetinic and ursolic acid derivatives," *Bioorganic & Medicinal Chemistry Letters*, 18:2633-2639, 2008.

Chintharlapalli et al., "Structure-dependent activity of glycyrrhetinic acid derivatives as peroxisome proliferator-activated receptor γ agonists in colon cancer cells," *Molecular Cancer Therapeutics*, 6 (5): 1588-1598, 2007.

Clinton et al., "Steroidal [3,2-c]pyrazoles. II. Androstanes, 19-norandrostanes and their unsaturated analogs," *J. Am Chem Soc.*, 83:1478-1491, 1961.

Connolly et al., "Grandiofolione: a novel tetranortriterpenoid," *Chemical Communications*, 23:867-568, 1966.

De Ruggieri et al., "Deidrogenazione e bromurazione di beta-chetonitrili steroidali," *Il Farmaco*, 20: 358-388, 1964. (English summary).

Dinkova-Kostova et al., "Extremely potent triterpenoid inducers of the phase 2 response: correlations of protection against oxidant and

(56) References Cited

OTHER PUBLICATIONS inflammatory stress," *Proc. Natl. Acad. Sci.*, 102(12): 4584-4589, 2005.
Duan et al., "Immunosuppressive terpenoids from extracts of *Tripterygium wilfordii*," *Tetrahedron*, 57 (40): 8413-8424, 2001.
Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.
Ferreira et al., "Phytochemistry of the mopane, *Colophosperum mopane*," *Phytochemistry*, 64 (1): 31-51, 2003.
Finlay et al., "Novel A-ring cleaved analogs of oleanolic and ursolic acids which affect growth regulation in NRP.152 prostate cells," *Biorg. Med. Chem. Lett.*, 7(13): 1769-1772, 1997.
Finlay et al., "The Effects of A and C Ring Modification of Oleanolic and Ursolic Acid on the Inhibition of Nitric Oxide Formation in Mouse Macrophages," 213th American Chemical Society National Meeting, Abstract: 084, 1997.
Hatcher et al., "Curcumin: from ancient medicine to current clinical trials," *CMLS Cellular and Molecular Life Sciences*, 65 (11): 1631-1652, 2008.
Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 12:1027-1030, 2002.
Honda et al., "An efficient synthesis of tricyclic compounds (+)—(4aβ, 8aβ, 10aα)—1,2,3,4,4a,6,7,8,8a,9,10,10a-Dodecahydro-1,1,4a-Trimethyl-2-Oxophenanthrene-8a-Carboxolic acid, its methyl ester, and (+)-(4aβ,8aβ,10aα)-3,4,4a,6,7,8,8a,9,10,10a-Decahydro-8a-hydroxymethyl-1,1,4a-trimethylphenanthren-2(1H)-one," *Org. Prep. Proced. Int*, 37(6): 546-550, 2005.
Honda et al., "Design and synthesis of 23, 24-dinoroleanolic acid derivatives, novel triterpenoid—steroid hybrid molecules," *J. Org. Chem.*, 63:4846-4849, 1998.
Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.
Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.
Honda et al., "Efficient synthesis of (−)- and (+)-tricyclic compounds with enome functionalities in rings A and C. A novel class of orally active anti-inflammatory and cancer chemopreventive agents," *Org Biomol Chem.*, 1:4384-4391, 2003.
Honda et al., "New enone derivatives of oleanolic acid and ursolic acid as inhibitors of nitric oxide production in mouse macrophages," *Bioorg. Med. Chem. Lett.*, 7:1623-1628, 1997.
Honda et al., "New synthetic oleanane and ursane triterpenoids as inhibitors of nitric oxide production in mouse macrophages," The Fifth Chemical Congress of North America, Cancun, Mexico, Abstract 552 and slides for oral presentation, Nov. 1997.
Honda et al., "Novel synthetic oleanane and ursane triterpenoids with various enone functionalities in ring A as inhibitors of nitric oxide production in mouse macrophages," *J. Med. Chem.*, 43:1866-1877, 2000.
Honda et al., "Novel synthetic oleanane triterpenoids: a series of highly active inhibitors of nitric oxide production in mouse macrophages," *Bioorg Med Chem Lett*, 9(24):3429-3434, 1999.
Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.
Honda et al., "Revision and confirmation of the regiochemistry of isoxazoles derived from methyl oleanonate and lanost-8-en-3-one. Synthesis of a new lanostane triterpenoid with a cyano-enone functionality in ring A," J. Org. Chem., 68:4991-4993, 2003.
Honda et al., "Synthesis of (±)-3 ,3 -ethylenedioxy -14α-hydroxy-5 -picrasene-11,16-dione , a 14αH-picrasane derivative," *Chem. Lett.*, 299-302, 1981.
Honda et al., "Synthesis of a novel dicyano abietane analogue: a potential antiinflammatoiy agent," *J. Org. Chem.*, 71:3314-3316, 2006.
Honda et al., "Synthetic oleanane and ursane triterpenoids with modified rings A and C: A series of highly active inhibitors of nitric oxide production in mouse macrophages," *J. Med. Chem.*, 43:4233-4246, 2000.
Honda, et al., "Tricyclic Compounds Containing Nonenolizable Cyano Enones. A Novel Class of Highly Potent Anti-Inflammatory and Cytoprotective Agents[79]," *J. Med. Chem.*, 54(6):1762-1778, 2011.
Hybertson, et al., "Oxidative stress in health and disease: The therapeutic potential of Nrf2 activation", *Molecular Aspects of Medicine*, 2011, 32:234-246.
International Preliminary Report on Patentability issued in corresponding PCT Application. PCT/US2016/017769, dated Aug. 15, 2017.
International Search Report and Written Opinion issued in corresponding PCT Application No. PCT/US2016/017769, dated Apr. 15, 2016.
Kincl et al., "Pituitary gonadotropin inhibitory action of neutral steroids," *Acta Endocrinologica*, 46: 300-306, 1964.
Kobayashi et al., "The antioxidant defense system Keapl-Nrf2 comprises a multiple sensing mechanism for responding to a wide range of chemical compounds," *Mol. Cell Biol.*, 29(2):493-502, 2009.
Konopleva et al., "Activation of nuclear transcription factor PPARγ by the novel triterpenoid CDDO as targeted therapy in breast cancer," 2002 Keystone Symposium, Abstract No. 539, 2002.
Konopleva et al., "Mechanisms and Activity of PPARγ-Active Triterpenoids CDDO and CDDO-Me in Leukemias," *Blood*, 106:2460, 2005.
Konopleva et al., "Novel synthetic triterpenoid CDDO-Me: potent antiproliferative, proapoptotic and differentiating agent in AML," *Blood*, 96(11), Part 1: 121A, abstract # 522, 2000.
Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.
Konopleva et al., "Novel triterpenoid CDDO-Me is a potent inducer of apoptosis and differentiation in acute myelogenous leukemia," *Blood*, 99(1):326-335, 2002.
Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.
Konopleva et al., "PPARγ Ligand CDDO Induces Apoptosis in Leukemias Via Multiple Apoptosis Pathways," Abstracts of the 44th Annual Meeting of the American Society of Hematology, Abstract No. 2209, 2002.
Konopleva et al., "PPARγ Ligands Are Potent Inducers of Apoptosis in Leukemias and Lymphomas," American Society of Hematology 43rd Annual Meeting and Exposition, Abstract No. 501, 2001.
Konopleva et al., "PPARγ Nuclear Receptor as a Novel Molecular Target in Leukemia Therapy," *Proc. Amer. Assoc. Cancer Res.*, 43:4730, 2002.
Konopleva et al., "PPARγ nuclear receptor as a novel therapeutic target in AML," *Blood*, 96(11):460a, Abstract #1982, 2000.
Konopleva et al., "PPARγ nuclear receptor as a novel therapeutic target in AML," *Proc. of the AACR*, 42, Abstract #4458, 2001.
Konopleva et al., "Suppression of ERK Activation is Required for Triterpenoid Methyl-CDDO-Induced Apoptosis in AML," *Blood*, 102(11):1404, 2003.
Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.
Konopleva et al., "Synthetic triterpenoid CDDO as a novel therapy for resistant breast cancer," *Proc. Amer. Assoc. Cancer Res.*, 44:2726, 2003.

(56) References Cited

OTHER PUBLICATIONS

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.

Liby et al., "Novel semisynthetic analogues of betulinic acid with diverse cytoprotective, antiproliferative, and proapoptotic activities," *Mol. Cancer. Ther.*, 6(7): 2113-2119, 2007.

Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.

Liby et al., "The synthetic triterpenoid CDDO-Imidazolide suppresses STAT phosphorylation and induces apoptosis in myeloma and lung cancer cells," *Clinical Cancer Research*, 12 (14 Part 1): 4288-4293, 2006.

Liby et al., "The synthetic triterpenoids CDDO-Methyl ester and CDDO-ethyl amide prevent lung cancer induced by vinyl carbamate in A/J mice," *Cancer Research*, 67 (6): 1-7, 2007.

Liby et al., "The synthetic triterpenoids, CDDO and CDDO-imidazolide, are potent inducers of heme oxygenase-1 and Nrf2/ARE signaling," *Cancer Res.*, 65:4789-4798, 2005.

Liby et al., "Triterpenoids and rexinoids as multifunctional agents for the prevention and treatment of cancer," *Nat. Rev. Cancer*, 7 (5): 357-369, 2007.

Orr et al, "Steroids. CCLXV. Studies in cyano steroids. 3. Unsaturated 2-cyano steroids," *J. Org. Chem.*, 29(11): 3300-3303, 1964.

Ribo et al., "Synthesis of methyl 1,11-dioxoolean-2,12-dien-30-oate and its 24-nor derivative," *Afinidad*, 38(373): 197-200, 1981.

Satoh et al., "Activation of the Keap1/Nrf2 pathway for neuroprotection by electrophilic phase II inducers," *PNAS*, 103 (3): 768-773, 2006.

Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.

Shin et al., "NRF2 modulates aryl hydrocarbon receptor signaling: influence on adipogenesis," *Molecular and Cellular Biology*, 27 (20): 7188-7197, 2007.

Sporn et al., "New Synthetic Triterpenoids: Potent Agents for Prevention and Treatment of Tissue Injury Caused by Inflammatory and Oxidative Stress," *J. Nat. Prod.*, 74(3):537-545, 2011.

Subba Rao, et al., "Chemical modifications of natural triterpenes—glycyrrhetinic and boswellic acids: evaluation of their biological activity," *Tetrahedron*, 64(51):11541-11548, 2008.

Suh et al., "A novel synthetic oleanane triterpenoid, 2-cyano-3,12-dioxoolean-1,9-dien-28-oic acid (CDDO), induces cell differentiation in human myeloid leukemias," Proceedings of the American Association for Cancer Research Annual Meeting, 40:300, abstract 1988, 1999.

Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.

Suh et al., "New triterpenoids as cancer preventive and anti-inflammatory agents," Proceedings of the American Association for Cancer Research, Abstract No. 1457, 38: 216, 1997.

Suh et al., "Novel triterpenoids suppress inducible nitric oxide synthase (iNOS) and inducible cyclooxygenase (COX-2) in mouse macrophages," *Cancer Res.*, 58:717-723, 1998.

Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.

Suh et al., "Synthetic triterpenoids activate a pathway for apoptosis in AML cells involving downregulation of FLIP and sensitization to TRAIL," *Leukemia*, 17:2122-2129, 2003.

Suh et al., "Synthetic triterpenoids enhance transforming growth factor β/Smad signaling," *Cancer Res.*, 63:1371-1376, 2003.

Suh et al., "Triterpenoids CDDO and CDDO-Me Down-Regulate FLIP Expression and Sensitize AML Cells to Trail-Induced Apoptosis," American Society of Hematology 43rd Annual Meeting and Exposition, Abstract No. 498, 2001.

Sun et al., "Structure-activity relationships of oleanan- and ursane-type triterpenoids," *Botanical Studies*, 47:339-368, 2006.

Yates et al., "Potent protection against aflatoxin-induced tumorigenesis through induction of Nrf2-regulated pathways by the triterpenoid 1[2-cyano-3-,12-dioxooleana-1,9(11)-dien-28-oyl]imidazole," *Cancer Res.*, 66 (4): 2488-2494, 2007.

You et al., "Synthesis and cytotoxic activity of a-ring modified betulinic acid derivatives," *Bioorganic and Medicinal Chemistry Letters*, 13 (19): 3137-3140, 2003.

* cited by examiner

IMIDAZOLYL TRICYCLIC ENONES AS ANTIOXIDANT INFLAMMATION MODULATORS

This application is a national phase application under 35 U.S.C. § 371 of International Application No. PCT/US2016/017769, filed on Feb. 12, 2016, which claims the benefit of priority to U.S. Provisional Application Ser. No. 62/115,247, filed on Feb. 12, 2015, the entire contents of each are hereby incorporated by reference.

BACKGROUND OF THE INVENTION

I. Field of the Invention

The present invention relates generally to the fields of biology and medicine. More particularly, it concerns compounds, compositions and methods for the treatment and prevention of diseases such as those associated with oxidative stress and inflammation.

II. Description of Related Art

The anti-inflammatory and anti-proliferative activity of the naturally occurring triterpenoid, oleanolic acid, has been improved by chemical modifications. For example, 2-cyano-3,12-diooxooleana-1,9(11)-dien-28-oic acid (CDDO) and related compounds have been developed (Honda et al., 1997; Honda et al., 1998; Honda et al., 1999; Honda et al., 2000a; Honda et al., 2000b; Honda, et al., 2002; Suh et al. 1998; Suh et al., 1999; Place et al., 2003; Liby et al., 2005). Compounds derived from oleanolic acid have also been shown to affect the function of multiple protein targets and thereby modulate the activity of several important cellular signaling pathways related to oxidative stress, cell cycle control, and inflammation. See, for example, Dinkova-Kostova et al., 2005; Ahmad et al., 2006; Ahmad et al., 2008; Liby et al., 2007a and U.S. Pat. Nos. 8,129,429, 7,915,402, 8,124,799, 7,943,778 and WO 2013/163344. The methyl ester, bardoxolone-methyl (CDDO-Me), has been evaluated as a treatment for diabetic nephropathy, chronic kidney disease, and cancer (Pergola, et al., 2011; Hong, et al., 2012). Bardoxolone methyl is currently being evaluated for the treatment of pulmonary arterial hypertension (WO 2015/027206). Other analogs of CDDO have been developed and evaluated for other indications for treatment of diseases or disorders which are associated with inflammation or cellular proliferation (WO 2013/163344 and Reisman, et al., 2014).

Despite these promising properties, oleanolic acid derivatives are all dependent on natural product precursors. Use of other, including simpler or less expensive starting materials can minimize supply chain-related risks, including potential lack of availability due to adverse weather conditions, disease, and other environmental factors. Previous synthetic efforts include a class of compounds known as tricyclic bis-enones (TBEs) (Honda, et al., 2003; Favaloro, et al., 2002; WO 2008/064133; Honda, et al., 2011). These TBE compounds contained two cyano enone structures, one in each of the A and C rings. More recently, tricyclic compounds with pyrazolyl or pyrimidinyl groups were developed (WO 2012/083306). The further development of new compounds continues to be of interest because the biological activity profiles of known antioxidant inflammation modulating compounds varies and because of the wide variety of potential diseases and disorders that may be treated or prevented with such compounds, as well as manufacturing and supply-chain related considerations.

SUMMARY OF THE INVENTION

The present disclosure provides novel compounds, including imidazolyl tricyclic enones with anti-inflammatory and/or antioxidant properties, pharmaceutical compositions thereof, methods for their manufacture, and methods for their use.

In one aspect of the present disclosure there are provided compounds of the formula:

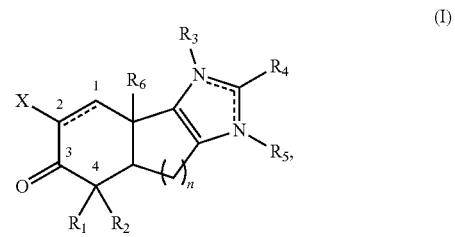

wherein: the atoms labeled 1 and 2 are connected either by a single bond, a double bond or an epoxidized double bond; n is 1 or 2; X is —CN, —CF$_3$, or —C(O)R$_a$, wherein R$_a$ is —OH, —NH$_2$, alkoxy$_{(C≤6)}$, alkylamino$_{(C≤6)}$, dialkylamino$_{(C≤6)}$, or —NHS(O)$_2$-alkyl$_{(C1-4)}$; R$_1$ and R$_2$ are each independently hydrogen, hydroxy, halo, or amino; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or R$_1$ and R$_2$ are taken together and are alkanediyl$_{(C≤12)}$, alkenediyl$_{(C≤12)}$, alkoxydiyl$_{(C≤12)}$, alkylaminodiyl$_{(C≤12)}$, or a substituted version of any of these groups; R$_3$ is: absent, hydrogen; or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$ or a substituted version of any of these groups, provided that R$_3$ is absent when the atom to which it is bound forms part of a double bond; R$_4$ is: hydrogen, hydroxy, amino, halo, or cyano; or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or -alkanediyl$_{(C≤6)}$-Y$_1$, wherein Y$_1$ is: hydroxy, amino, halo, or cyano; or acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of these groups; and R$_5$ is: absent, hydrogen, hydroxy, or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; provided that R$_5$ is absent when the atom to which it is bound forms part of a double bond; -alkanediyl$_{(C\leq6)}$-Y$_2$; -arenediyl$_{(C\leq8)}$-Y$_3$; or -arenediyl$_{(C\leq8)}$-alkanediyl$_{(C\leq6)}$-Y$_4$, wherein Y$_2$, Y$_3$, and Y$_4$ are each independently: hydroxy, amino, halo, cyano, or alkyl$_{(C\leq12)}$, aryl$_{(C\leq12)}$, heteroaryl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; R$_6$ is alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, or a substituted version of any of these groups; or a pharmaceutically acceptable salt thereof.

In some embodiments, the compound is further defined by the formula:

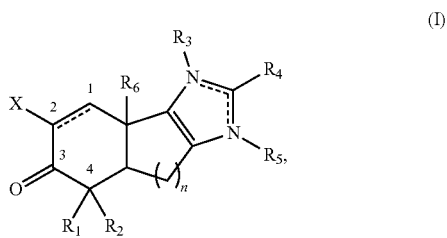

(I)

wherein: the atoms labeled 1 and 2 are connected either by a single bond, a double bond or an epoxidized double bond; n is 1 or 2; X is —CN, —CF$_3$, or —C(O)R$_a$, wherein R$_a$ is —OH, —NH$_2$, alkoxy$_{(C\leq6)}$, alkylamino$_{(C\leq6)}$, dialkylamino$_{(C\leq6)}$, or —NHS(O)$_2$-alkyl$_{(C1-4)}$; R$_1$ and R$_2$ are each independently hydrogen, hydroxy, halo, or amino; or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; or R$_1$ and R$_2$ are taken together and are alkanediyl$_{(C\leq12)}$, alkenediyl$_{(C\leq12)}$, alkoxydiyl$_{(C\leq12)}$, alkylaminodiyl$_{(C\leq12)}$, or a substituted version of any of these groups; R$_3$ is: absent, hydrogen; or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$ or a substituted version of any of these groups, provided that R$_3$ is absent when the atom to which it is bound forms part of a double bond; R$_4$ is: hydrogen, hydroxy, amino, halo, or cyano; or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; or -alkanediyl$_{(C\leq6)}$-Y$_1$ wherein Y$_1$ is: hydroxy, amino, halo, or cyano; or acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of these groups; and R$_5$ is: absent, hydrogen, hydroxy, or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; provided that R$_5$ is absent when the atom to which it is bound forms part of a double bond; -alkanediyl$_{(C\leq6)}$-Y$_2$; -arenediyl$_{(C\leq8)}$-Y$_3$; or -arenediyl$_{(C\leq8)}$-alkanediyl$_{(C\leq6)}$-Y$_4$, wherein Y$_2$, Y$_3$, and Y$_4$ are each independently: hydroxy, amino, halo, cyano, or alkyl$_{(C\leq12)}$, aryl$_{(C\leq12)}$, heteroaryl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; R$_6$ is alkyl$_{(C\leq12)}$, aryl$_{(C\leq12)}$, aralkyl$_{(C\leq12)}$, or a substituted version of any of these groups; or a pharmaceutically acceptable salt thereof.

In some embodiments, the compound is further defined by the formula:

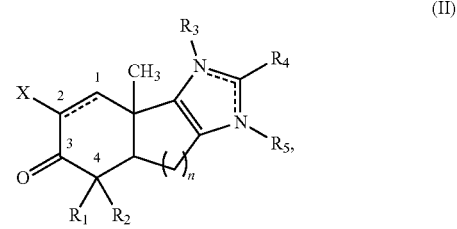

(II)

wherein: the atoms labeled 1 and 2 are connected either by a single bond, a double bond or an epoxidized double bond; n is 1 or 2; X is —CN, —CF$_3$, or —C(O)R$_a$, wherein R$_a$ is —OH, —NH$_2$, alkoxy$_{(C\leq6)}$, alkylamino$_{(C\leq6)}$, dialkylamino$_{(C\leq6)}$, or —NHS(O)$_2$-alkyl$_{(C1-4)}$; R$_1$ and R$_2$ are each independently hydrogen, hydroxy, halo, or amino; or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; or R$_1$ and R$_2$ are taken together and are alkanediyl$_{(C\leq12)}$, alkenediyl$_{(C\leq12)}$, alkoxydiyl$_{(C\leq12)}$, alkylaminodiyl$_{(C\leq12)}$, or a substituted version of any of these groups; R$_3$ is: absent, hydrogen; or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$ or a substituted version of any of these groups, provided that R$_3$ is absent when the atom to which it is bound forms part of a double bond; R$_4$ is: hydrogen, hydroxy, amino, halo, or cyano; or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; or -alkanediyl$_{(C\leq6)}$-Y$_1$ wherein Y$_1$ is: hydroxy, amino, halo, or cyano; or acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of these groups; and R$_5$ is: absent, hydrogen, hydroxy, or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; provided that $R_5$ is absent when the atom to which it is bound forms part of a double bond; -alkanediyl$_{(C≤6)}$-$Y_2$; -arenediyl$_{(C≤8)}$-$Y_3$; or -arenediyl$_{(C≤8)}$-alkanediyl$_{(C≤6)}$-$Y_4$, wherein $Y_2$, $Y_3$, and $Y_4$ are each independently: hydroxy, amino, halo, cyano, or alkyl$_{(C≤12)}$, aryl$_{(C≤12)}$, heteroaryl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or a pharmaceutically acceptable salt thereof.

In some embodiments, the compound is further defined by the formula:

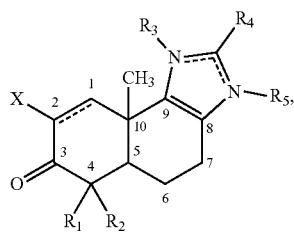

(III)

wherein: X is —CN, —CF$_3$, or —C(O)$R_a$, wherein $R_a$ is —OH, —NH$_2$, alkoxy$_{(C≤6)}$, alkylamino$_{(C≤6)}$, dialkylamino$_{(C≤6)}$, or —NHS(O)$_2$-alkyl$_{(C1-4)}$; $R_1$ and $R_2$ are each independently hydrogen, hydroxy, halo, or amino; or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or $R_1$ and $R_2$ are taken together and are alkanediyl$_{(C≤12)}$, alkenediyl$_{(C≤12)}$, alkoxydiyl$_{(C≤12)}$, alkylaminodiyl$_{(C≤12)}$, or a substituted version of any of these groups; $R_3$ is: absent, hydrogen; or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$ or a substituted version of any of these groups, provided that $R_3$ is absent when the atom to which it is bound forms part of a double bond; $R_4$ is: hydrogen, hydroxy, amino, halo, or cyano; or cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or -alkanediyl$_{(C≤6)}$-$Y_1$ wherein $Y_1$ is: hydroxy, amino, halo, or cyano; or acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of these groups; and $R_5$ is: absent, hydrogen, hydroxy, or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; provided that $R_5$ is absent when the atom to which it is bound forms part of a double bond; -alkanediyl$_{(C≤6)}$-$Y_2$; -arenediyl$_{(C≤8)}$-$Y_3$; or -arenediyl$_{(C≤8)}$-alkanediyl$_{(C≤6)}$-$Y_4$, wherein $Y_2$, $Y_3$, and $Y_4$ are each independently: hydroxy, amino, halo, cyano, or alkyl$_{(C≤12)}$, aryl$_{(C≤12)}$, heteroaryl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or a pharmaceutically acceptable salt thereof.

In some embodiments, the compound is further defined by the formula:

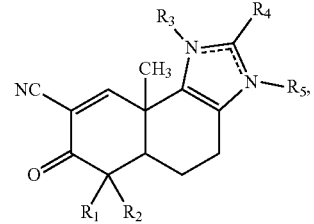

(IV)

wherein: $R_1$ and $R_2$ are each independently hydrogen, hydroxy, halo, or amino; or alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or $R_1$ and $R_2$ are taken together and are alkanediyl$_{(C≤12)}$, alkenediyl$_{(C≤12)}$, alkoxydiyl$_{(C≤12)}$, alkylaminodiyl$_{(C≤12)}$, or a substituted version of any of these groups; $R_3$ is: absent, hydrogen; or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$ or a substituted version of any of these groups, provided that $R_3$ is absent when the atom to which it is bound forms part of a double bond; $R_4$ is: hydrogen, hydroxy, amino, halo, or cyano; or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; or -alkanediyl$_{(C≤6)}$-$Y_1$ wherein $Y_1$ is: hydroxy, amino, halo, or cyano; or acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of these groups; and $R_5$ is: absent, hydrogen, hydroxy, or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, alkoxy$_{(C≤12)}$, aryloxy$_{(C≤12)}$, aralkoxy$_{(C≤12)}$, heteroaryloxy$_{(C≤12)}$, acyloxy$_{(C≤12)}$, alkylamino$_{(C≤12)}$, dialkylamino$_{(C≤12)}$, arylamino$_{(C≤12)}$, aralkylamino$_{(C≤12)}$, heteroarylamino$_{(C≤12)}$, amido$_{(C≤12)}$, or a substituted version of any of these groups; provided that $R_5$ is absent when the atom to which it is bound forms part of a double bond; -alkanediyl$_{(C≤6)}$-$Y_2$; -arenediyl$_{(C≤8)}$-$Y_3$; or -arenediyl$_{(C≤8)}$- alkanediyl$_{(C\leq 6)}$-Y$_4$, wherein Y$_2$, Y$_3$, and Y$_4$ are each independently: hydroxy, amino, halo, cyano, or alkyl$_{(C\leq 12)}$, aryl$_{(C\leq 12)}$, heteroaryl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; or a pharmaceutically acceptable salt thereof.

In some embodiments, the compound is further defined by the formula:

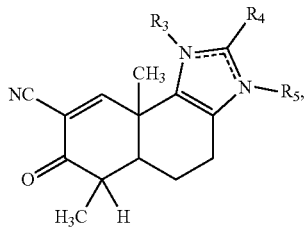

(V)

wherein: R$_3$ is: absent, hydrogen; or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$ or a substituted version of any of these groups, provided that R$_3$ is absent when the atom to which it is bound forms part of a double bond; R$_4$ is: hydrogen, hydroxy, amino, halo, or cyano; or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; or -alkanediyl$_{(C\leq 6)}$-Y$_1$ wherein Y$_1$ is: hydroxy, amino, halo, or cyano; or acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of these groups; and R$_5$ is: absent, hydrogen, hydroxy, or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; provided that R$_5$ is absent when the atom to which it is bound forms part of a double bond; -alkanediyl$_{(C\leq 6)}$-Y$_2$; -arenediyl$_{(C\leq 8)}$-Y$_3$; or -arenediyl$_{(C\leq 8)}$-alkanediyl$_{(C\leq 6)}$-Y$_4$, wherein Y$_2$, Y$_3$, and Y$_4$ are each independently: hydroxy, amino, halo, cyano, or alkyl$_{(C\leq 12)}$, aryl$_{(C\leq 12)}$, heteroaryl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; or a pharmaceutically acceptable salt thereof.

In some embodiments, the compound is further defined by the formula:

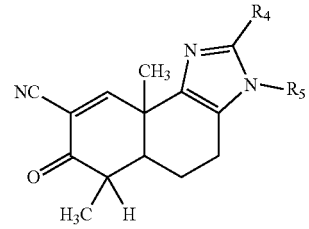

(VI)

wherein: R$_4$ is: hydrogen, hydroxy, amino, halo, or cyano; or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; or -alkanediyl$_{(C\leq 6)}$-Y$_1$ wherein Y$_1$ is: hydroxy, amino, halo, or cyano; or acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of these groups; and R$_5$ is: absent, hydrogen, hydroxy, or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; provided that R$_5$ is absent when the atom to which it is bound forms part of a double bond; -alkanediyl$_{(C\leq 6)}$-Y$_2$; -arenediyl$_{(C\leq 8)}$-Y$_3$; or -arenediyl$_{(C\leq 8)}$-alkanediyl$_{(C\leq 6)}$-Y$_4$, wherein Y$_2$, Y$_3$, and Y$_4$ are each independently: hydroxy, amino, halo, cyano, or alkyl$_{(C\leq 12)}$, aryl$_{(C\leq 12)}$, heteroaryl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; or a pharmaceutically acceptable salt thereof. In some embodiments, the compound is further defined as: R$_4$ is: hydrogen, hydroxy, amino, halo, or cyano; or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; and R$_5$ is: hydrogen, hydroxy, or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups. In some embodiments, the compound is further defined as: R$_4$ is hydroxy, amino, halo, cyano, alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, or amido$_{(C\leq12)}$; and $R_5$ is hydrogen, hydroxy, alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, or amido$_{(C\leq12)}$.

In some embodiments, the atoms labeled 1 and 2 are connected by a single bond. In other embodiments, the atoms labeled 1 and 2 are connected by a double bond. In some embodiments, n is 1. In other embodiments, n is 2. In some embodiments, X is cyano. In other embodiments, X is —C(O)$R_a$, wherein $R_a$ is —OH, —NH$_2$, alkoxy$_{(C\leq6)}$, alkylamino$_{(C\leq6)}$, dialkylamino$_{(C\leq6)}$, or —NHS(O)$_2$-alkyl$_{(C1-4)}$. In some embodiments, $R_a$ is —NH$_2$.

In some embodiments, $R_1$ is hydrogen. In other embodiments, $R_1$ is alkyl$_{(C\leq12)}$. In some embodiments, $R_1$ is methyl. In some embodiments, $R_2$ is hydrogen. In other embodiments, $R_2$ is alkyl$_{(C\leq12)}$. In some embodiments, $R_2$ is methyl. In some embodiments, $R_3$ is absent. In some embodiments, $R_3$ is absent, hydrogen; or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$ or a substituted version of any of these groups, provided that $R_3$ is absent when the atom to which it is bound forms part of a double bond.

In some embodiments, $R_4$ is hydrogen, hydroxy, amino, halo, or cyano; or cycloalkyl$_{(C\leq12)}$, aryl$_{(C\leq12)}$, heteroaryl$_{(C\leq12)}$, acyl$_{(C\leq12)}$, amido$_{(C\leq12)}$, or a substituted version of any of these groups; or alkanediyl$_{(C\leq6)}Y_1$, wherein $Y_1$ is: hydroxy, amino, halo, or cyano; or acyl$_{(C\leq12)}$, alkoxy$_{(C\leq12)}$, aralkoxy$_{(C\leq12)}$, acyloxy$_{(C\leq12)}$, amido$_{(C\leq12)}$, or a substituted version of these groups. In some embodiments, $R_4$ is cyano. In other embodiments, $R_4$ is halo. In some embodiments, $R_4$ is bromo. In other embodiments, $R_4$ is substituted acyl$_{(C\leq12)}$. In some embodiments, $R_4$ is —C(O)NH$_2$. In other embodiments, $R_4$ is alkyl$_{(C\leq12)}$. In some embodiments, $R_4$ is methyl. In other embodiments, $R_4$ is substituted alkyl$_{(C\leq12)}$. In some embodiments, $R_4$ is 2-hydroxyethyl. In other embodiments, $R_4$ is aryl$_{(C\leq12)}$. In some embodiments, $R_4$ is phenyl or 2-methylphenyl. In other embodiments, $R_4$ is heteroaryl$_{(C\leq12)}$. In some embodiments, $R_4$ is 4-pyridyl or 4-(1-methyl)pyrazolyl. In other embodiments, $R_4$ is -alkanediyl$_{(C\leq6)}$-$Y_1$. In some embodiments, the alkanediyl$_{(C\leq6)}$ is —CH$_2$CH$_2$—. In some embodiments, $Y_1$ is hydroxy or aralkoxy$_{(C\leq12)}$. In other embodiments, $Y_1$—OCH$_2$C$_6$H$_5$.

In some embodiments, $R_5$ is hydrogen or alkyl$_{(C\leq12)}$, cycloalkyl$_{(C\leq12)}$, aryl$_{(C\leq12)}$, aralkyl$_{(C\leq12)}$, heteroaryl$_{(C\leq12)}$, acyl$_{(C\leq12)}$, or a substituted version of any of these groups; -alkanediyl$_{(C\leq6)}$-$Y_2$; -arenediyl$_{(C\leq8)}$-$Y_3$; or -arenediyl$_{(C\leq8)}$-alkanediyl$_{(C\leq6)}$-$Y_4$, wherein $Y_2$, $Y_3$, and $Y_4$ are each independently: hydroxy, amino, halo, cyano, or acyl$_{(C\leq12)}$, alkoxy$_{(C\leq12)}$, aryloxy$_{(C\leq12)}$, aralkoxy$_{(C\leq12)}$, alkylamino$_{(C\leq12)}$, dialkylamino$_{(C\leq12)}$, amido$_{(C\leq12)}$, or a substituted version of any of these groups. In some embodiments, $R_5$ is hydrogen. In other embodiments, $R_5$ is alkyl$_{(C\leq12)}$ or substituted alkyl$_{(C\leq12)}$. In some embodiments, $R_5$ is —CH$_2$CH$_2$CH$_2$OCH$_3$. In other embodiments, $R_5$ is aryl$_{(C\leq12)}$. In some embodiments, $R_5$ is phenyl, 2-methylphenyl, 1,1'-biphenyl-4-yl, or 1,1'-biphenyl-4-yl. In other embodiments, $R_5$ is substituted aryl$_{(C\leq12)}$. In some embodiments, $R_5$ is

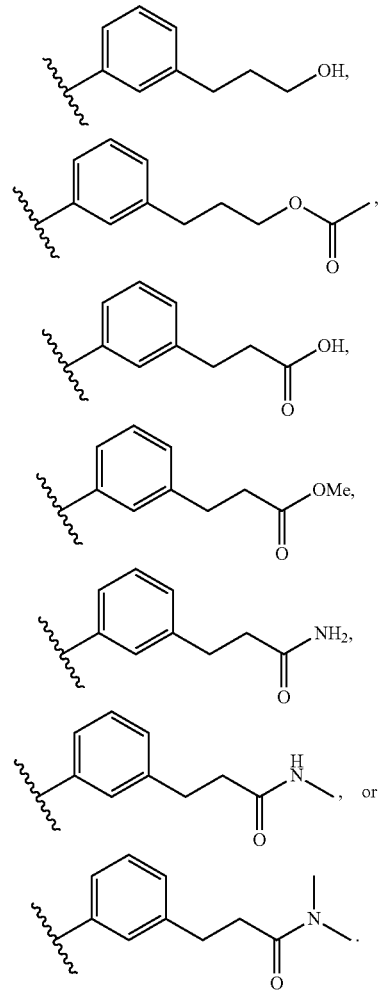

In other embodiments, $R_5$ is heteroaryl$_{(C\leq12)}$. In some embodiments, $R_5$ is 4-(1-methyl)pyrazolyl or 5-(2-methyl)tetrazolyl. In other embodiments, $R_5$ is alkanediyl$_{(C\leq6)}Y_2$. In some embodiments, the alkanediyl$_{(C\leq6)}$ is —CH$_2$CH$_2$CH$_2$—. In some embodiments, $Y_2$ is methoxy. In other embodiments, $R_5$ is arenediyl$_{(C\leq8)}Y_3$. In some embodiments, the arenediyl$_{(C\leq8)}$ is:

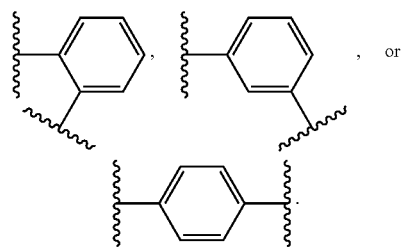

In some embodiments, $Y_3$ is alkyl$_{(C\leq12)}$, aryl$_{(C\leq12)}$, heteroaryl$_{(C\leq12)}$, or substituted versions thereof. In some embodiments, $Y_3$ is alkyl$_{(C\leq12)}$ or substituted alkyl$_{(C\leq12)}$. In other embodiments, $Y_3$ is aryl$_{(C\leq12)}$. In some embodiments, $Y_3$ is phenyl. In other embodiments, $Y_3$ is heteroaryl$_{(C\leq12)}$. In some embodiments, $Y_3$ is 5-pyrimidinyl or 4-(1-methyl)pyrazolyl. In other embodiments, $R_5$ is -arenediyl$_{(C\leq8)}$-alkanediyl$_{(C≤6)}$-Y$_4$. In some embodiments, the alkanediyl$_{(C≤6)}$ is —CH$_2$CH$_2$— or —CH$_2$CH$_2$CH$_2$—. In some embodiments, Y$_4$ is —OH. In other embodiments, Y$_4$ is acyl$_{(C≤12)}$, acyloxy$_{(C≤12)}$, substituted acyl$_{(C≤12)}$, or substituted acyloxy$_{(C≤12)}$. In some embodiments, Y$_4$ is —OC(O)CH$_3$, —NHC(O)CH$_3$, —CO$_2$H, —C(O)NH$_2$, —C(O)NHCH$_3$, —C(O)N(CH$_3$)$_2$, or —CO$_2$CH$_3$.

In some embodiments, R$_6$ is alkyl$_{(C≤12)}$ or substituted alkyl$_{(C≤12)}$. In some embodiments, R$_6$ is methyl. In other embodiments, R$_6$ is aryl$_{(C≤12)}$ or substituted aryl$_{(C≤12)}$. In some embodiments, the carbon atom labeled 4 is in the S configuration. In some embodiments, the carbon atom labeled 5 is in the S configuration. In some embodiments, the carbon atom labeled 10 is in the R configuration.

In some embodiments, the compound is further defined as:

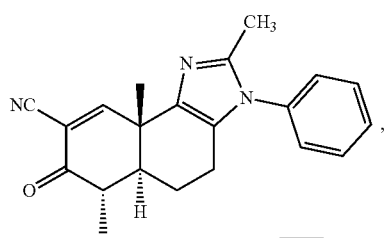

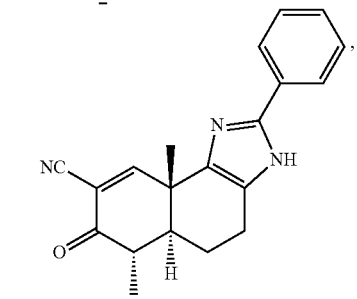

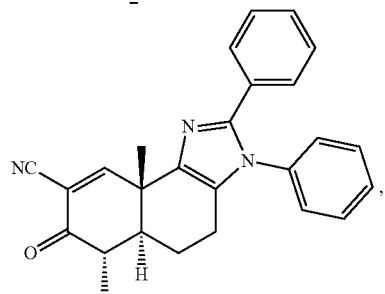

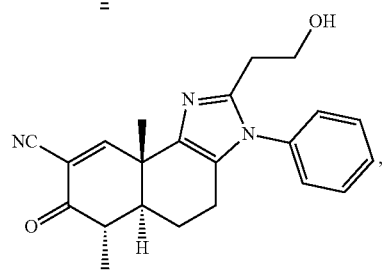

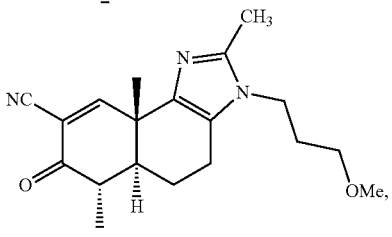

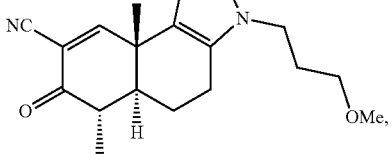

-continued

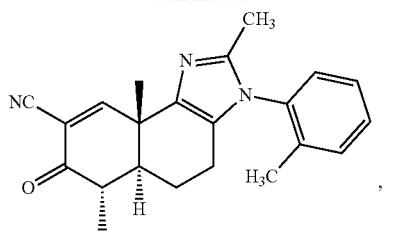

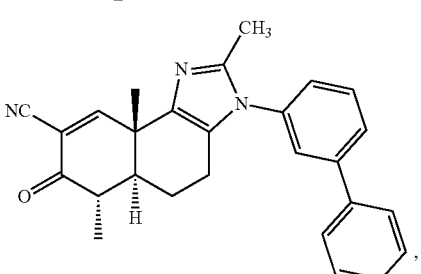

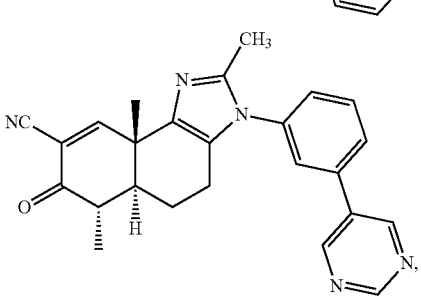

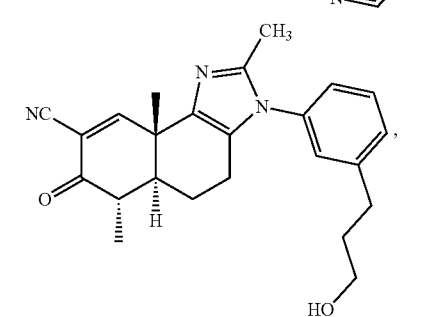

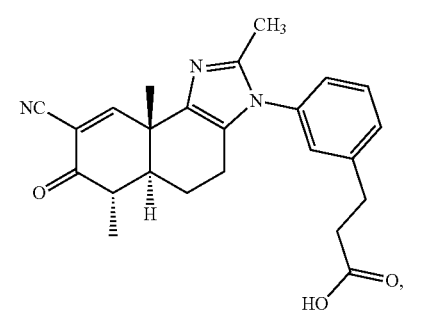

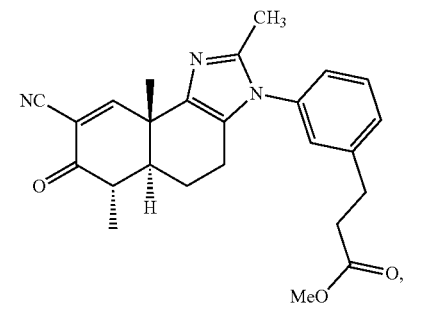

13
-continued
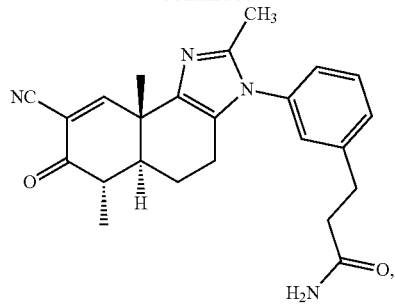
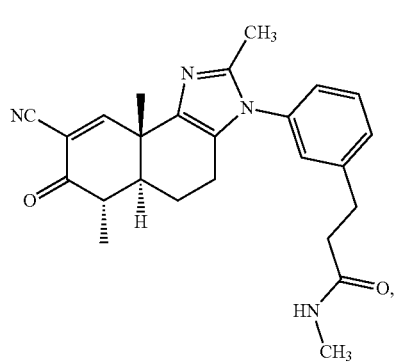
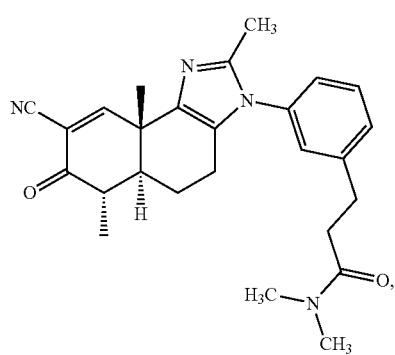
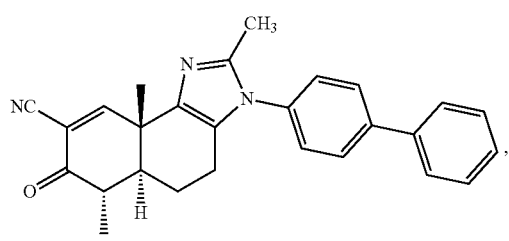
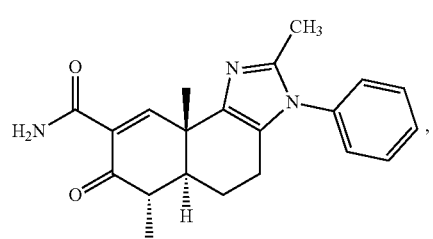
14
-continued
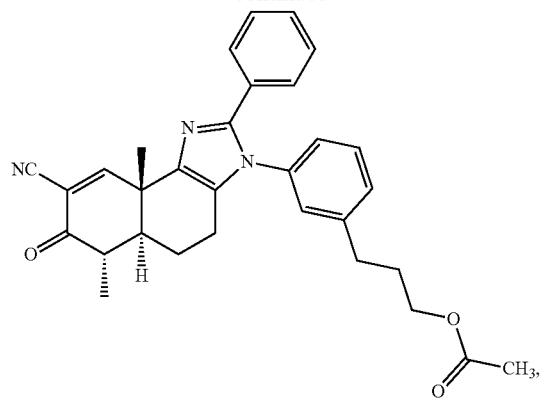
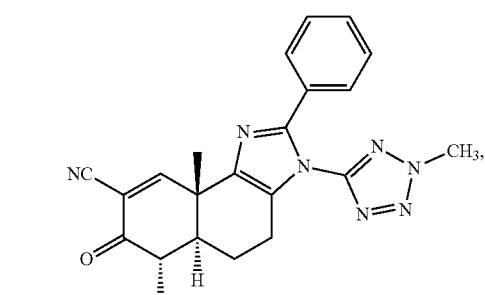
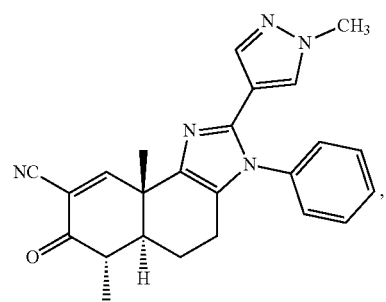
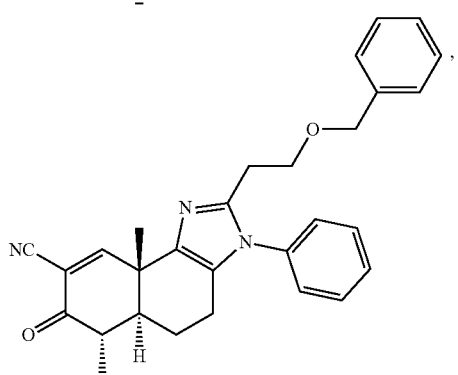
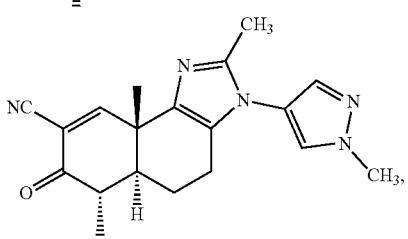

15

-continued

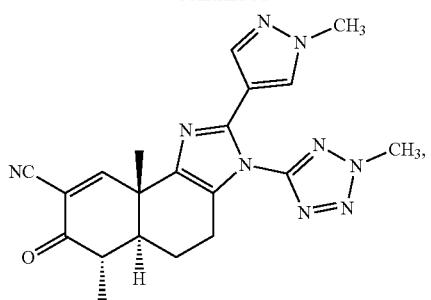

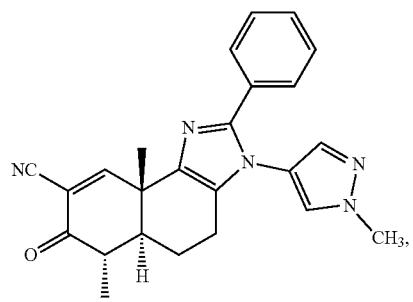

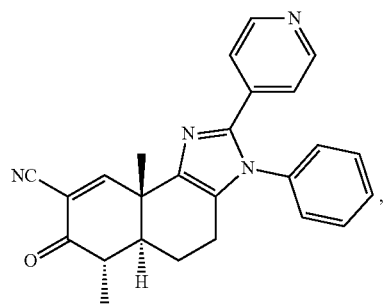

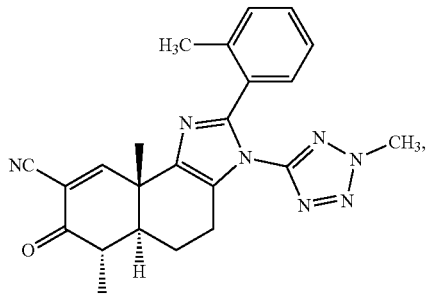

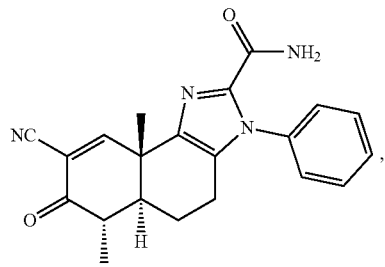

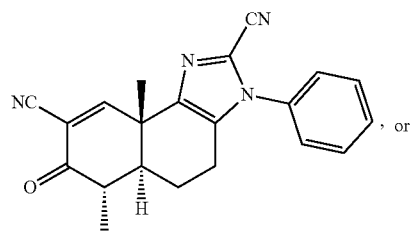

16

-continued

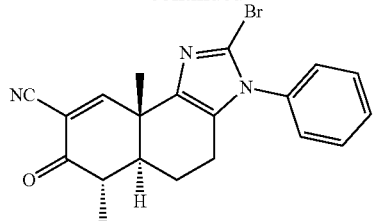

or a pharmaceutically acceptable salt of any of these formulas. In still further embodiments, the compound is further defined as:

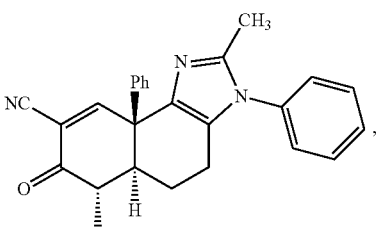

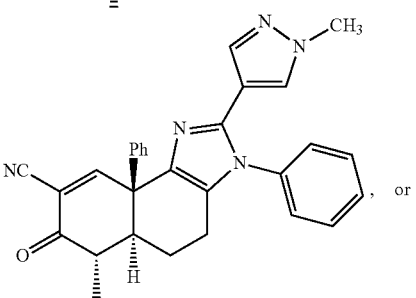

, or

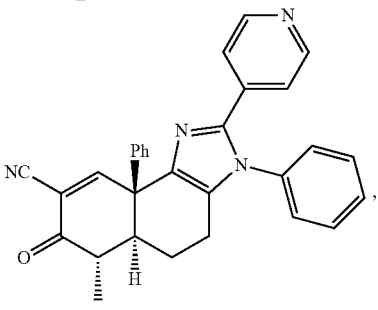

, or a pharmaceutically acceptable salt of any of these formulas.

In yet another aspect, the present disclosure provides a pharmaceutical composition comprising:
  a) a compound of the present disclosure; and
  b) an excipient.

In still another aspect, the present disclosure provides a method of treating a disease or disorder comprising administering to a patient in need thereof a therapeutically effective amount of a compound or composition of the present disclosure. In some embodiments, the patient is a human, primate, horse, cow, sheep, goat, guinea pig, dog, cat, rat, or mouse. In some embodiments, the patient is a human. In some embodiments, the disease or disorder is associated with inflammation. In some embodiments, the disease or disorder is characterized by overexpression of iNOS genes in the patient. In some embodiments, the disease or disorder is characterized by overexpression of COX-2 genes in the patient.

In still yet another aspect, the present disclosure provides a method of inhibiting nitric oxide production comprising administering to a patient in need thereof an amount of the compound or composition of the present disclosure sufficient to cause inhibition of IFN-γ-induced nitric oxide production in one or more cells of the patient.

Other objects, features, and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions with antioxidant and/or anti-inflammatory properties, methods for their manufacture, and methods for their use, including for the treatment and/or prevention of disease.

I. Compounds and Synthetic Methods

The compounds provided by the present disclosure are shown, for example, above in the summary of the invention section and in the claims below. They may be made using the synthetic methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2013), which is incorporated by reference herein. In addition, the synthetic methods may be further modified and optimized for preparative, pilot- or large-scale production, either batch of continuous, using the principles and techniques of process chemistry as applied by a person skilled in the art. Such principles and techniques are taught, for example, in *Practical Process Research & Development* (2012), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. Diseases Associated with Inflammation and/or Oxidative Stress

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications. In some embodiments, the compounds of this invention may be used in the treatment or prevention of inflammation or diseases associated with inflammation. Assay results for the suppression of IFNγ-induced NO production are presented in Example 1 below.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, liver failure, and chronic obstructive pulmonary disease is closely associated with the presence of chronic oxidative stress and inflammation, leading to the development of fibrosis and eventual loss of organ function. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases including degenerative diseases of the central nervous system and the retina.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference.

In one aspect, compounds disclosed herein are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases and disorders involving oxidative stress and dysregulation of inflammatory processes including cancer, complications from localized or total-body exposure to ionizing radiation, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders.

Without being bound by theory, the activation of the antioxidant/anti-inflammatory Keap1/Nrf2/ARE pathway is believed to be implicated in both the anti-inflammatory and anti-carcinogenic properties of the compounds disclosed herein.

In another aspect, compounds disclosed herein may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis and COPD, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds disclosed herein may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

In some embodiments, the compounds disclosed herein may be used in the treatment and prevention of diseases such as cancer, inflammation, Alzheimer's disease, Parkinson's disease, multiple sclerosis, autism, amyotrophic lateral sclerosis, Huntington's disease, autoimmune diseases such as rheumatoid arthritis, lupus, Crohn's disease and psoriasis, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds disclosed herein may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limiting excessive tissue damage to the host.

III. Pharmaceutical Formulations and Routes of Administration

For administration to an animal especially a mammal in need of such treatment, the compounds in a therapeutically effective amount are ordinarily combined with one or more excipients appropriate to the indicated route of administration. The compounds of the present invention are contemplated to be formulated in a manner ameniable to treatment of a veterinary patient as well as a human patient. In some embodiments, the veterinary patient may be a companion animal, livestock animals, zoo animals, and wild animals The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art and may be adapted to the type of animal being treated.

The pharmaceutical compositions useful in the present invention may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions may be suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general a human equivalent dose (HED) in mg/kg can be calculated in accordance with the following formula (see, e.g., Reagan-Shaw et al., *FASEB J.,* 22(3):659-661, 2008, which is incorporated herein by reference):

$$\text{HED (mg/kg)} = \text{Animal dose (mg/kg)} \times (\text{Animal } K_m / \text{Human } K_m) \quad (a)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

IV. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines. See Lu et al. (2011), which is incorporated herein by reference.

V. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof, in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "===" represents a single bond or a double bond. Thus, for example, the formula

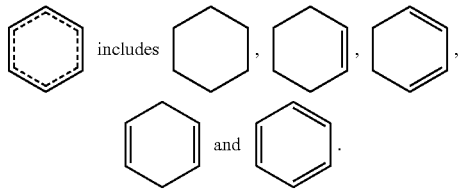

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⦀▬" means a single bond where the group attached to the thick end of the wedge is "into the page". The symbol "⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

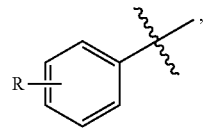

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

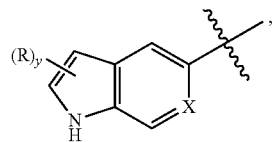

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in a moiety replacing a hydrogen atom is not counted. Thus methoxyhexyl, which has a total of seven carbon atoms, is an example of a substituted alkyl$_{(C1-6)}$.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin"

are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH═CHF, —CH═CHCl and —CH═CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

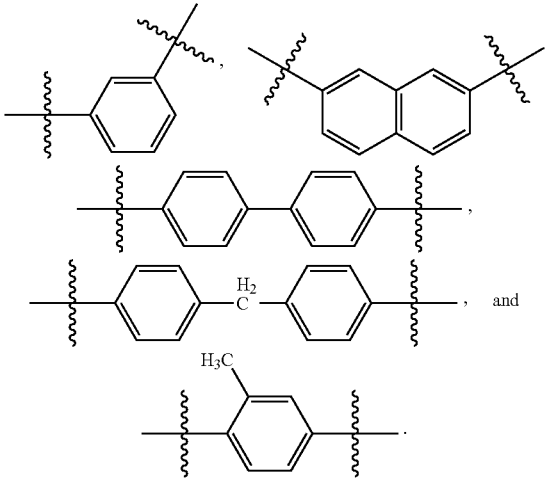

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, and —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p- toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: DMSO, dimethyl sulfoxide; NO, nitric oxide; iNOS, inducible nitric oxide synthase; COX-2, cyclooxygenase-2; FBS, fetal bovine serum; IFNγ or IFN-γ, interferon-γ; TNFα or TNF-α, tumor necrosis factor-α; IL-1β, interleukin-1β; HO-1, inducible heme oxygenase.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Nitric Oxide Production Assays

Tissue Culture:

RAW 264.7, a mouse macrophage cell line, was obtained from American Type Culture Collection (Manassas Va.) and maintained in the log phase of growth in Dulbecco's Modified Eagle's Medium (DMEM), 10% heat inactivated fetal calf serum and 100 units/mL antibiotic-antimycotic (AA). Cells were cultured and maintained in a humidified incubator at 37° C. under 5% $CO_2$ and 95% air. Cells were sub-cultured every 3 days by scraping and were not used beyond passage 20. All cell culture supplies were obtained from Life Technologies (Grand Island, N.Y.).

Nitric Oxide Suppression Assay.

RAW 264.7 cells were plated 1 day in advance of experiment at a concentration of 80,000 cells/well onto CellBIND® 96 well plates (Corning, N.Y.) in a total volume of 100 μL. The next day, pre-treat cells with compounds (from 3 μM to 0.3 nM serially diluted in a 10 point curve) from a 10× stock by adding 10 μL per well in complete DMEM media containing 10% fetal calf serum. The plates were centrifuged for 3 minutes at 400×g at room temperature followed by 2 hour incubation at 37° C. The cells were then incubated overnight at 37° C. with 10 μL of the insult, interferon gamma (R&D Systems, Minneapolis, Minn.), from a 10× stock for a final concentration of 20 ng/mL. The plates were centrifuged for 3 minutes at 400×g at room temperature followed by ~18 hour incubation at 37° C. The following day, transfer 50 μL cell culture supernatant from each well into a clear bottom 96 well plate and follow the instructions from Promega's Griess Detection Kit #G2930 (Madison, Wis.) which involves the addition of 50 μL of the provided sulfanilamide solution for a 5-10 minute incubation at room temperature. Next add 50 μL of the provided N-1-napthylethylenediamine dihydrochloride (NED) solution for a 5-10 minute incubation at room temperature and protected from light. If any air bubbles were introduced into the well, the plates need to be centrifuged for 5 minutes at 400×g at room temperature to avoid interference with absorbance readings. The plates were read for absorbance within 30 minutes with a filter between 520 nm and 550 nm.

For the ability of compounds to suppress the increase in nitric oxide release, the percent maximal intensity of nitric oxide detected in each well was normalized to that induced by the peak value for 20 ng/mL of interferon gamma alone and plotted against the compound concentration to calculate $IC_{50}$ values and to control for plate-to-plate variability. Concentration-response data were analyzed using GraphPad Prism (San Diego, Calif.); the $IC_{50}$ values were derived from a single curve fit to the mean data of n=2-3, in duplicates. Selected data is shown in Table 1.

All compounds were dissolved in dimethyl sulfoxide at 10 mM stock solutions and tested at a concentration that the dimethyl sulfoxide levels never exceeded 1%.

TABLE 1

| Compound Number | Structure | NO IC$_{50}$ (nM) |
| --- | --- | --- |
| T1 | 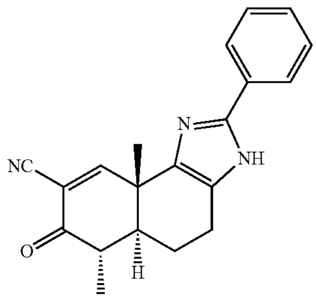 [SMILES: C[C@@H]1C(=O)C(C#N)=C[C@]2(C)c3nc(-c4ccccc4)[nH]c3CC[C@@H]12] | 151 |
| T2 | 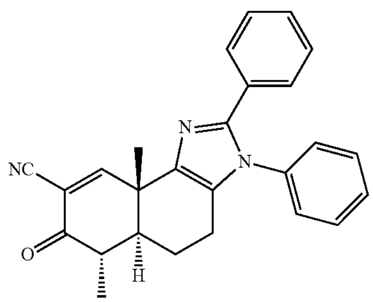 [SMILES: C[C@@H]1C(=O)C(C#N)=C[C@]2(C)c3nc(-c4ccccc4)n(-c4ccccc4)c3CC[C@@H]12] | 471 |
| T3 | 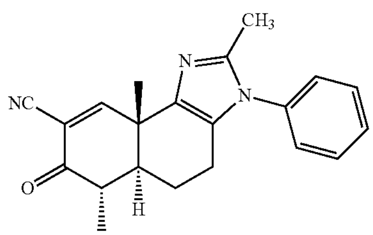 [SMILES: Cc1nc2c(n1-c1ccccc1)CC[C@H]1[C@H](C)C(=O)C(C#N)=C[C@]21C] | 40.8 |
| T4 | 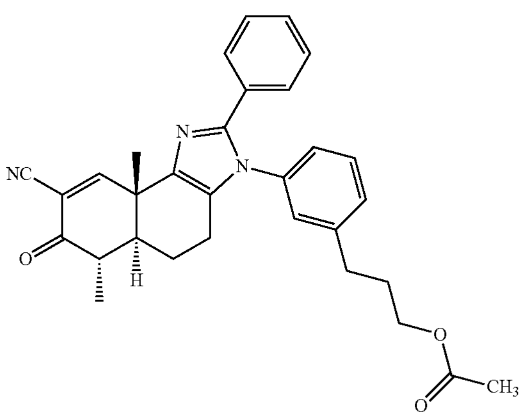 [SMILES: CC(=O)OCCCc1cccc(-n2c(-c3ccccc3)nc3c2CC[C@H]2[C@H](C)C(=O)C(C#N)=C[C@]32C)c1] | 662 |
| T5 | | 136 |

TABLE 1-continued

| Nitric Oxide Inhibition | | |
|---|---|---|
| Compound Number | Structure | NO IC$_{50}$ (nM) |
| T6 | | 19.4 |
| T7 | | 91.8 |
| T8 | | 28.8 |
| T9 | | 22.7 |
| T10 | | 62.8 |

TABLE 1-continued

Nitric Oxide Inhibition

| Compound Number | Structure | NO IC$_{50}$ (nM) |
|---|---|---|
| T11 | 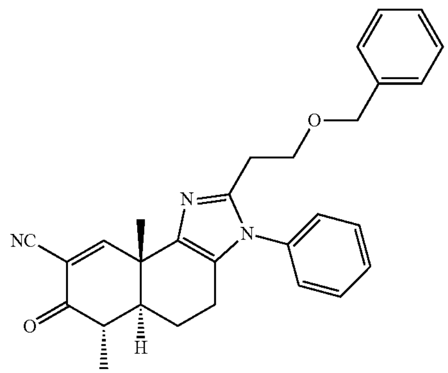 [SMILES: C[C@@H]1C(=O)C(C#N)=C[C@]2(C)c3nc(CCOCc4ccccc4)n(-c4ccccc4)c3CC[C@@H]12] | 93.2 |
| T12 | 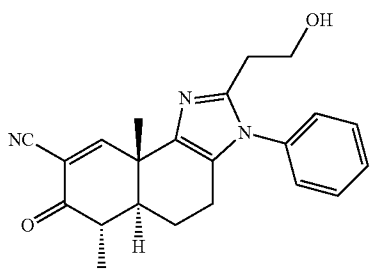 [SMILES: C[C@@H]1C(=O)C(C#N)=C[C@]2(C)c3nc(CCO)n(-c4ccccc4)c3CC[C@@H]12] | 11.3 |
| T13 | 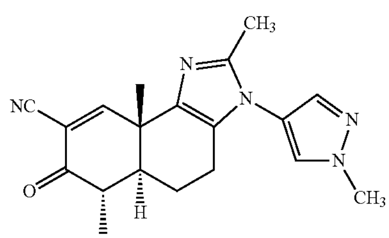 [SMILES: Cc1nc2c(n1-c1cnn(C)c1)CC[C@H]1[C@H](C)C(=O)C(C#N)=C[C@]21C] | 233 |
| T14 | 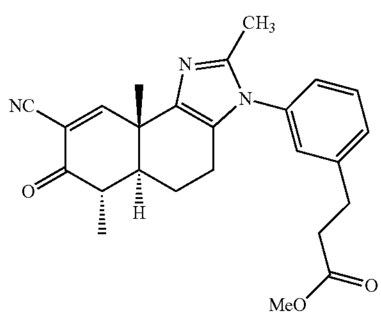 [SMILES: COC(=O)CCc1cccc(-n2c(C)nc3c2CC[C@H]2[C@H](C)C(=O)C(C#N)=C[C@]32C)c1] | 222 |
| T15 | 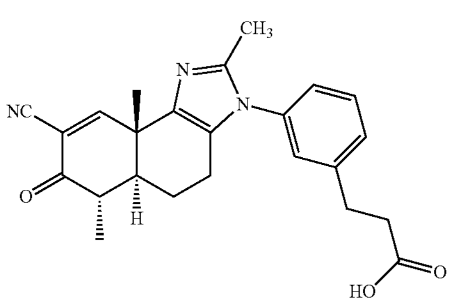 [SMILES: Cc1nc2c(n1-c1cccc(CCC(=O)O)c1)CC[C@H]1[C@H](C)C(=O)C(C#N)=C[C@]21C] | >3000 |

TABLE 1-continued

| Nitric Oxide Inhibition | | |
|---|---|---|
| Compound Number | Structure | NO IC$_{50}$ (nM) |
| T16 | | 132 |
| T17 | | 120 |
| T18 | | 693 |
| T19 | | 82.7 |

TABLE 1-continued

Nitric Oxide Inhibition

| Compound Number | Structure | NO IC$_{50}$ (nM) |
|---|---|---|
| T20 | 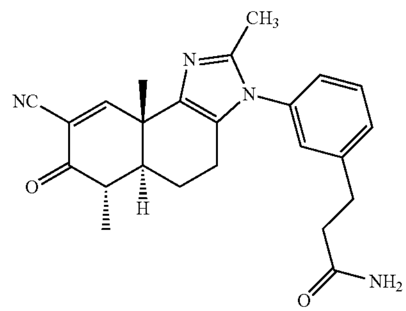 [SMILES: Cc1nc2c(n1-c1cccc(CCC(N)=O)c1)CC[C@H]1[C@H](C)C(=O)C(C#N)=C[C@]21C] | 1000 |
| T21 | 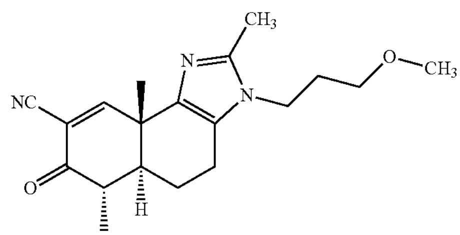 [SMILES: COCCCn1c(C)nc2c1CC[C@H]1[C@H](C)C(=O)C(C#N)=C[C@]21C] | 407 |
| T22 | 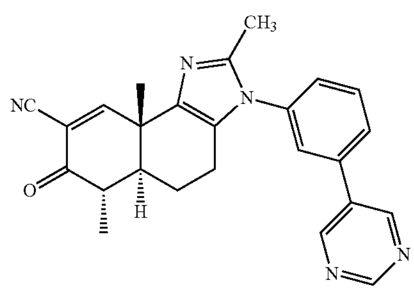 [SMILES: Cc1nc2c(n1-c1cccc(-c3cncnc3)c1)CC[C@H]1[C@H](C)C(=O)C(C#N)=C[C@]21C] | 47.8 |
| T23 | 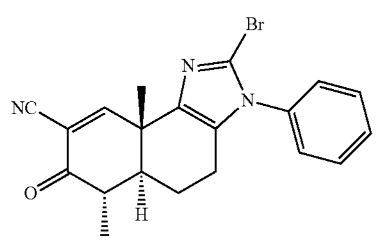 [SMILES: C[C@@H]1C(=O)C(C#N)=C[C@]2(C)c3nc(Br)n(-c4ccccc4)c3CC[C@@H]12] | 31.1 |
| T24 | 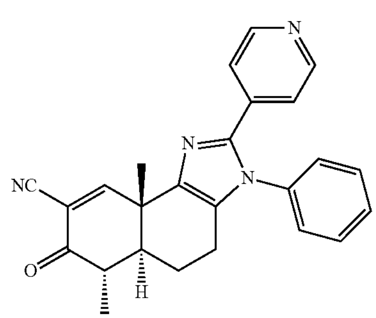 [SMILES: C[C@@H]1C(=O)C(C#N)=C[C@]2(C)c3nc(-c4ccncc4)n(-c4ccccc4)c3CC[C@@H]12] | 48.8 |

TABLE 1-continued
Nitric Oxide Inhibition
| Compound Number | Structure | NO IC$_{50}$ (nM) |
|---|---|---|
| T25 | 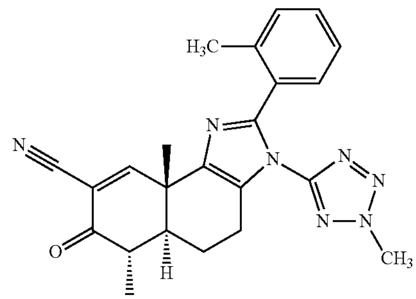 [SMILES: Cc1ccccc1-c1nc2c(n1-c1nnn(C)n1)CC[C@H]1[C@H](C)C(=O)C(C#N)=C[C@]21C] | 15.4 |
| T26 | 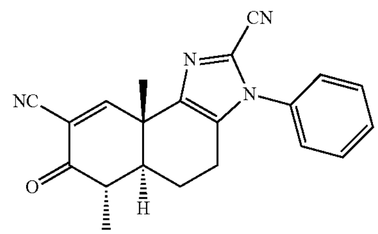 [SMILES: C[C@@H]1C(=O)C(C#N)=C[C@]2(C)c3nc(C#N)n(-c4ccccc4)c3CC[C@@H]12] | 27.7 |
| T27 | 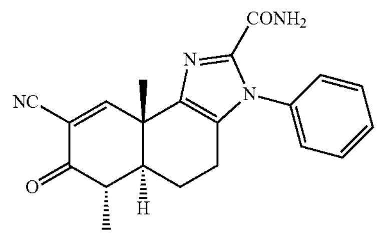 [SMILES: C[C@@H]1C(=O)C(C#N)=C[C@]2(C)c3nc(C(N)=O)n(-c4ccccc4)c3CC[C@@H]12] | 53.1 |
| T28 | 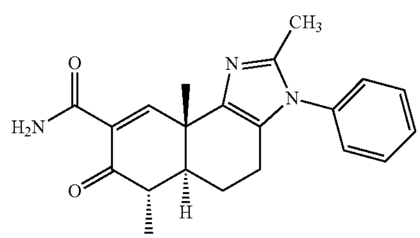 [SMILES: Cc1nc2c(n1-c1ccccc1)CC[C@H]1[C@H](C)C(=O)C(C(N)=O)=C[C@]21C] | 138 |
Example 2: Synthesis and Characterization
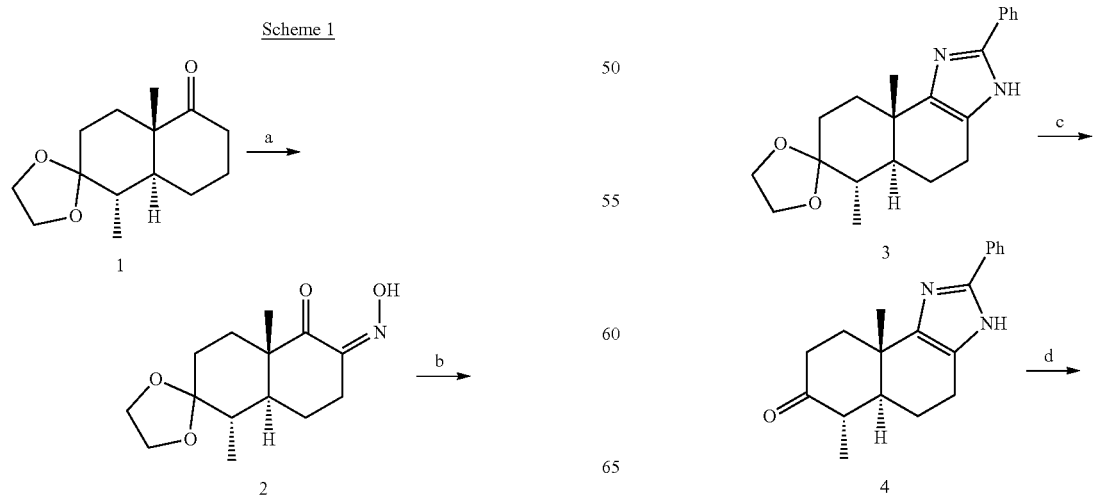
Scheme 1

51 -continued
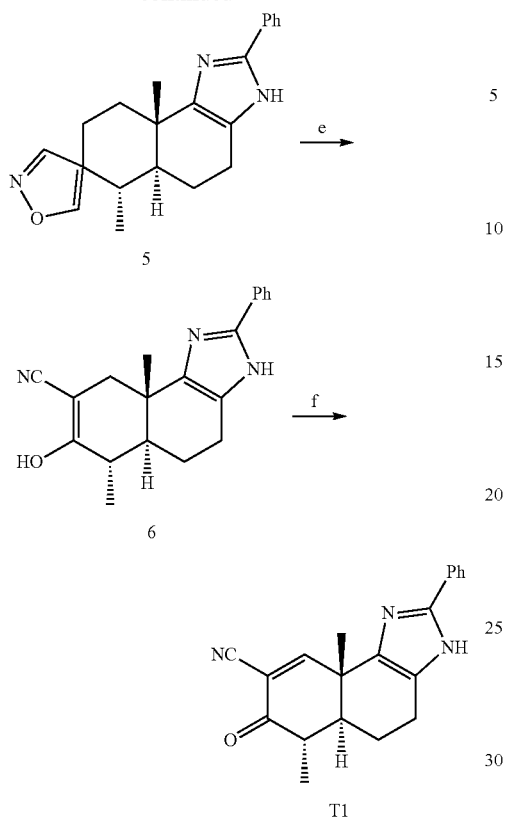
Reagents and conditions: a) t-BuOK, i-amyl nitrite, THF, −30° C. to rt, 59%; b) benzylamine, 150° C., 38%; c) TsOH·H₂O, acetone, water, rt, 100%; d) i) HCO₂Et, NaOMe, MeOH, 0° C. to rt; ii) NH₂OH·HCl, 1 N HCl, 55° C., 69%; e) NaOMe, MeOH, 55° C., 87%; f) i) DBDMH, DMF, 0° C., ii) Py, 55° C., 80%.
Scheme 2
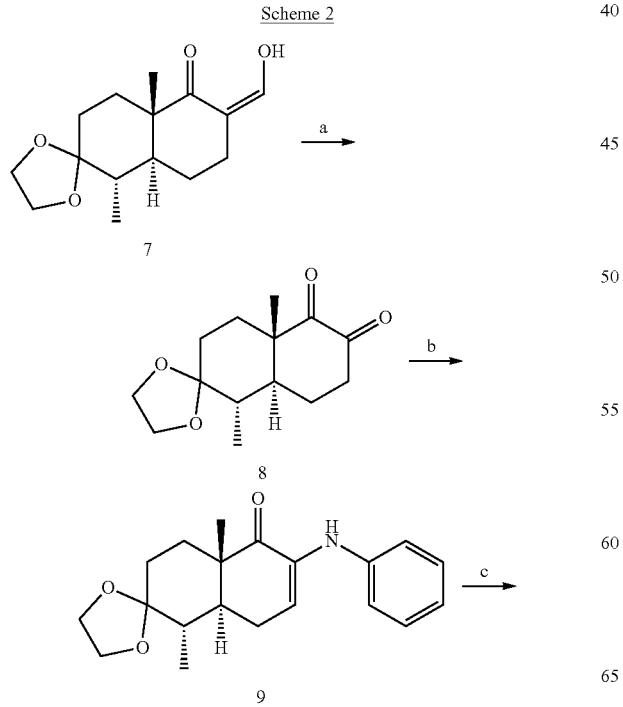
52 -continued
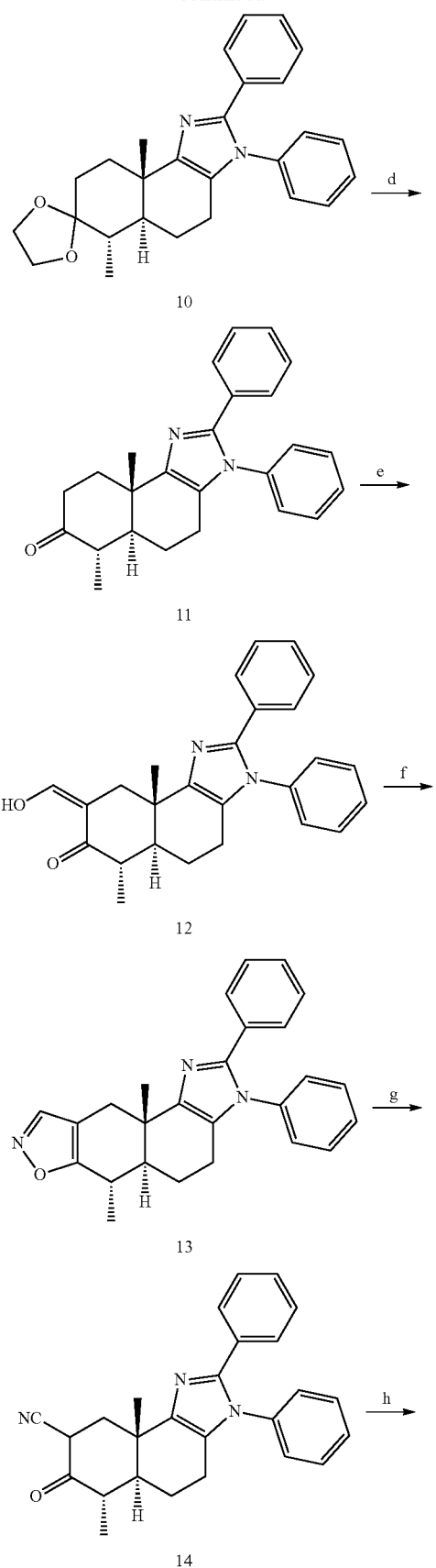

53
-continued

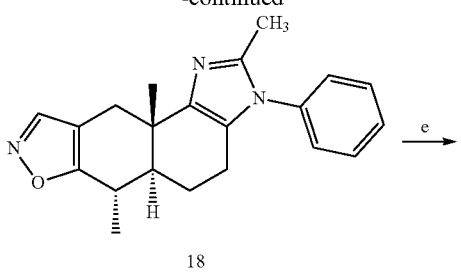

T2

Reagents and conditions: a) i) Ozone, CH₂Cl₂, -78° C.; ii) Me₂S, rt, 16 h, 98%; b) aniline, TsOH•H₂O, benzene, reflux, 60%; c) benzaldehyde, NH₄OAc, EtOH, rt, 85%; d) aq. HCl, THF, rt; e) HCO₂Et, NaOMe, MeOH, rt; f) NH₂OH•HCl, EtOH, 50° C.; g) NaOMe, MeOH, THF, rt, 78% from 10; h) i) Br₂, DMF/CH₂Cl₂, 0° C.; ii) pyridine, 50° C., 30%.

Scheme 3

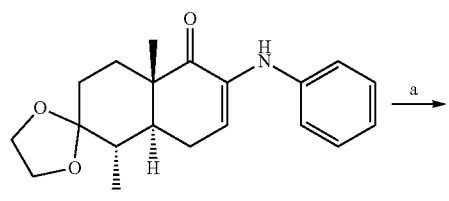

9

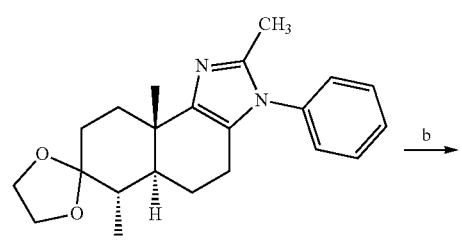

15

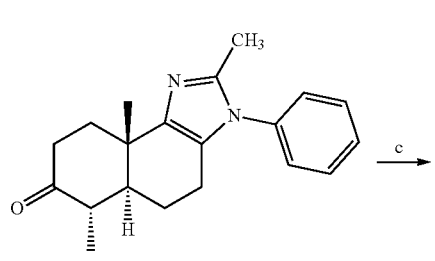

16

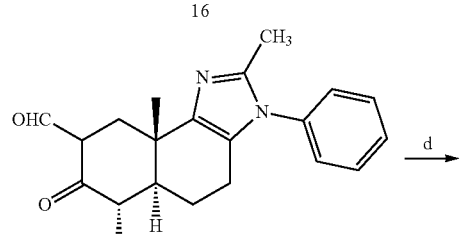

17

54
-continued

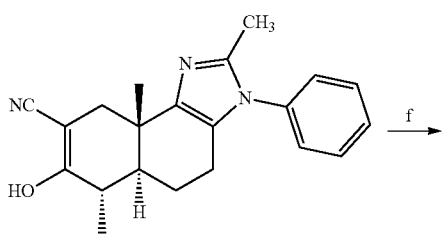

18

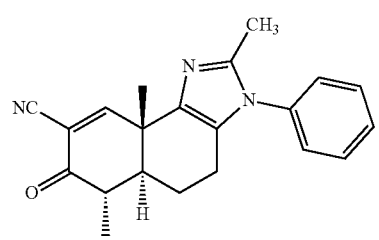

19

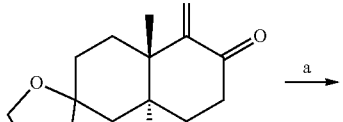

T3

Reagents and conditions: a) NH₄OAc, CH₃CHO, EtOH, rt, 80%: b) aq. HCl, MeOH, rt, 96%; c) HCO₂Et, MeOH, benzene, rt; d) NH₂OH•HCl, EtOH, 50° C. to rt; e) NaOMe, MeOH, rt; f) DBDMH, DMF, 0° C.; ii) pyridine, 50° C., 28% from 16.

Scheme 4

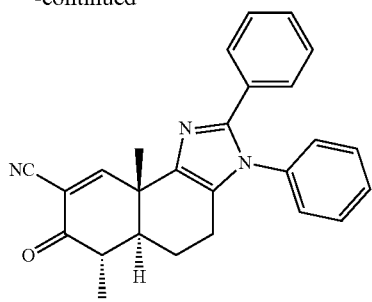

8

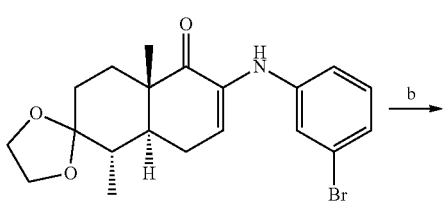

20

-continued
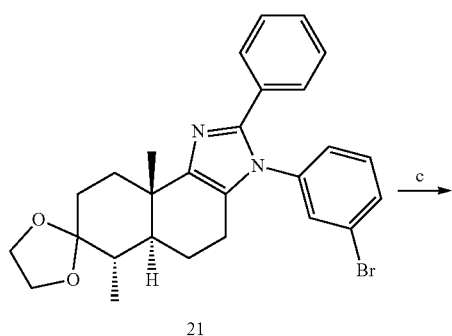
21
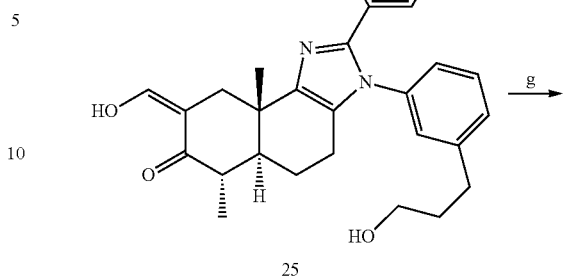
25
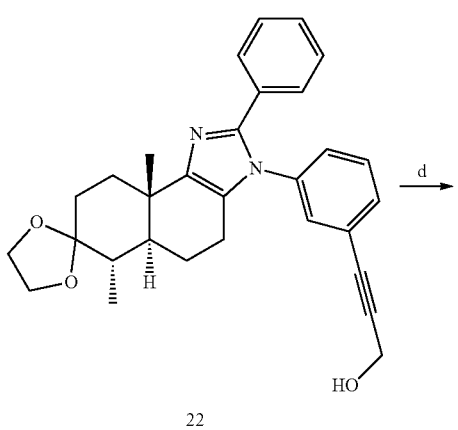
22
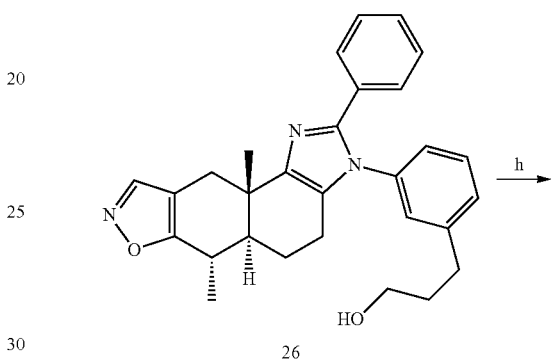
26
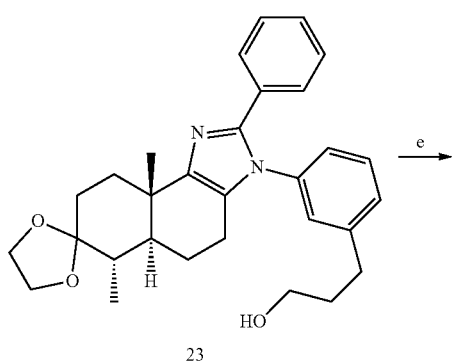
23
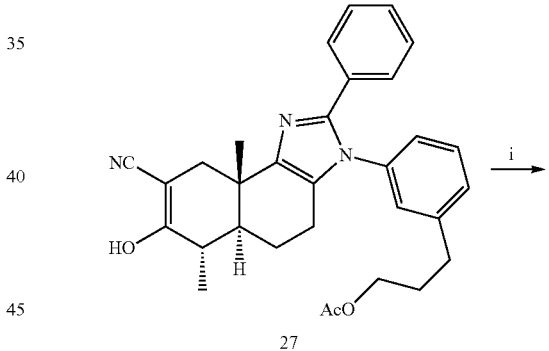
27
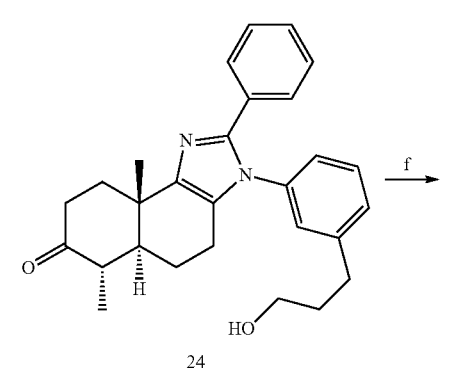
24
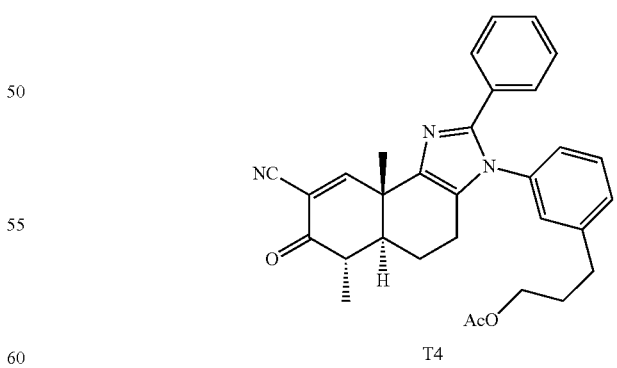
T4
Reagents and conditions: a) 3-bromoaniline, TsOH•H₂O, benzene, reflux, 72%; b) benzaldehyde, NH₄OAc, EtOH, rt to 65° C., 77%; c) CuI, Pd (PPh₃)₂Cl₂, propargyl alchohol, Et₃N, toluene, 80° C., 30%; d) 10% Pd/C, EtOAc, H₂ 1 atm, 67%; e) aq. HCl, THF, rt, 96%; f) HCO₂Et, NaOMe, rt, 96%; g) NH₂OH•HCl, EtOH, 50° C., 96%; h) NaOMe, MeOH, THF, rt, 94%; i) i) Br₂, DMF/CH₂Cl₂, 0° C.; ii) pyridine, 50° C., 15%.

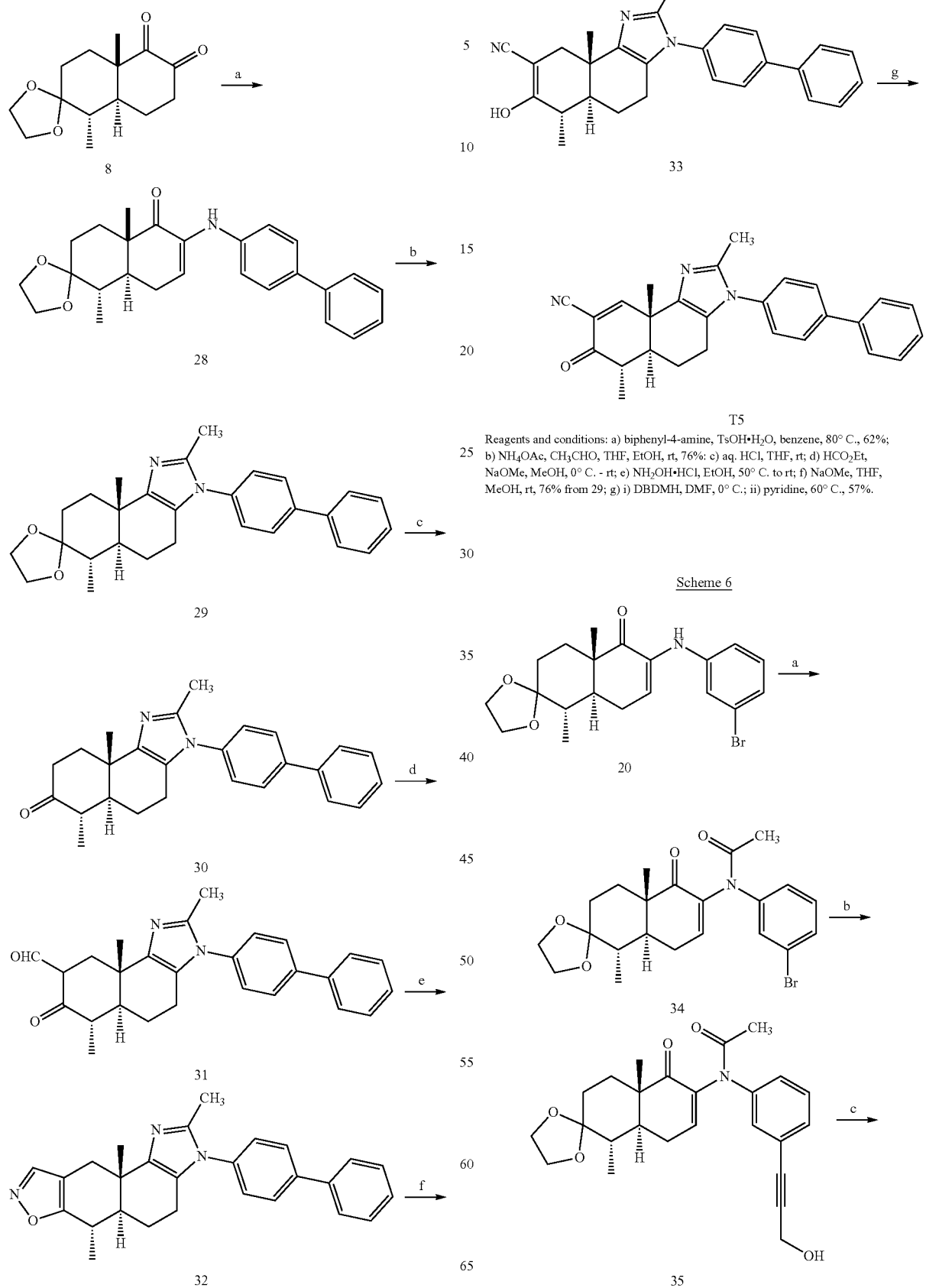
Scheme 5
Reagents and conditions: a) biphenyl-4-amine, TsOH•H₂O, benzene, 80° C., 62%; b) NH₄OAc, CH₃CHO, THF, EtOH, rt, 76%: c) aq. HCl, THF, rt; d) HCO₂Et, NaOMe, MeOH, 0° C. - rt; e) NH₂OH•HCl, EtOH, 50° C. to rt; f) NaOMe, THF, MeOH, rt, 76% from 29; g) i) DBDMH, DMF, 0° C.; ii) pyridine, 60° C., 57%.
Scheme 6

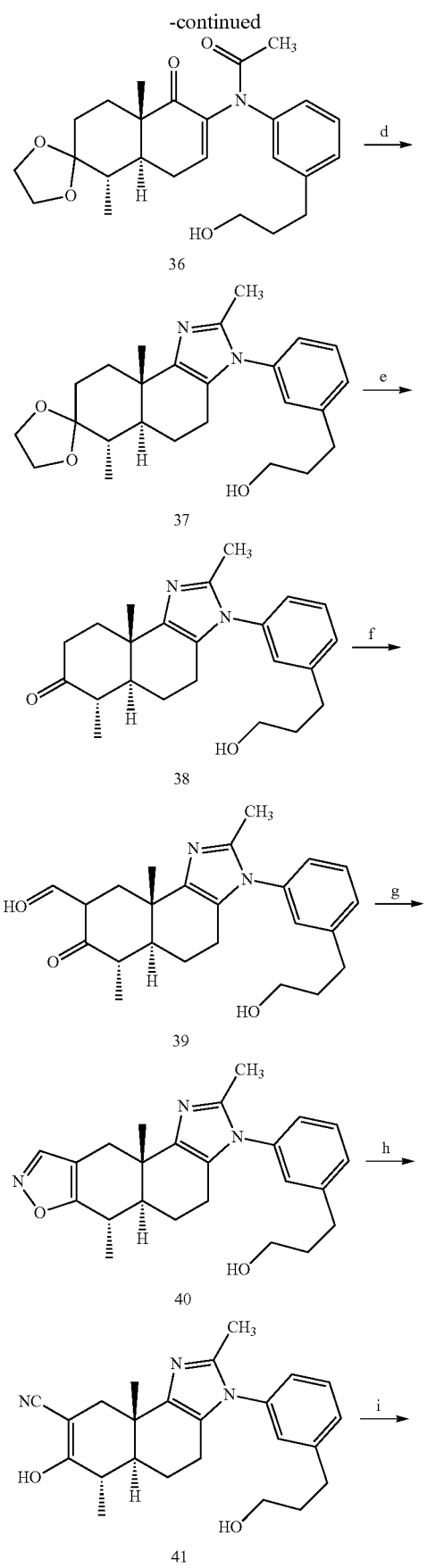
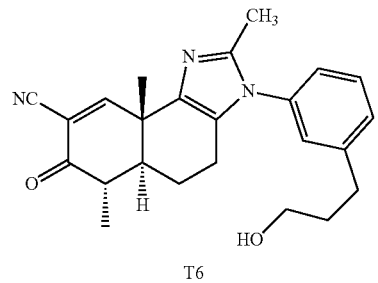
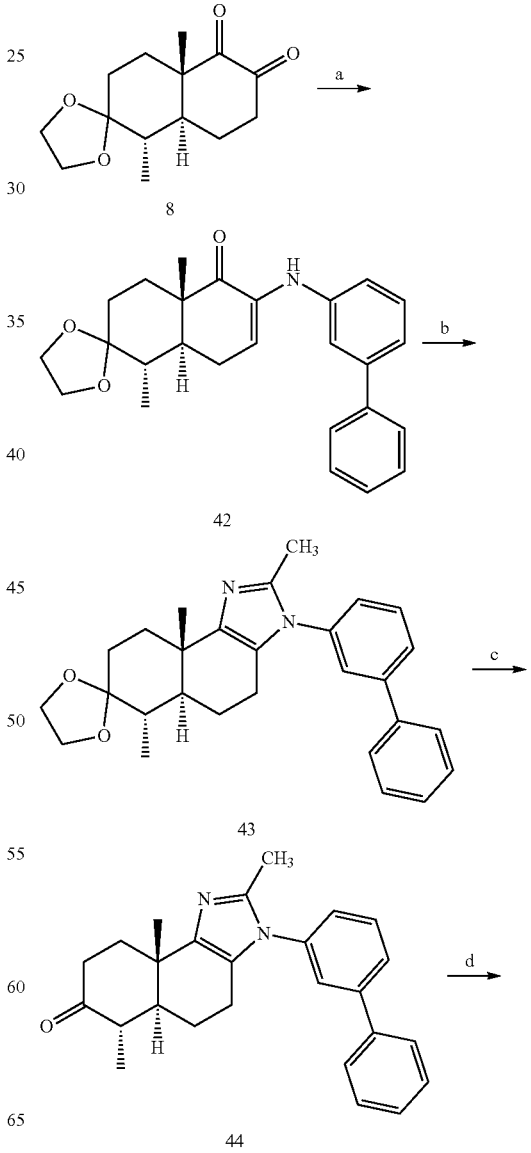
Reagents and conditions: a) acetic anhydride, NaOAc, 140° C., 35%; b) CuI, Pd(PPh₃)₂Cl₂, propargyl alcohol, Et₃N, DME, 80° C., 34%; c) 10% Pd/C, EtOAc, H₂, rt, 1 atm, 90%; d) MeCHO, NH₄OAc, EtOH, 90° C., 39%; e) aq. HCl, THF, rt, 100%; f) HCO₂Et, NaOMe, MeOH, rt, 82%; g) NH₂OH·HCl, EtOH, 50° C., 100%; h) NaOMe, THF, MeOH, rt, 80%; i) Br₂, DMF/CH₂Cl₂, 0° C.; ii) pyridine, 50° C., 25%.
Scheme 7

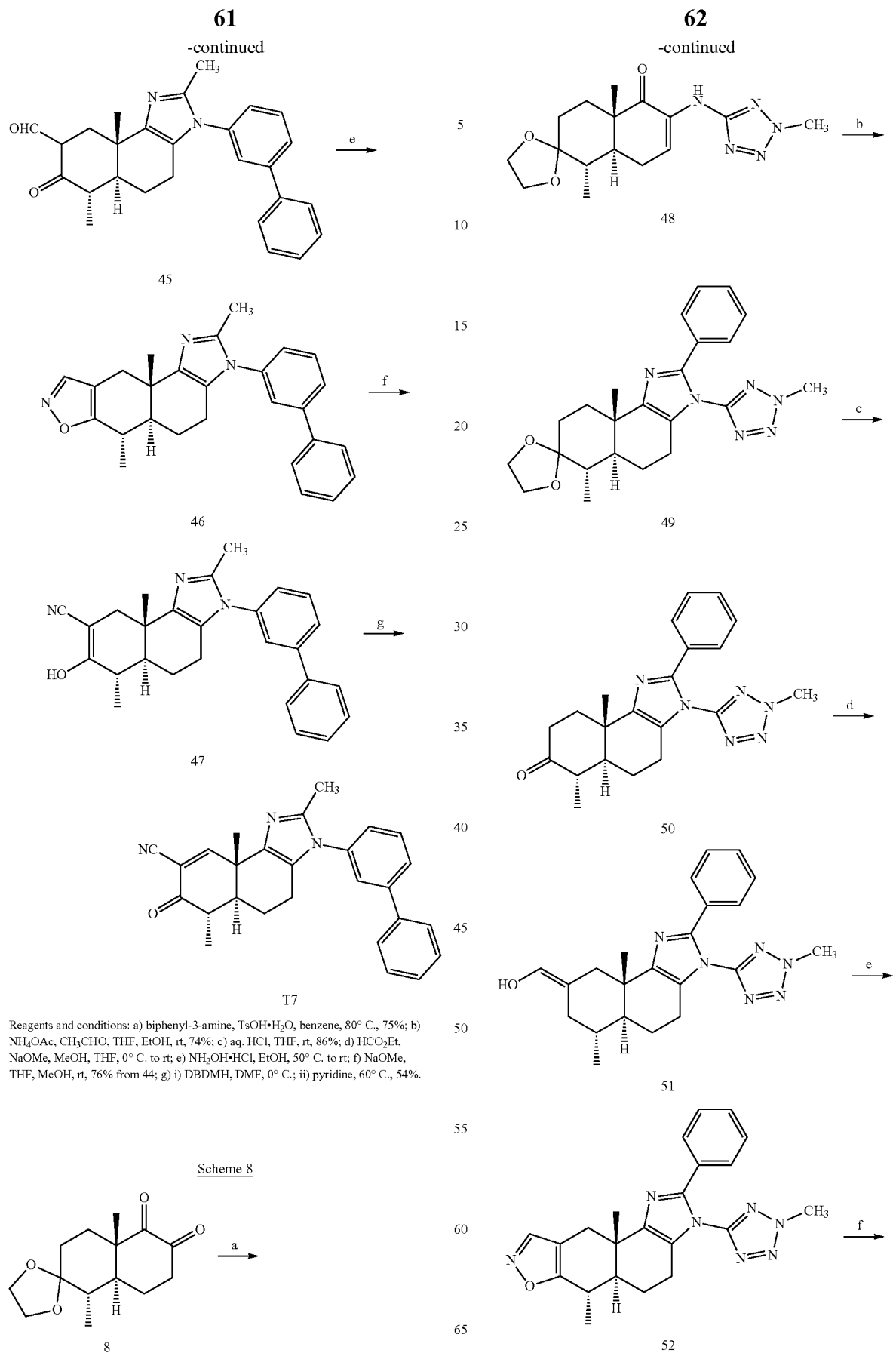
Reagents and conditions: a) biphenyl-3-amine, TsOH•H₂O, benzene, 80° C., 75%; b) NH₄OAc, CH₃CHO, THF, EtOH, rt, 74%; c) aq. HCl, THF, rt, 86%; d) HCO₂Et, NaOMe, MeOH, THF, 0° C. to rt; e) NH₂OH•HCl, EtOH, 50° C. to rt; f) NaOMe, THF, MeOH, rt, 76% from 44; g) i) DBDMH, DMF, 0° C.; ii) pyridine, 60° C., 54%.
Scheme 8

63

-continued

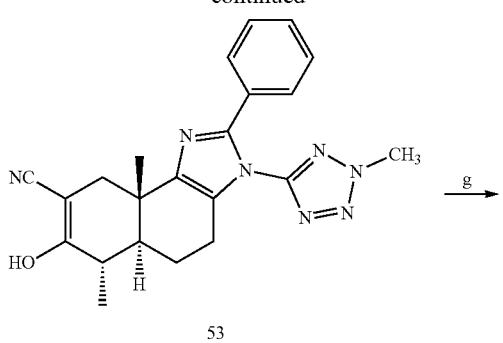

53

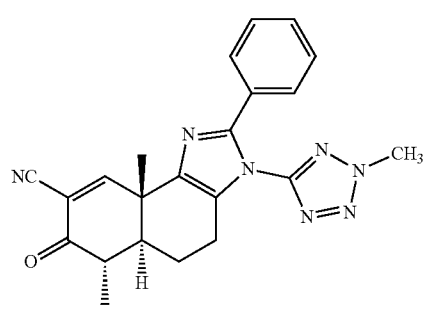

T8

Reagents and conditions: a) 2-methyl-2H-tetrazol-5-amine, TsOH•H₂O, benzene, reflux, 63%; b) benzaldehyde, NH₄OAc, EtOH, rt to 50° C., 90%; c) aq. HCl, THF, rt; d) HCO₂Et, NaOMe, MeOH, rt; e) NH₂OH•HCl, EtOH, 50° C.; f) NaOMe, MeOH, THF, rt, 79% from 49; g) i) Br₂, DMF/CH₂Cl₂, 0° C.; ii) pyridine, 50° C., 33%.

Scheme 9

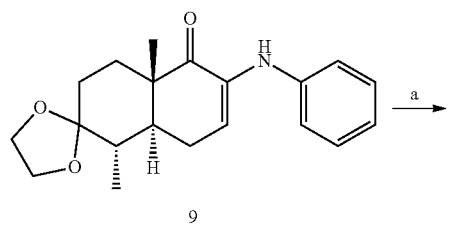

9

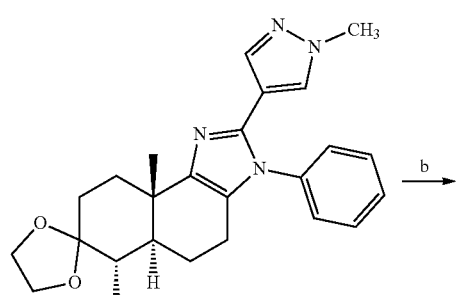

54

64

-continued

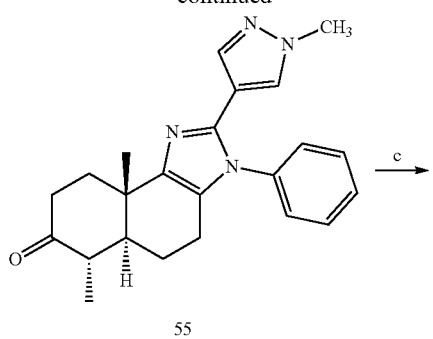

55

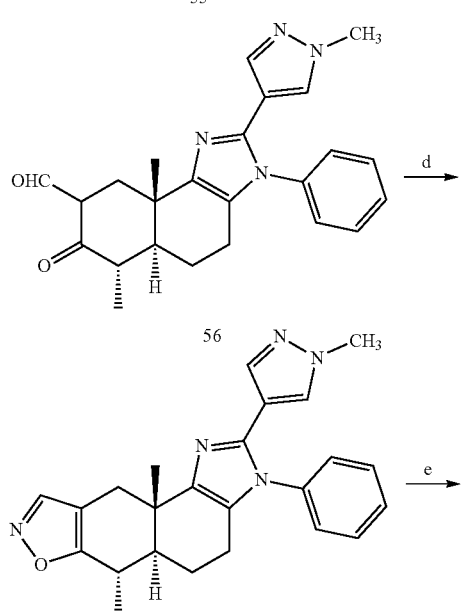

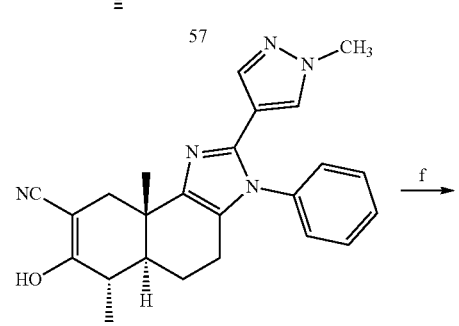

58

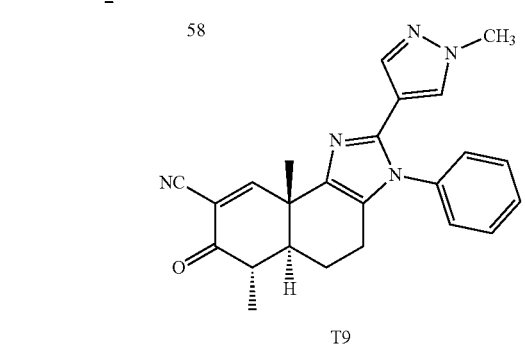

T9

Reagents and conditions: a) NH₄OAc, 1-methyl-1H-pyrazole-4-carbaldehyde, EtOH, rt, 87%; b) aq. HCl, THF, rt, 97%; c) HCO₂Et, NaOMe, MeOH, rt; d) NH₂OH•HCl, EtOH, 50° C. to rt; e) NaOMe, MeOH, THF, rt, 95% from 55; f) i) DBDMH, DMF, 0° C.; ii) pyridine, 60° C., 44%.

Scheme 10
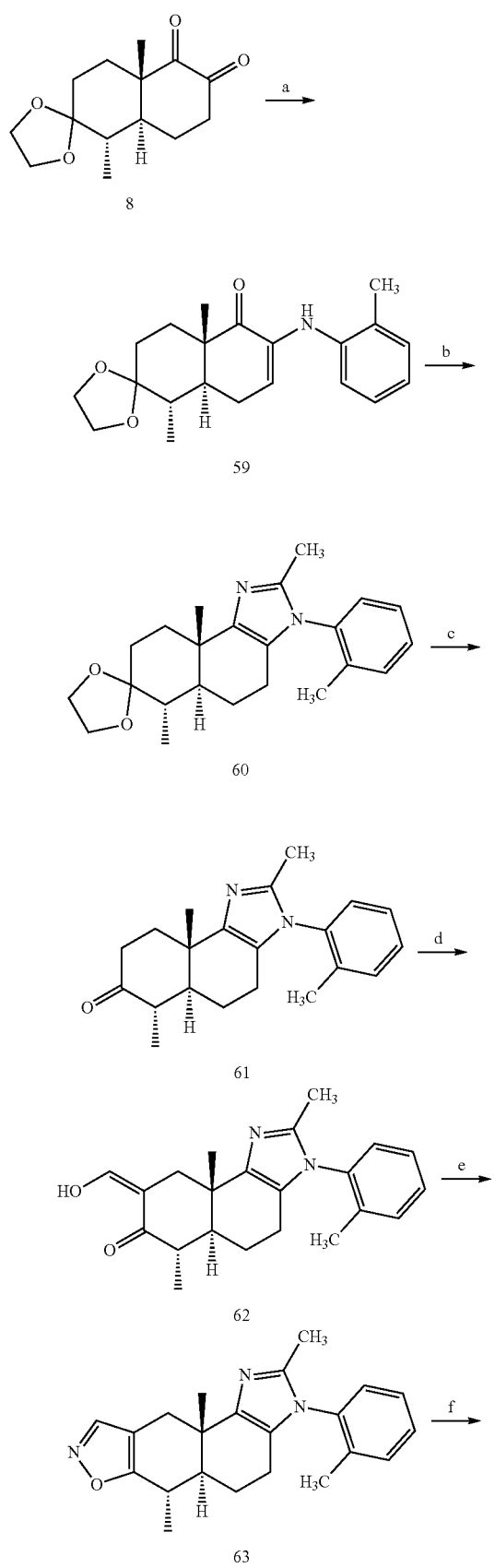
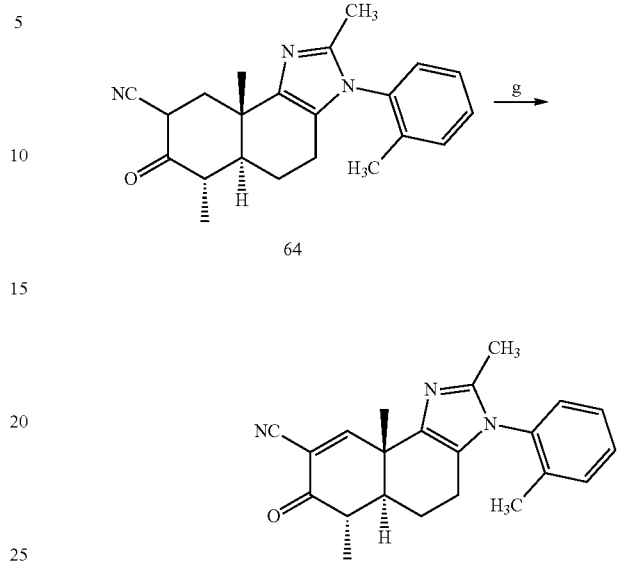
Reagents and conditions: a) 2-methyl-aniline, TsOH•H₂O, benzene, reflux, 53%; b) MeCHO, NH₄OAc, EtOH, rt, 27%; c) aq. HCl, THF, rt; d) HCO₂Et, NaOMe, MeOH, rt; e) NH₂OH•HCl, EtOH, 50° C.; f) NaOMe, MeOH, THF, rt, 86% from 60; g) i) Br₂, DMF/CH₂Cl₂, 0° C.; ii) pyridine, 50° C., 27%.
Scheme 11
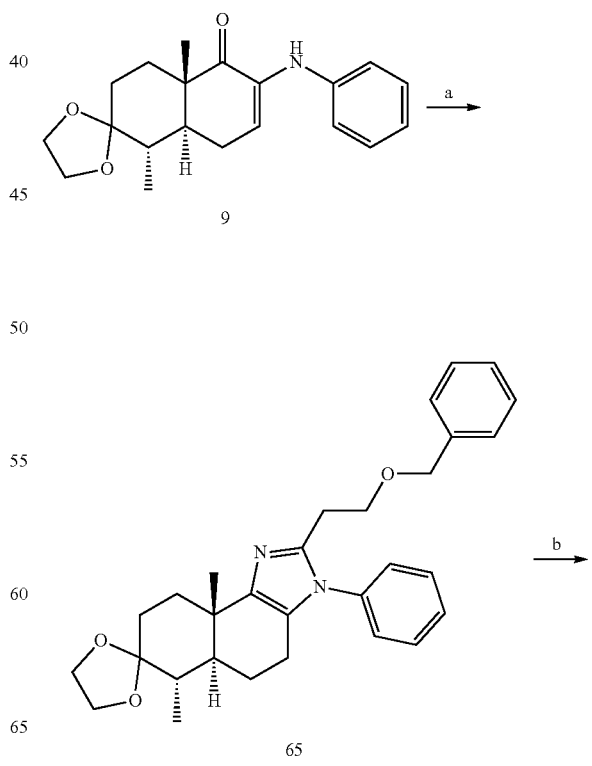

67
-continued
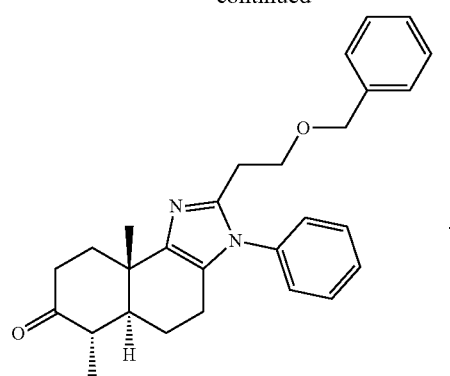
66
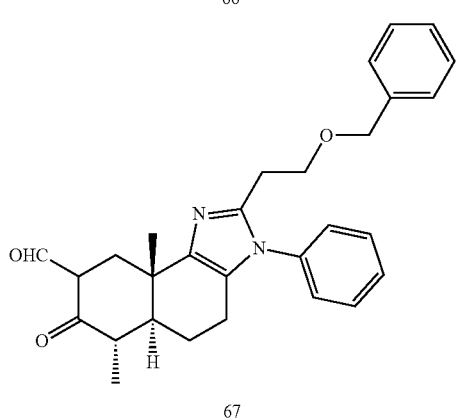
67
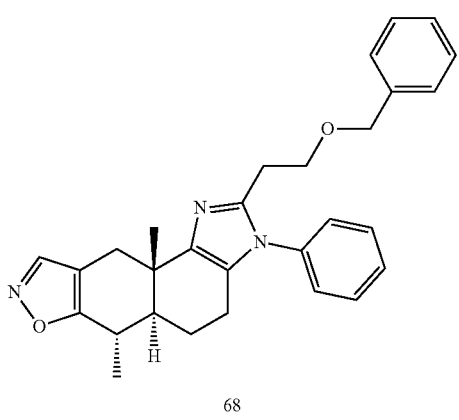
68
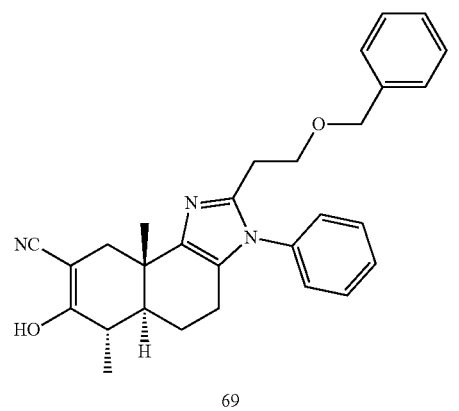
69
68
-continued
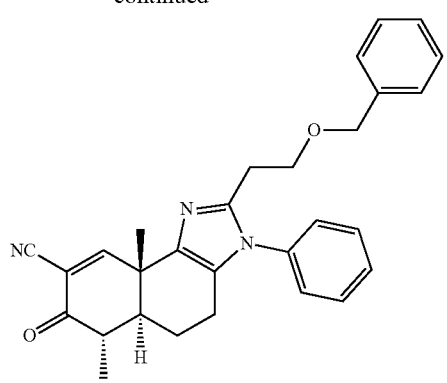
T11
Reagents and conditons: a) NH₄OAc, 3-(benzyloxy)propanol, EtOH, rt to 80° C., 35%; b) aq. HCl, THF, rt, 91%; c) HCO₂Et, NaOMe, MeOH, rt, 99%; d) NH₂OH·HCl, EtOH, 50° C., 95%; e) NaOMe, MeOH, THF, rt, 76%; f) i) DBDMH, DMF, 0° C., ii) pyridine, 60° C., 52%.
Scheme 12
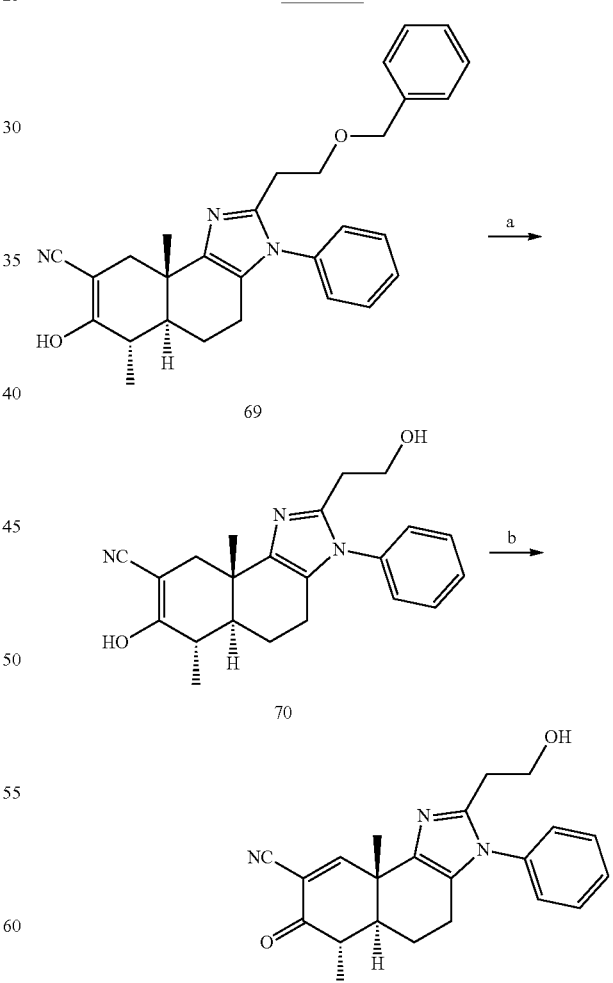
Reagents and conditions: a) H₂, Pd(OH)₂/C, MeOH, rt, 9%; b) i) DBDMH, DMF, 0° C., ii) pyridine, 60° C., 58%.

Scheme 13
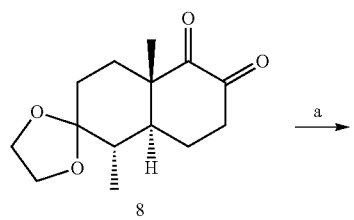
8
a →
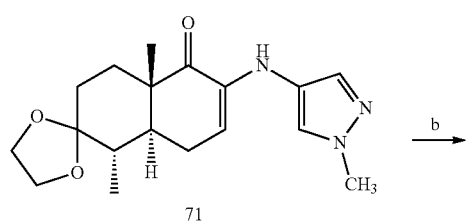
71
b →
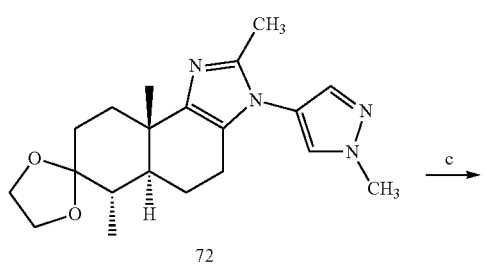
72
c →
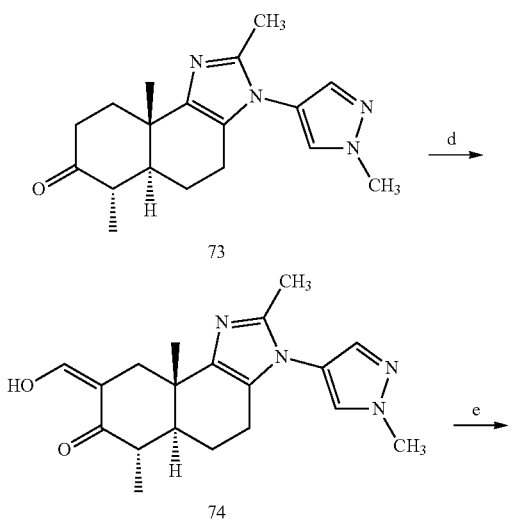
73
d →
74
e →
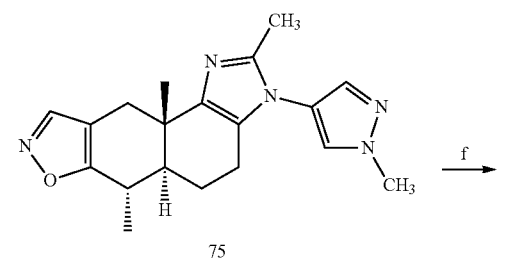
75
f →
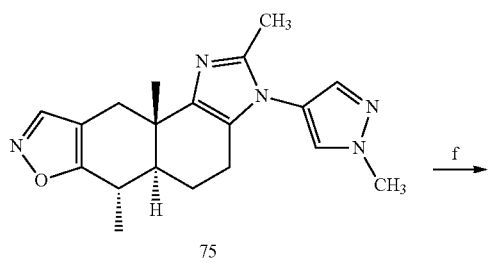
-continued
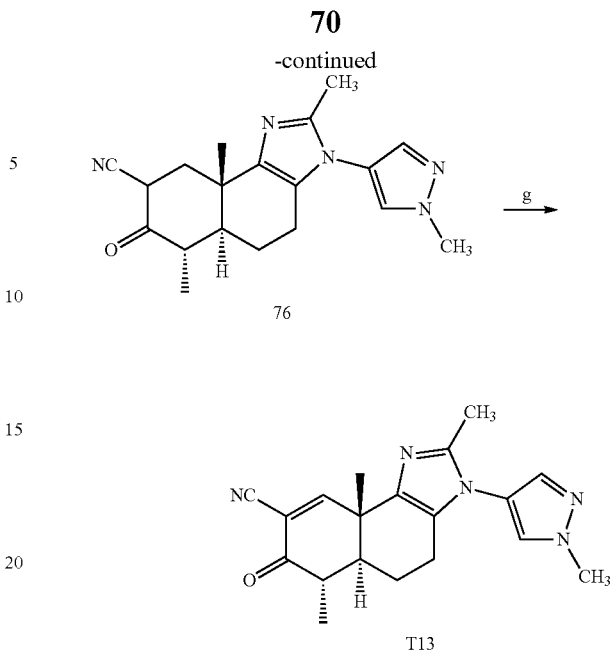
76
g →
T13
Reagents and conditions: a) 1-methyl-1H-pyrazol-4-amine, TsOH•H₂O, benzene, reflux, 79%; b) CH₃CHO, NH₄OAc, EtOH, rt, 93%; c) aq. HCl, THF, rt; d) HCO₂Et, NaOMe, MeOH, rt; e) NH₂OH•HCl, EtOH, 50° C.; f) NaOMe, MeOH, THF, rt, 77% from 72; g) i) Br₂, DMF/CH₂Cl₂ 0° C.; ii) pyridine, 50° C. 36%.
Scheme 14
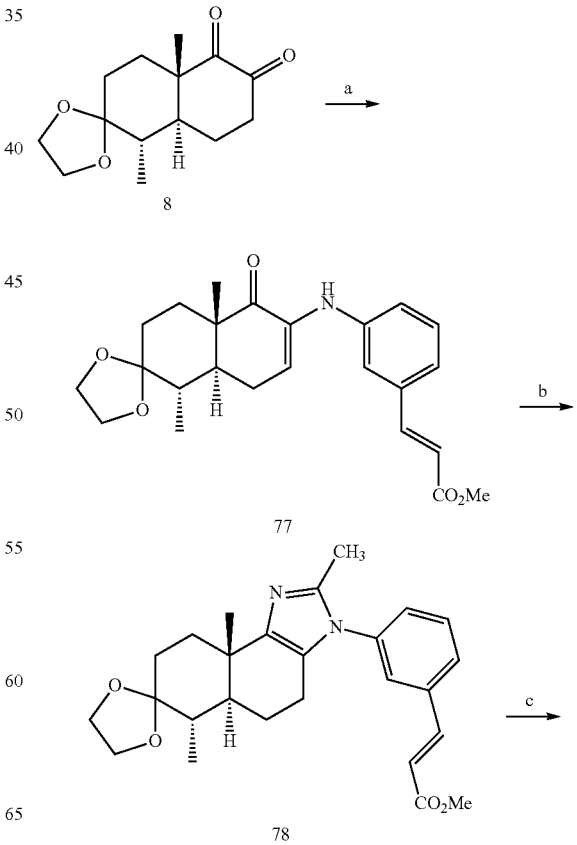
8
a →
77
b →
78
c →

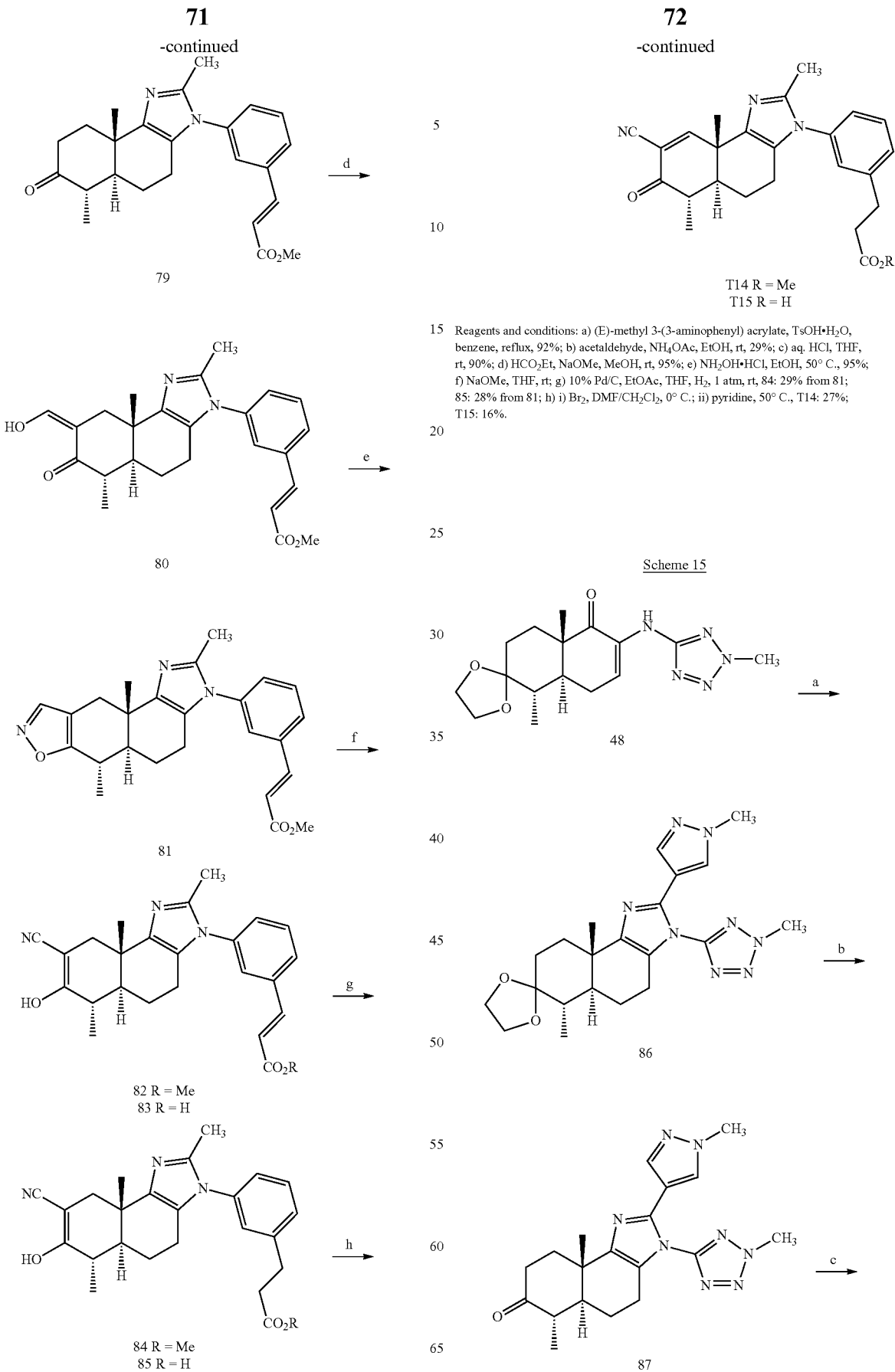
Reagents and conditions: a) (E)-methyl 3-(3-aminophenyl) acrylate, TsOH·H₂O, benzene, reflux, 92%; b) acetaldehyde, NH₄OAc, EtOH, rt, 29%; c) aq. HCl, THF, rt, 90%; d) HCO₂Et, NaOMe, MeOH, rt, 95%; e) NH₂OH·HCl, EtOH, 50° C., 95%; f) NaOMe, THF, rt; g) 10% Pd/C, EtOAc, THF, H₂, 1 atm, rt, 84: 29% from 81; 85: 28% from 81; h) i) Br₂, DMF/CH₂Cl₂, 0° C.; ii) pyridine, 50° C., T14: 27%; T15: 16%.
Scheme 15

73
-continued
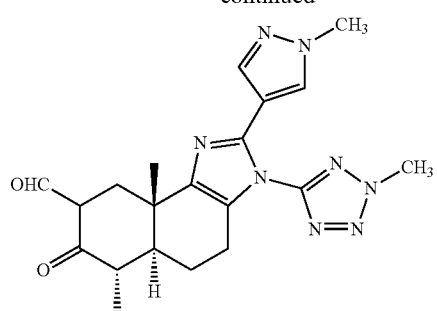
88
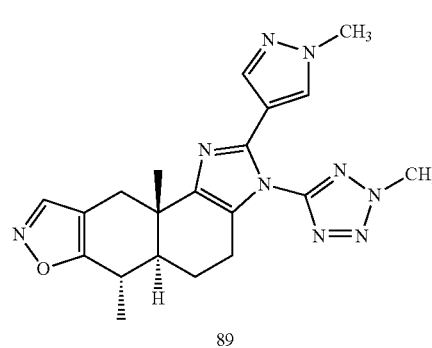
89
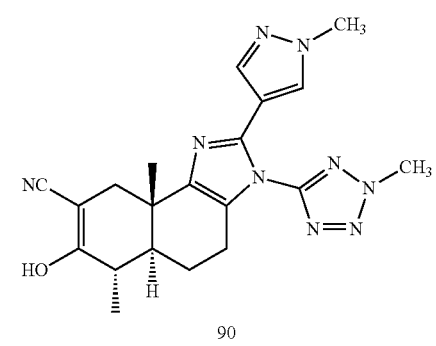
90
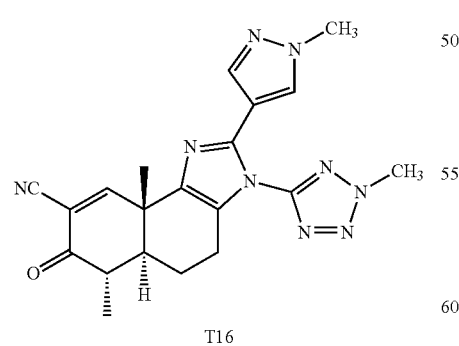
T16
Reagents and conditions: a) 1-methyl-1H-pyrazole-4-carbaldehyde, NH₄OAc, EtOH, THF, rt, 29%; b) aq. HCl, THF, rt, 59%; c) HCO₂Et, NaOMe, MeOH, rt; d) NH₂OH·HCl, EtOH, 50° C., 92% from 87; e) NaOMe, THF, rt, 75%; f) DBDMH, DMF, 0° C.; ii) pyridine, 60° C., 37%.
74
Scheme 16
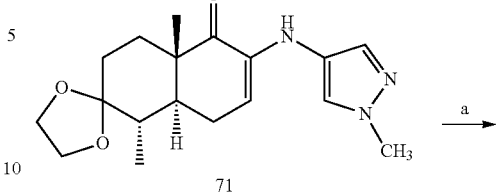
71
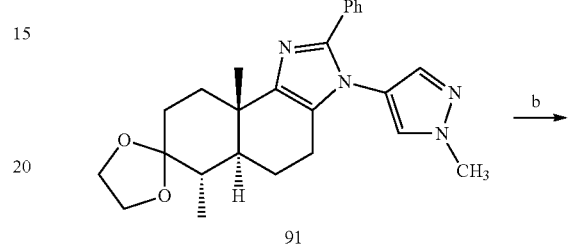
91
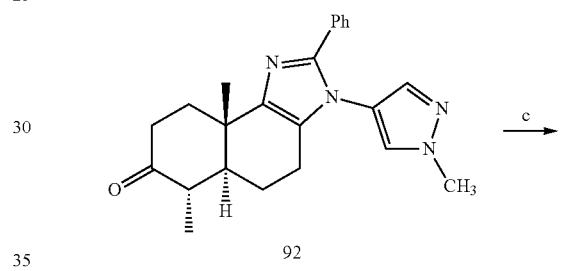
92
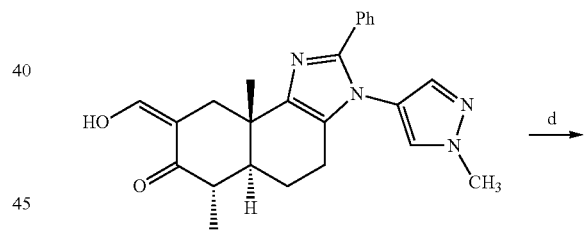
93
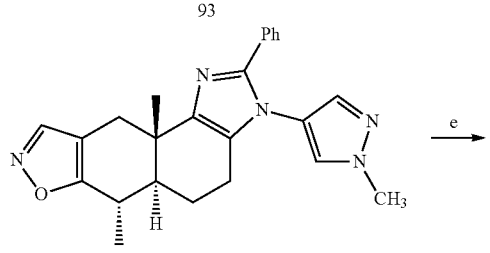
94
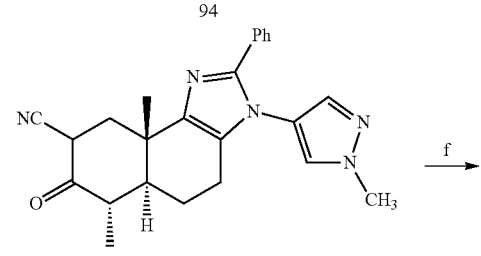
95

75
-continued
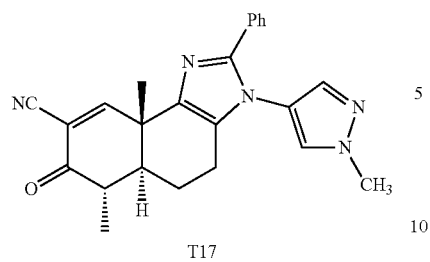
T17
Reagents and conditions: a) benzaldehyde, NH₄OAc, EtOH, rt, 88%; b) aq. HCl, THF, rt; c) HCO₂Et, NaOMe, MeOH, rt; d) NH₂OH·HCl, EtOH, 50° C.; e) NaOMe, THF, rt; f) i) Br₂, DMF/CH₂Cl₂, 0° C.; ii) pyridine, 50° C., 46% from 91.
Scheme 17
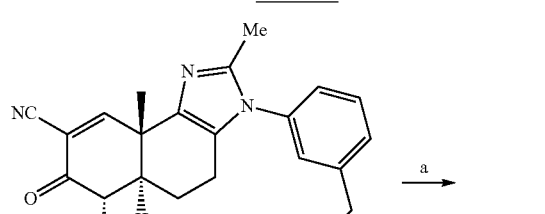
T15
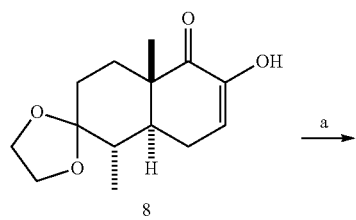
T18: R₁, R₂ = H, Me
T19: R₁, R₂ = Me, Me
T20: R₁, R₂ = H, H
Reagents and conditions: a) i) Oxalyl chloride, CH₂Cl₂, DMF (cat.), 0° C.;
ii) NHRR₁, CH₂Cl₂, 0° C. to rt, T18: 32%; T19: 38%; T20: 10%.
Scheme 18
8
76
-continued
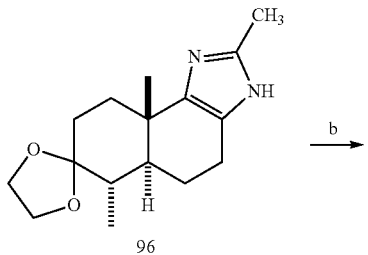
96
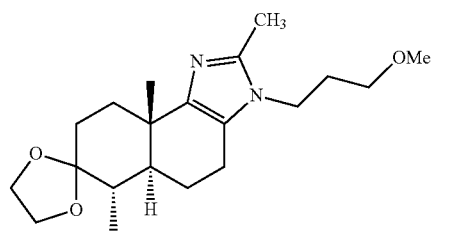
97
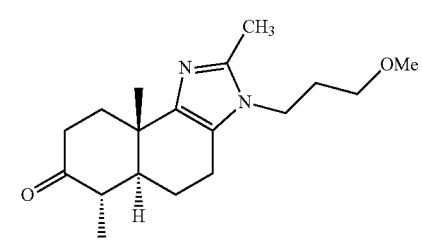
98
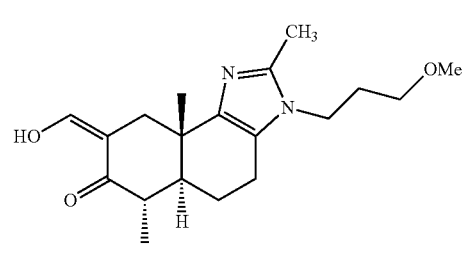
99
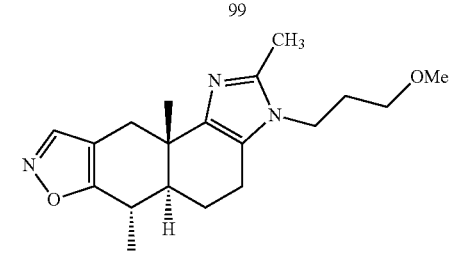
100
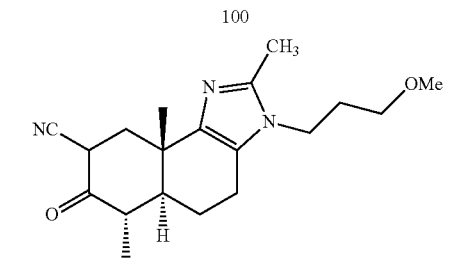
101

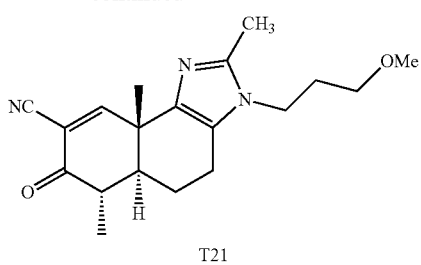

T21

Reagents and conditions: a) NH₄OAc, CH₃CHO, EtOH, rt, 77%; b) Cs₂CO₃, Br(CH₂)₃OMe, MeCN, 85° C., 92%; c) aq. HCl, THF, rt, 79%; d) HCO₂Et, NaOMe, MeOH, rt, 79%; e) NH₂OH·HCl, EtOH, 50° C., 87%; f) NaOMe, MeOH, THF, rt, 93%; g) i) Br₂, DMF/CH₂Cl₂, 0° C.; ii) pyridine, 50° C., 15%.

Scheme 19

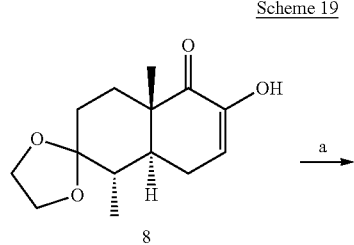

8

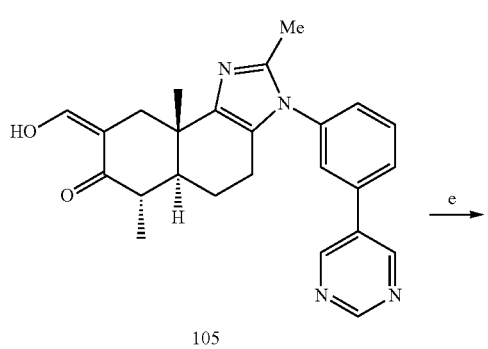

105

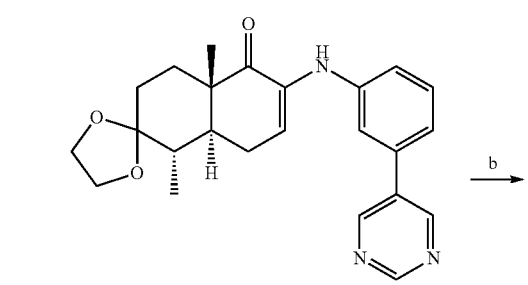

102

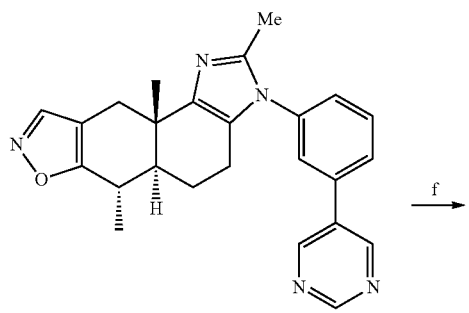

106

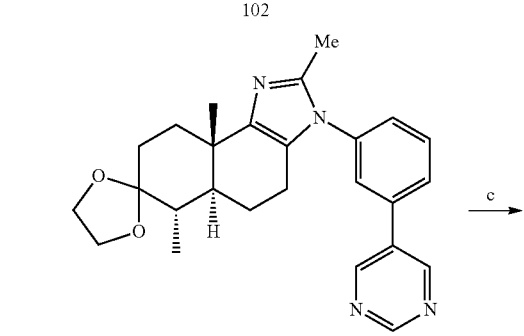

103

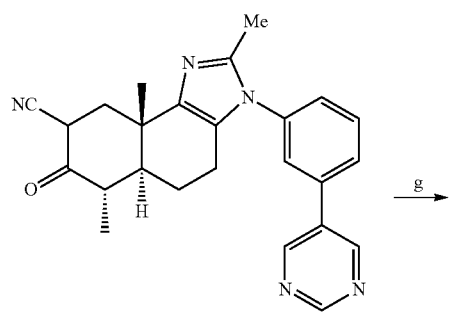

107

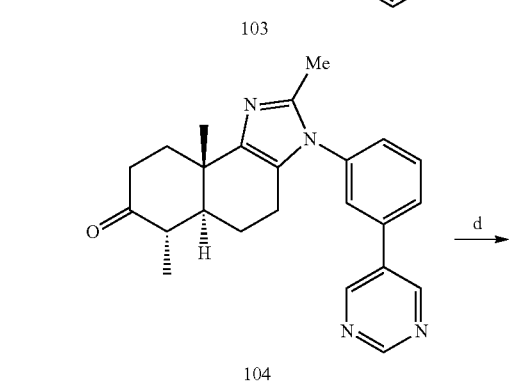

104

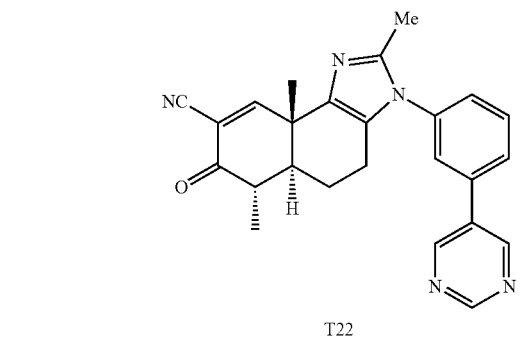

T22

Reagents and conditions: a) 3-pyrimidin-5-ylaniline, p-TsOH·H₂O, benzene, 80° C., 78%; b) NH₄OAc, CH₃CHO, EtOH, THF, rt, 57%: c) aq. HCl, THF, rt, 99%; d) HCO₂Et, NaOMe, MeOH, THF, rt, 98%; e) NH₂OH·HCl, EtOH, 50° C., 65%; f) NaOMe, MeOH, THF, rt, quant; g) i) DBDMH, DMF, 0° C.; ii) pyridine, 60° c., 54%.

Scheme 20
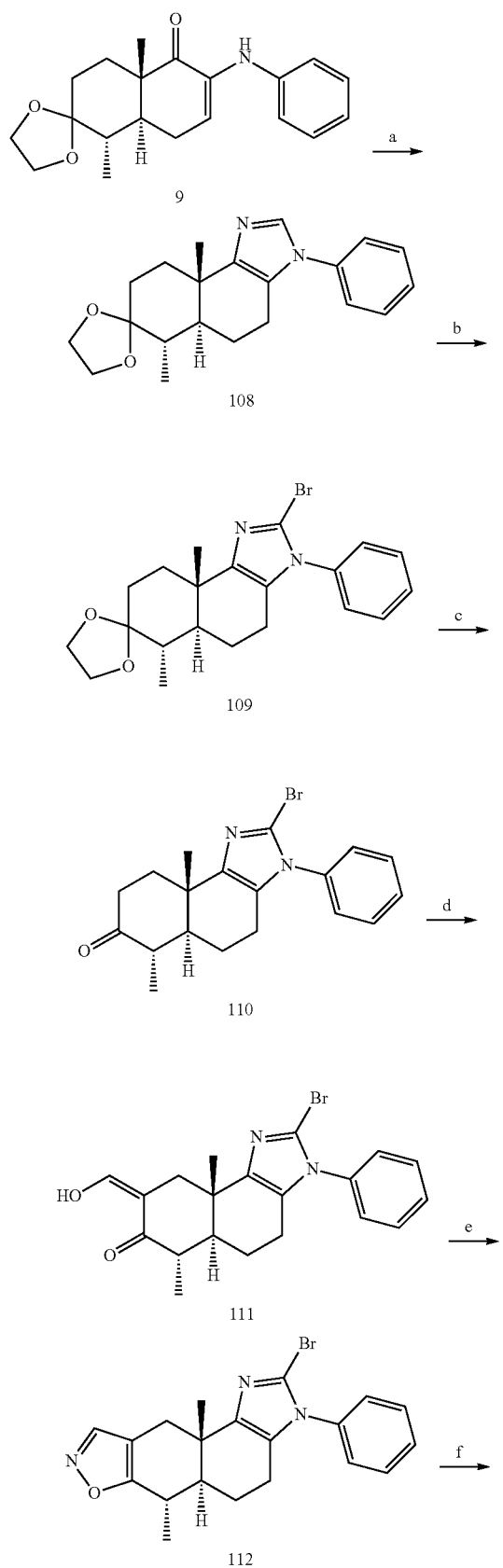
Reagenst and conditions: a) NH₄OAc, aq. HCHO, EtOH, rt, 96%; b) NBS, MeCN, rt, 96%; c) aq. HCl, THF, rt, quant.; d) HCO₂Et, NaOMe, MeOH, rt, 66%; e) NH₂OH·HCl, EtOH, 50° C.; f) NaOMe, MeOH, THF, rt; g) i) Br₂, DMF, CH₂Cl₂, 0° C.; ii) pyridine, 50° C., 33% from 111.
Scheme 21
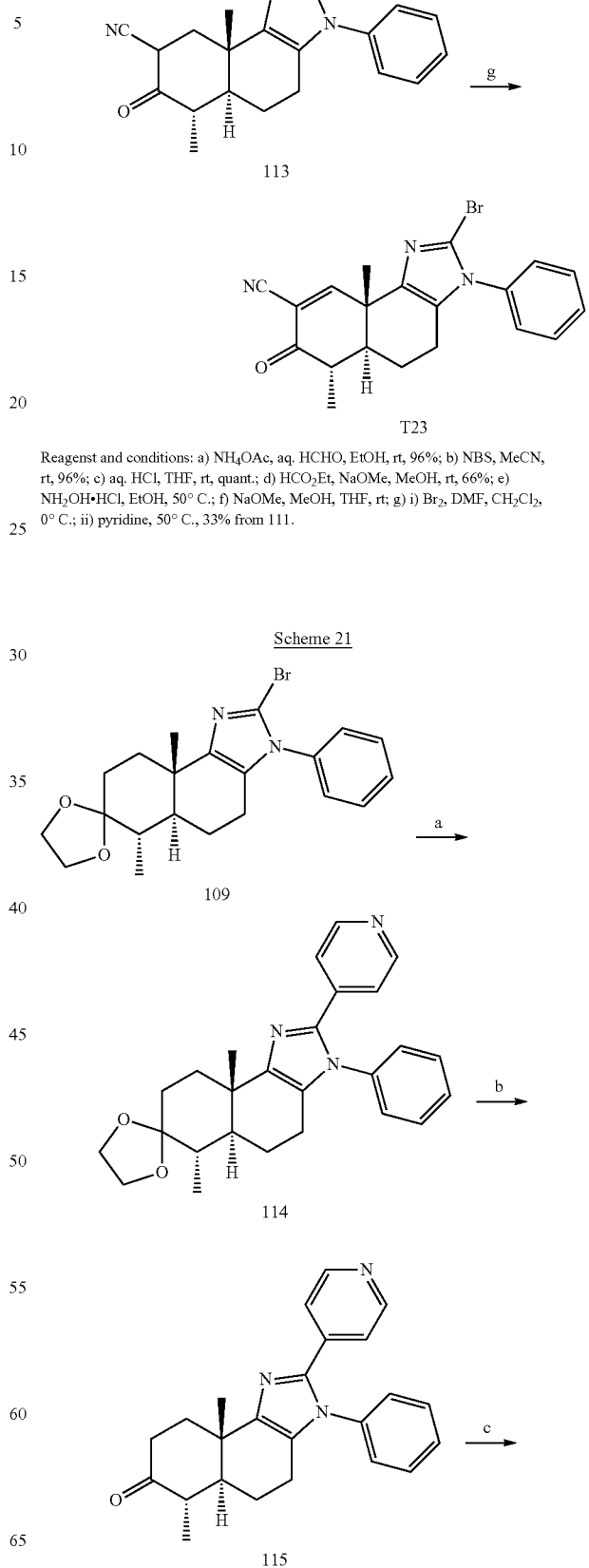

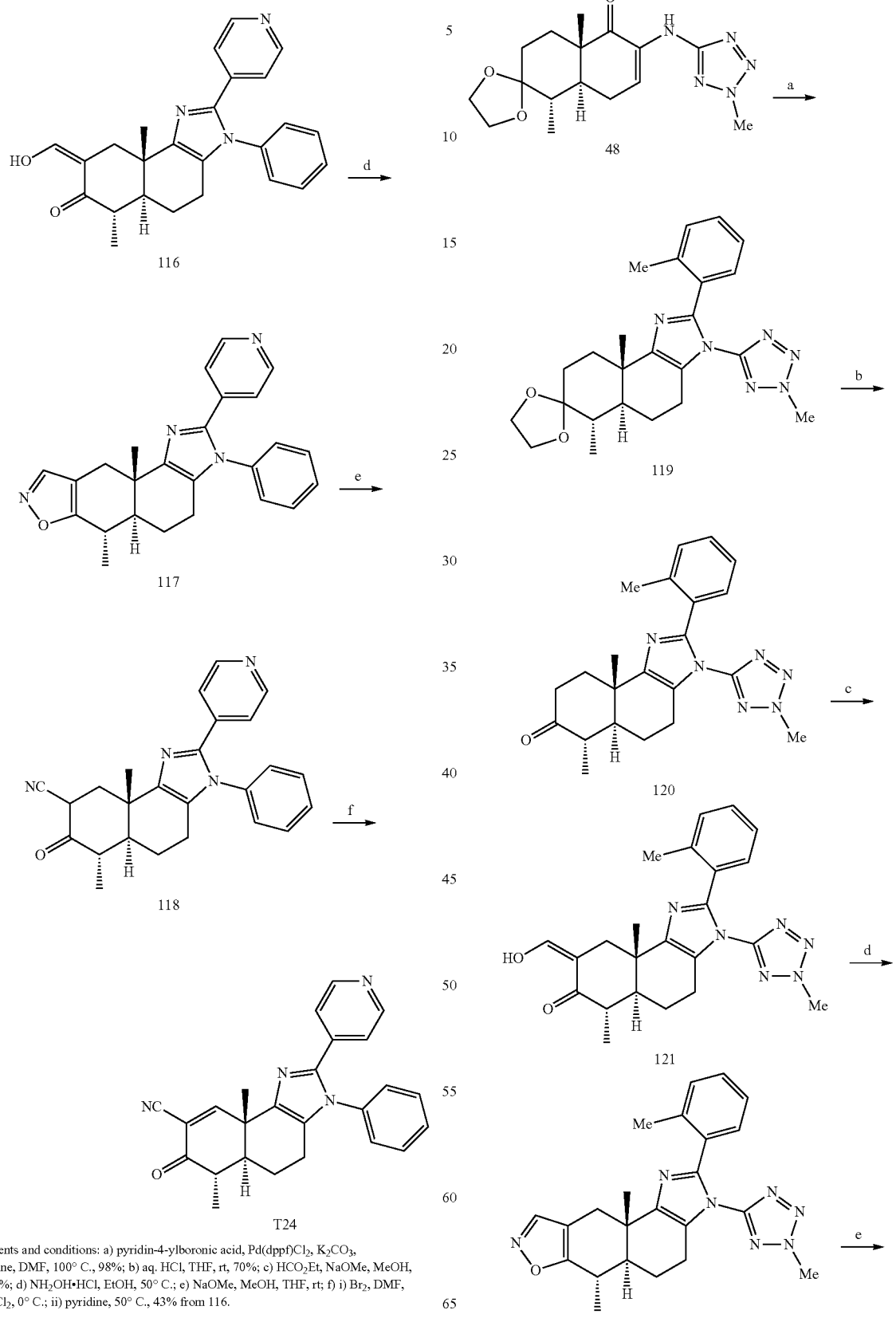
Scheme 22
Reagents and conditions: a) pyridin-4-ylboronic acid, Pd(dppf)Cl$_2$, K$_2$CO$_3$, dioxane, DMF, 100° C., 98%; b) aq. HCl, THF, rt, 70%; c) HCO$_2$Et, NaOMe, MeOH, rt, 94%; d) NH$_2$OH•HCl, EtOH, 50° C.; e) NaOMe, MeOH, THF, rt; f) i) Br$_2$, DMF, CH$_2$Cl$_2$, 0° C.; ii) pyridine, 50° C., 43% from 116.

83
-continued
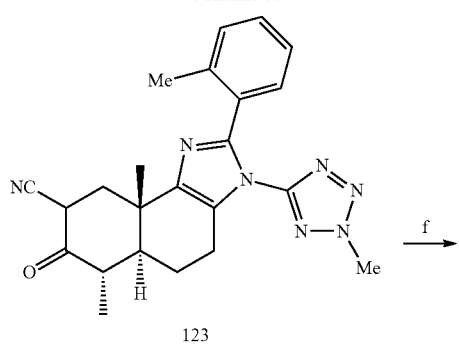
123
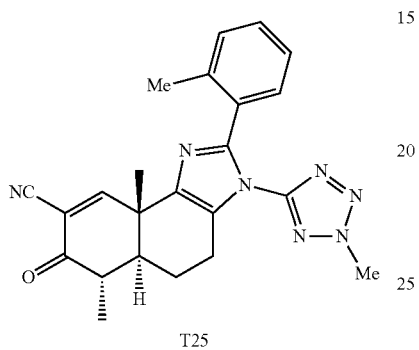
T25
Reagents and conditions: a) NH₄OAc, o-tolualdehyde, THF, EtOH, 80° C., 83%; b) aq. HCl, THF, rt, quant.; c) HCO₂Et, NaOMe, MeOH, THF, rt, 94%; d) NH₂OH·HCl, EtOH, 50° C., 42%; e) NaOMe, MeOH, THF, rt; f) i) DBDMH, DMF, 0° C.; ii) pyridine, 60° C., 42% from 122.
Scheme 23
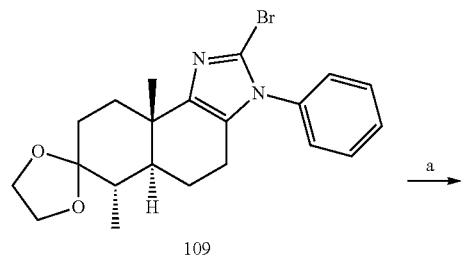
109
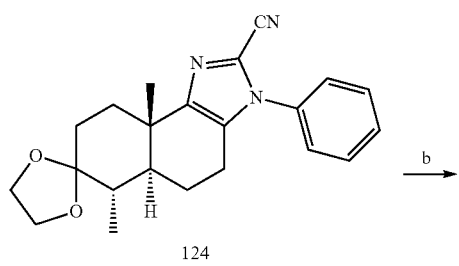
124
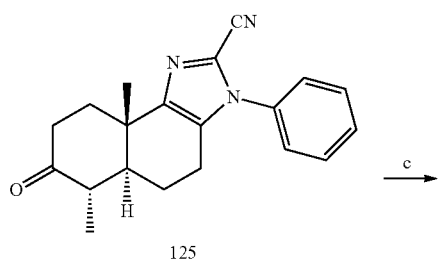
125
84
-continued
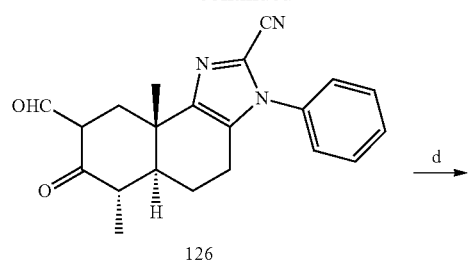
126
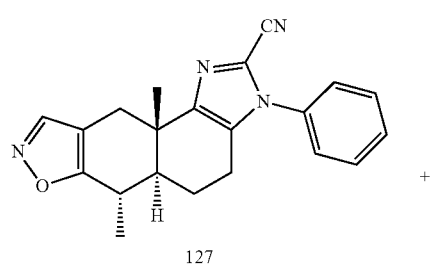
127
+
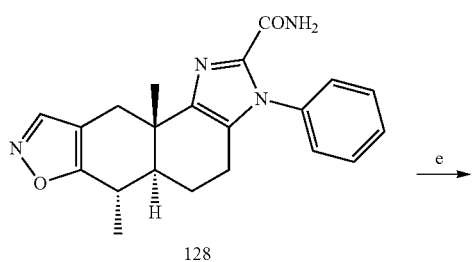
128
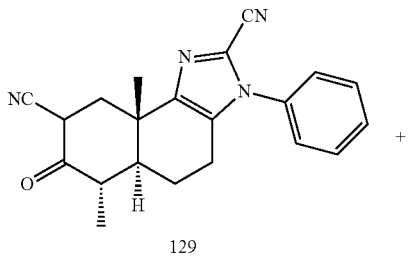
129
+
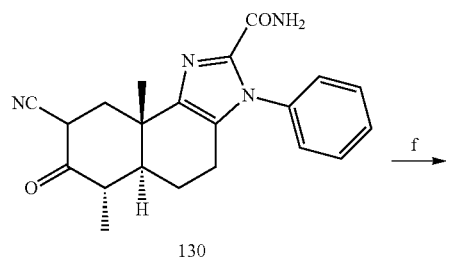
130
T26
+

-continued
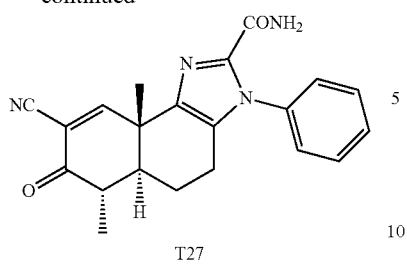
T27
Reagents and conditions: a) Zn(CN)$_2$, Pd$_2$(dba)$_3$, dppf, DMF, 180° C., 88%; b) aq. HCl, THF, MeOH, rt; c) HCO$_2$Et, NaOMe, MeOH, THF, rt; d) NH$_2$OH•HCl, EtOH, 60° C.; e) NaOMe, MeOH, rt; f) DBDMH, DMF, 0° C.; ii) pyridine, 60° C., T26: 16% from 124; T27: 13% from 124.
Scheme 24
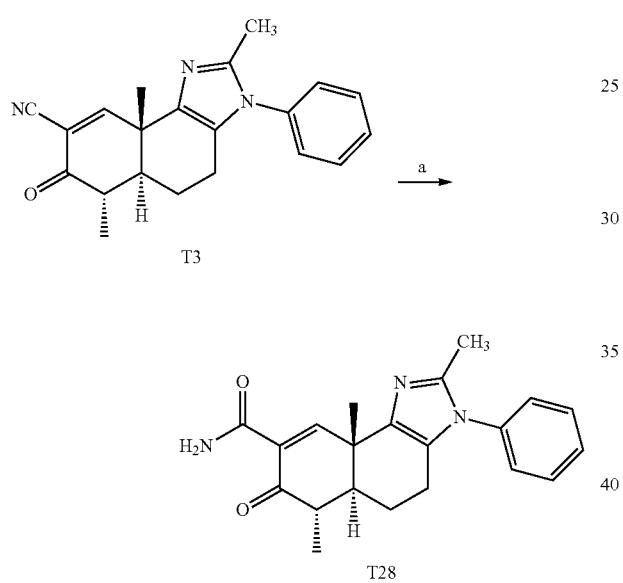
T3
T28
Reagents and conditions: a) hydrido(dimethyl phosphinous acid-kP)[hydrogen bis(dimethylphosphinito-kP)]platinum(II), EtOH, H$_2$O, 90° C., 50%.
Scheme 25 (Proposed)
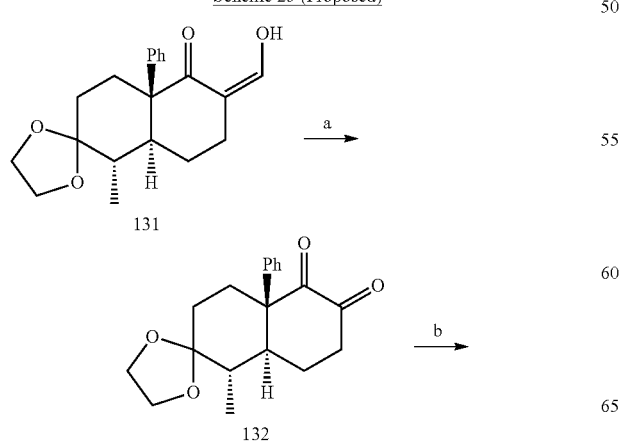
131
132
-continued
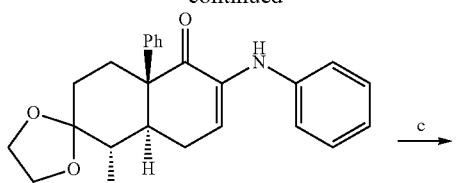
133
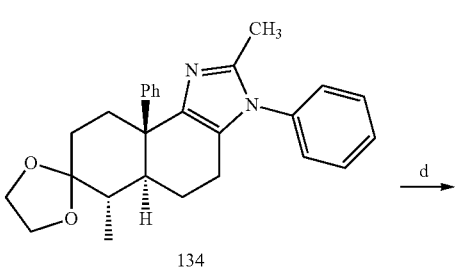
134
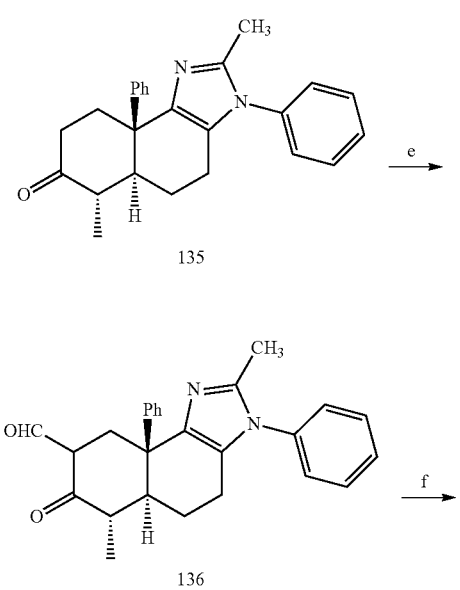
135
136
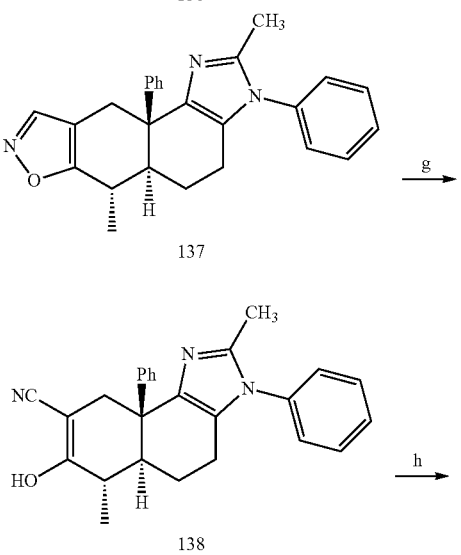
137
138

87
-continued
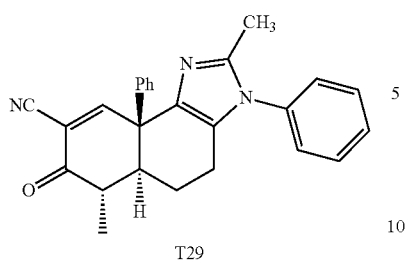
T29
Reagents and conditions: a) i) Ozone; ii) Me₂S; b) aniline, TsOH•H₂O; c) NH₄OAc, CH₃CHO; d) aq. HCl; e) HCO₂Et, NaOMe; f) NH₂OH•HCl; g) NaOMe; h) i) DBDMH; ii) pyridine.
Scheme 26 (Proposed)
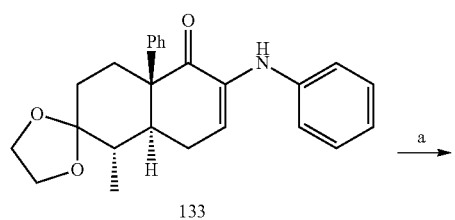
133
a →
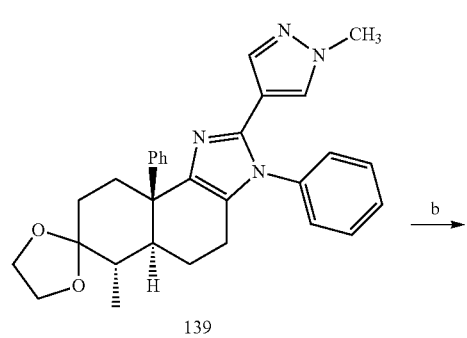
139
b →
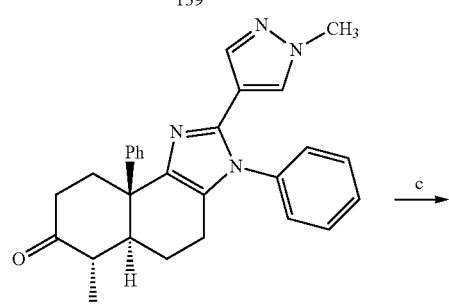
140
c →
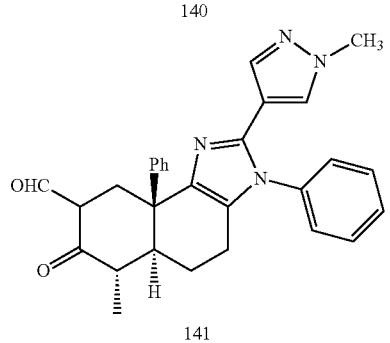
141
d →
88
-continued
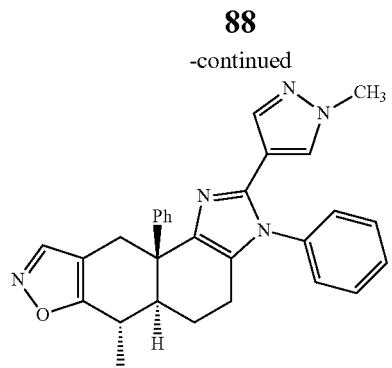
142
e →
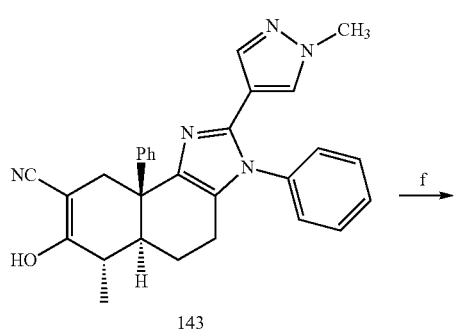
143
f →
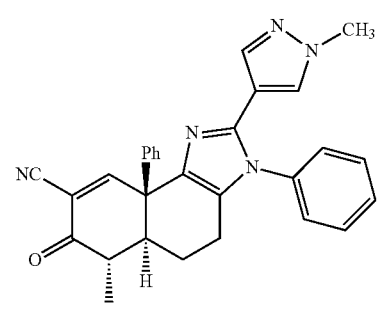
T30
Reagents and conditions: a) NH₄OAc, 1-methyl-1H-pyrazole-4-carbaldehyde; b) aq. HCl; c) HCO₂Et, NaOMe; d) NH₂OH•HCl; e) NaOMe; f) i) DBDMH; ii) pyridine.
Scheme 27 (Proposed)
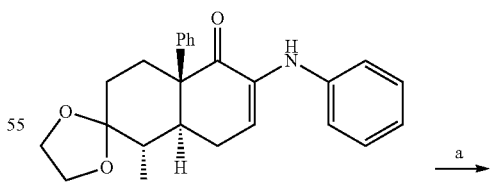
133
a →
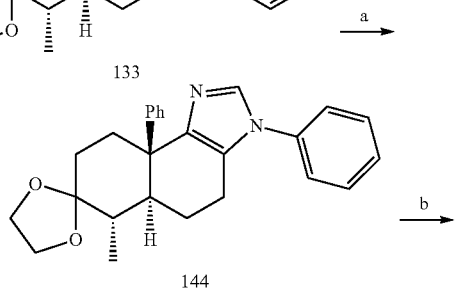
144
b →

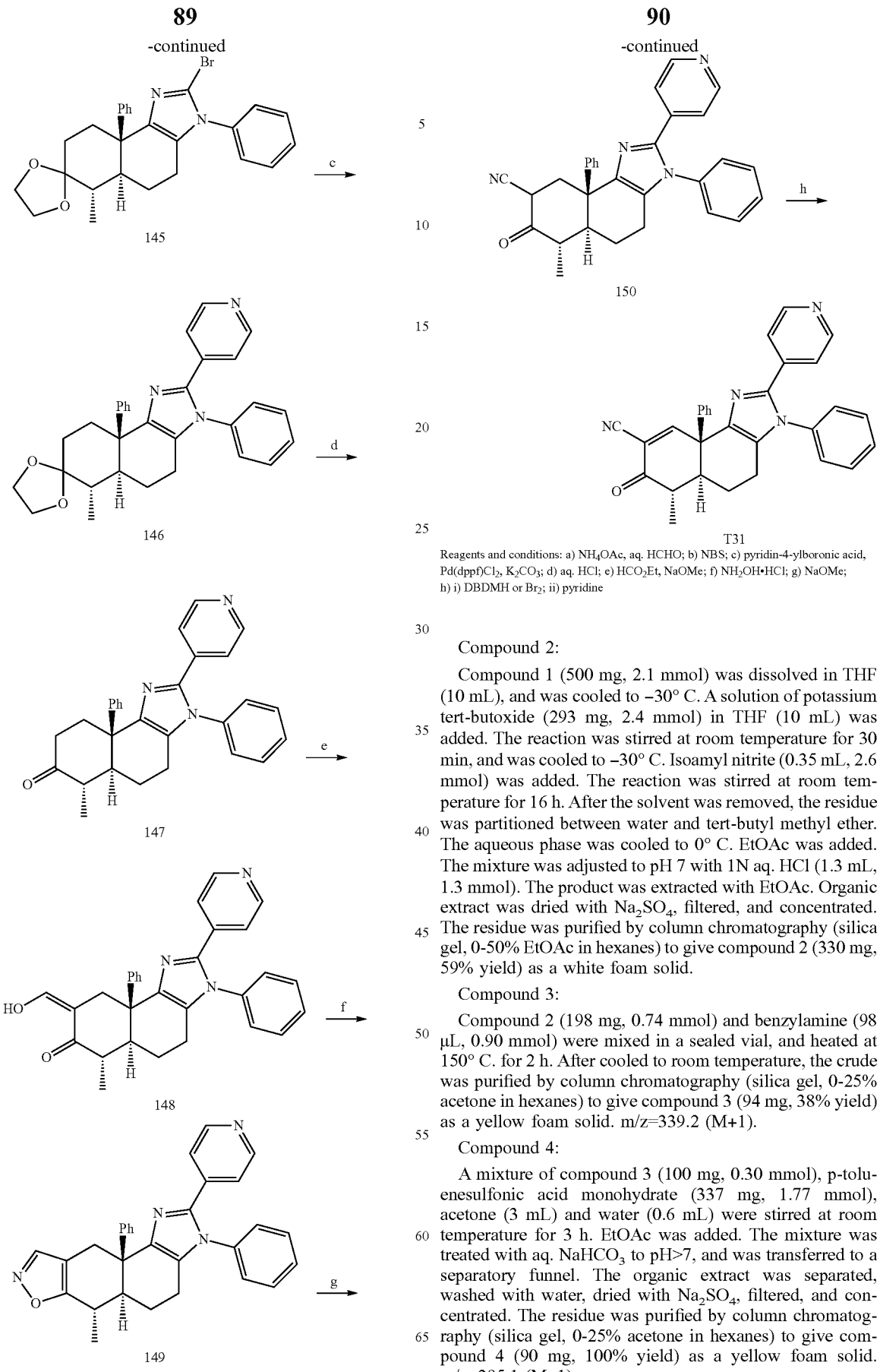

Reagents and conditions: a) NH₄OAc, aq. HCHO; b) NBS; c) pyridin-4-ylboronic acid, Pd(dppf)Cl₂, K₂CO₃; d) aq. HCl; e) HCO₂Et, NaOMe; f) NH₂OH·HCl; g) NaOMe; h) i) DBDMH or Br₂; ii) pyridine Compound 2:

Compound 1 (500 mg, 2.1 mmol) was dissolved in THF (10 mL), and was cooled to −30° C. A solution of potassium tert-butoxide (293 mg, 2.4 mmol) in THF (10 mL) was added. The reaction was stirred at room temperature for 30 min, and was cooled to −30° C. Isoamyl nitrite (0.35 mL, 2.6 mmol) was added. The reaction was stirred at room temperature for 16 h. After the solvent was removed, the residue was partitioned between water and tert-butyl methyl ether. The aqueous phase was cooled to 0° C. EtOAc was added. The mixture was adjusted to pH 7 with 1N aq. HCl (1.3 mL, 1.3 mmol). The product was extracted with EtOAc. Organic extract was dried with Na₂SO₄, filtered, and concentrated. The residue was purified by column chromatography (silica gel, 0-50% EtOAc in hexanes) to give compound 2 (330 mg, 59% yield) as a white foam solid.

Compound 3:

Compound 2 (198 mg, 0.74 mmol) and benzylamine (98 µL, 0.90 mmol) were mixed in a sealed vial, and heated at 150° C. for 2 h. After cooled to room temperature, the crude was purified by column chromatography (silica gel, 0-25% acetone in hexanes) to give compound 3 (94 mg, 38% yield) as a yellow foam solid. m/z=339.2 (M+1).

Compound 4:

A mixture of compound 3 (100 mg, 0.30 mmol), p-toluenesulfonic acid monohydrate (337 mg, 1.77 mmol), acetone (3 mL) and water (0.6 mL) were stirred at room temperature for 3 h. EtOAc was added. The mixture was treated with aq. NaHCO₃ to pH>7, and was transferred to a separatory funnel. The organic extract was separated, washed with water, dried with Na₂SO₄, filtered, and concentrated. The residue was purified by column chromatography (silica gel, 0-25% acetone in hexanes) to give compound 4 (90 mg, 100% yield) as a yellow foam solid. m/z=295.1 (M+1).

Compound 5:

NaOMe (25 wt. % in methanol, 230 µL, 1.00 mmol) was added to a mixture of compound 4 (20 mg, 68 µmol) in HCO₂Et (160 µL, 1.99 mmol) at 0° C. After stirring at room temperature for 1 h, the reaction was cooled to 0° C. MTBE and 6 N aq. HCl (170 µL, 1.02 mmol) were added sequentially. The mixture was treated with aq. NaHCO₃ to pH~6.7. The product was extracted with EtOAc. Combined organic extracts were dried with Na₂SO₄, filtered and concentrated.

The residue was mixed with NH₂OH.HCl (7 mg, 100 pined), EtOH (1 mL) and water (0.1 mL). After heated at 55° C. for 1 h, 1 N aq. HCl (100 µL, 100 µmol) was added. The reaction was heated for an additional 18 h. EtOH was removed. EtOAc was added. The mixture was treated with aq. NaHCO₃ to pH>7. Product was extracted with EtOAc. Combined organic extracts were washed with water, dried with Na₂SO₄, filtered and concentrated. The residue was purified by column chromatography (silica gel, 0-50% EtOAc in hexanes) to give compound 5 (15 mg, 69% yield) as a white foam solid. m/z=320.1 (M+1).

Compound 6:

NaOMe (16 µL, 69.3 µmol) was added to a solution of compound 5 (15 mg, 46.9 µmol) in MeOH (470 µL) at room temperature. After the reaction was heated at 55° C. for 1 h, MTBE (200 mL) was added. The mixture was treated with 1 N aq. HCl to pH~7. Product was extracted with EtOAc. Combined organic extracts were washed with water, dried with Na₂SO₄, filtered and concentrated to give compound 6 (13 mg, 87% yield) as a white solid. m/z=320.1 (M+1).

Compound T1:

A solution of 1,3-dibromo-5,5-dimethylhydantoin (6.2 mg, 21.7 µmol) in DMF (110 µL) was added to a solution of compound 6 (13.8 mg, 43.1 µmol) in DMF (110 µL) at 0° C. After the reaction was stirred at 0° C. for 1 h, pyridine (11 µL, 136.3 µmol) was added. The mixture was heated at 55° C. for 2 h. EtOAc was added. The mixture was washed with aq. NaHCO₃ and water. Organic extract was washed with water, dried with Na₂SO₄, filtered and concentrated. The residue was purified by column chromatography (silica gel, 0-30% acetone in hexanes) to give compound T1 (11 mg, 80% yield) as light brown foam solid. m/z=318 (M+1); $^1$H NMR (400 MHz, CDCl₃) δ 8.94 (bs, 1H), 8.62 (s, 1H), 7.75 (m, 2H), 7.42 (m, 2H), 7.34 (m, 1H), 2.68-2.82 (m, 2H), 2.55 (qd, 1H, J=6.8, 13.5 Hz), 2.06-2.20 (m, 2H), 1.83 (m, 1H), 1.44 (s, 3H), 1.29 (d, 3H, J=7.2 Hz).

Compound 8:

Ozone was bubbled through a stirring solution of compound 7 (2.00 g, 7.15 mmol) in dichloromethane (100 mL) at −78° C. The color never turned blue, but TLC after 1.5 h of the light green solution showed no starting material left. Oxygen was bubbled through the solution for 10 min, methyl sulfide (2.8 mL, 38.1 mmol) was added, the dry ice-acetone bath was removed and the sample was stirred at room temperature overnight. The sample was concentrated then chromatographed (silica gel, 30% EtOAc in hexanes) to give compound 8 (1.86 g, 98% yield) as a light yellow solid. m/z=253 (M+1).

Compound 9:

Compound 8 (1.04 g, 4.12 mmol) was taken up in benzene (200 mL). Aniline (1.2 g, 12.4 mmol) and p-toluenesulfonic acid monohydrate (780 mg, 4.12 mmol) were added. The reaction was stirred at refluxing for 16 h. The reaction mixture was filtered, concentrated. The crude residue was purified by column chromatography (silica gel, 0 to 20% EtOAc in hexanes) to give compound 9 (0.8 g, 60% yield) as an oil. m/z=328 (M+1).

Compound 10:

Compound 9 (740 mg, 2.26 mmol) was dissolved in EtOH (50 mL). Benzaldehyde (480 mg, 4.52 mmol) and ammonium acetate (1.75 g, 22.6 mmol) were added. The reaction mixture was stirred for two days at room temperature. The reaction mixture was concentrated. The residue was taken up in ethyl acetate, then washed with aq. NaHCO₃, dried with MgSO₄, and concentrated. The crude residue was purified by column chromatography (silica gel, 0 to 35% EtOAc in hexanes) to give compound 10 (800 mg, 85% yield) as an off-white solid. m/z=415 (M+1).

Compound 11:

Compound 10 (800 mg, 1.93 mmol) was taken up in THF (10 mL), and 3N HCl (aq, 5 mL) was added. The mixture was stirred overnight at room temperature. The reaction mixture was concentrated. The residue was neutralized with saturated aq. NaHCO₃, and was extracted with ethyl acetate. The organic extract was washed with water, then dried with MgSO₄, and concentrated to give a solid compound 11 (720 mg, quantitative yield). m/z=371 (M+1).

Compound 12:

Compound 11 (720 mg, 1.93 mmol) was taken up in ethyl formate (15 mL, 187.5 mmol). NaOMe (30 wt. % in methanol, 1.4 g, 5.8 mmol) was added. The reaction mixture was stirred overnight at room temperature. The reaction mixture was neutralized with aq. KH₂PO₄, and extracted with ethyl acetate. The organic extract was dried with MgSO₄ and concentrated to give compound 12 (770 mg, quantitative yield) as a solid. m/z=399 (M+1).

Compound 13:

Compound 12 (770 mg, 1.93 mmol) was dissolved in EtOH. Hydroxylamine hydrochloride (270 mg, 3.86 mmol) was added. The reaction mixture was stirred overnight at 50° C. After cooling to room temperature, the reaction mixture was concentrated. The residue was taken up in ethyl acetate, then washed with aq. NaHCO₃, dried with MgSO₄, and concentrated to give compound 13 (765 mg, quantitative yield) as a solid. m/z=396 (M+1).

Compound 14:

Compound 13 (765 mg, 1.93 mmol) was dissolved in THF (5 mL), and NaOMe (30 wt. % in methanol, 1.5 g, 7.72 mmol) was added. The reaction mixture was stirred at room temperature overnight. The reaction was neutralized by addition of saturated KH₂PO₄, and extracted with ethyl acetate. The organic extract was washed with brine, then dried with MgSO₄, and concentrated to give compound 14 (600 mg, 78% yield) as a solid. m/z=396 (M+1).

Compound T2:

Compound 14 (205 mg, 0.51 mmol) was dissolved in dry DMF (3 mL), and the solution was cooled to 0° C. Bromine (91 mg in 1 mL of dichloromethane, 0.57 mmol) was added, and the reaction was stirred at 0° C. for 2 h. Pyridine (1 mL, 13 mmol) was added, and the reaction was allowed to warm to room temperature. The reaction mixture was stirred at 50° C. for 16 h. The reaction mixture was concentrated. The crude residue was purified by column chromatography (silica gel, 0 to 35% EtOAc in hexanes) to give compound T2 (60 mg, 30% yield) as an off-white solid. m/z=394 (M+1); $^1$H NMR (400 MHz, CDCl₃) δ 8.69 (s, 1H), 7.43 (dd, 2H, J=1.9, 5.0 Hz), 7.43 (m, 1H), 7.34 (m, 2H), 7.20 (m, 5H), 2.59 (qd, 1H, J=6.8, 13.5 Hz), 2.51 (m, 2H), 2.16 (dt, 1H, J=2.2, 12.8 Hz), 2.06 (m, 1H), 1.82 (m, 1H), 1.53 (s, 3H), 1.30 (d, 3H, J=6.8 Hz);

Compound 15:

In a sealable vial, a mixture of 9 (0.82 g, 2.50 mmol), ammonium acetate (1.92 g, 25.04 mmol) and acetaldehyde (0.28 mL, 5.00 mmol) in ethanol (10 mL) was flushed with N₂, sealed and stirred at room temperature. TLC (silica gel, 30% EtOAc in hexanes) after 16 h at room temperature still showed starting material ($R_f$ 0.42) present. Another portion of acetaldehyde (0.28 mL, 5.00 mmol) was added. The sample was again flushed with $N_2$, sealed and stirred at room temperature for 48 h. The sample was concentrated then partitioned between 10% aq. $NH_4OH$ solution (50 mL) and $CHCl_3$ (50 mL). The organic extract was washed with brine (50 mL), dried ($MgSO_4$), filtered, concentrated and chromatographed (silica gel, 10% methanol in EtOAc) to give compound 15 (0.70 g, 80% yield) as tan solid. m/z=353 (M+1, 100%).

Compound 16:

A solution of 15 (0.70 g, 2.00 mmol) and 1N aq. HCl (20 mL, 20 mmol) in methanol (50 mL) was stirred at room temperature under $N_2$ for 16 h. The sample was concentrated, cooled, basified with 10% aq. $NH_4OH$ solution (to pH ~9-10) and extracted with $CHCl_3$ (3×25 mL). The combined organic extract was dried ($MgSO_4$), filtered and concentrated to give compound 16 (0.59 g, 96% yield) as off-white solid, which was used in the next step without purification. m/z=309 (M+1, 100%).

Compound 17:

To a stirring solution at room temperature under $N_2$ of compound 16 (0.59 g, 1.91 mmol) and ethyl formate (15.5 mL, 191.9 mmol) in benzene (25 mL) was added sodium methoxide (30 wt. % solution in methanol, 1.8 mL, 9.6 mmol). After 16 h, the solution was concentrated, cooled, acidified with excess saturated $KH_2PO_4$ solution (50 mL) and extracted with $CHCl_3$ (3×25 mL). The combined organic extract was dried ($MgSO_4$), filtered and concentrated to give compound 17 (0.80 g, quantitative yield) as tan foamy solid, which was used in the next reaction without purification. m/z=337 (M+1).

Compound 18:

A stirring solution under $N_2$ of sl. impure compound 17 (entire amount from last step, ≤1.91 mmol) and hydroxylamine hydrochloride (0.20 g, 2.88 mmol) in ethanol (25 mL) was heated at 50° C. for 2 h then room temperature overnight. The solution was concentrated, cooled, basified with saturated $NaHCO_3$ solution (50 mL) and extracted with $CHCl_3$ (3×25 mL). The combined organic extract was dried ($MgSO_4$), filtered and concentrated to give compound 18 (0.76 g, quantitative yield) as tan foamy solid, which was used in the next reaction without purification. m/z=334 (M+1).

Compound 19:

To a stirring solution at room temperature under $N_2$ of compound 18 (from last step [entire amount, used without purification], ≤1.91 mmol) in methanol (20 mL) was added sodium methoxide (30 wt. % solution in methanol, 1.8 mL, 9.6 mmol). The sample was stirred at room temperature for 16 h, concentrated, cooled, acidified with excess saturated $KH_2PO_4$ solution (50 mL) and extracted with $CHCl_3$ (3×25 mL). The combined organic extract was dried ($MgSO_4$), filtered and concentrated to give compound 19 (0.70 g, quantitative yield) as tan foamy solid, which was used in the next reaction without purification. m/z=334 (M+1, 100%).

Compound T3:

To a stirring solution at ~0° C. under $N_2$ of compound 19 (entire amount from last step, ≤1.91 mmol) in DMF (5 mL) was added dropwise a solution of 1,3-dibromo-5,5-dimethylhydantoin (0.27 g, 0.94 mmol) in DMF (5 mL). After stirring at 0° C. for 30 min, pyridine (1.5 mL, 18.5 mmol) was added. The ice-bath was removed, the sample was heated at 50° C. for 4 h, cooled, concentrated then partitioned between saturated $KH_2PO_4$ solution (50 mL) and $CHCl_3$ (50 mL). The aqueous extract was extracted with fresh $CHCl_3$ (2×25 mL). The combined organic extract was dried ($MgSO_4$), filtered, concentrated and chromatographed (silica gel, 100% EtOAc) to give compound T3 (0.18 g, 28% yield from 16) as off-white solid. m/z=332 (M+1); $^1$H NMR (400 MHz, $CDCl_3$) δ 8.55 (s, 1H), 7.49 (m, 3H), 7.21 (m, 2H), 2.55 (qd, 1H, J=6.8, 13.5 Hz), 2.45 (ddd, 1H, J=6.4, 11.0, 17.3 Hz), 2.37 (dd, 1H, J=6.6, 16.6 Hz), 2.26 (s, 3H), 2.11 (dt, 1H, J=2.3, 12.8 Hz), 2.02 (m, 1H), 1.74 (tdd, 1H, J=6.5, 11.2, 13.3 Hz), 1.45 (s, 3H), 1.28 (d, 3H, J=6.8 Hz).

Compound 20:

Compound 8 (1.21 g, 4.8 mmol) was taken up in benzene (200 mL). 3-Bromoaniline (2.45 g, 14.4 mmol) and $TsOH·H_2O$ (125 mg, 0.5 mmol) were added. The reaction was stirred at refluxing for 16 h. The reaction mixture was filtered, and concentrated. The crude residue was purified by column chromatography (silica gel, 0 to 25% EtOAc in hexanes) to give compound 20 (1.4 g, 72% yield) as an oil. m/z=406, 408 (1:1, M+1).

Compound 21:

Compound 20 (445 mg, 1.1 mmol) was dissolved in EtOH (20 mL). Benzaldehyde (235 mg, 2.2 mmol) and ammonium acetate (0.85 g, 11 mmol) were added. The reaction mixture was stirred for 24 h at room temperature, and then heated at 65° C. for two days. The reaction mixture was concentrated. The residue was taken up in ethyl acetate, then washed with aq. $NaHCO_3$, dried with $MgSO_4$, and concentrated. The crude residue was purified by column chromatography (silica gel, 0 to 35% EtOAc in hexanes) to give compound 21 (420 mg, 77% yield) as an off-white solid. m/z=493, 495 (1:1, M+1).

Compound 22:

Compound 21 (175 mg, 0.35 mmol) was taken up in toluene/$Et_3N$ (4:1, 5 mL). CuI (10 mg, 0.05 mmol), $Pd(PPh_3)_2Cl_2$ (20 mg, 0.03 mmol) and propargyl alcohol (25 mg, 0.44 mmol) were added. The mixture was bubbled with $N_2$ for 10 min. The reaction was stirred at 80° C. for 16 h. The reaction mixture was filtered, concentrated. The crude residue was purified by column chromatography (silica gel, 5 to 75% EtOAc in hexanes) to give compound 22 (150 mg, 30% yield) as a solid. m/z=469 (M+1).

Compound 23:

Compound 22 (125 mg, 0.267 mmol) was hydrogenated at atmospheric pressure in EtOAc (15 mL) over 10% Pd/C (25 mg) for 16 h at room temperature. The reaction mixture was filtered using a Celite® pad. The filtrate was concentrated to give compound 23 (82 mg, 67% yield) as an oil. m/z=473 (M+1).

Compound 24:

Compound 23 (82 mg, 0.17 mmol) was taken up in THF (2 mL), and 3N HCl (aq, 1 mL) was added. The mixture was stirred overnight at room temperature. The reaction mixture was concentrated. The residue was neutralized with saturated aq. $NaHCO_3$, and extracted with ethyl acetate. The organic extract was washed with water, then dried with $MgSO_4$, and concentrated to give compound 24 (70 mg, 96% yield) as a foam. m/z=429 (M+1).

Compound 25:

Compound 24 (70 mg, 0.16 mmol) was taken up in ethyl formate (10 mL, 125 mmol). NaOMe (30 wt. % in methanol, 120 mg, 0.65 mmol) was added. The mixture was stirred at room temperature overnight. The reaction mixture was neutralized with aq. $KH_2PO_4$, and extracted with ethyl acetate. The organic extract was dried with $MgSO_4$ and concentrated to give compound 25 (70 mg, 96% yield) as an oil. m/z=457 (M+1).

Compound 26:

Compound 25 (70 mg, 0.15 mmol) was dissolved in EtOH. Hydroxylamine hydrochloride (35 mg, 0.5 mmol) was added. The reaction mixture was stirred overnight at 50° C. After cooling to room temperature, the reaction mixture was concentrated. The residue was taken up in ethyl acetate, then washed with aq. NaHCO$_3$, dried with MgSO$_4$, and concentrated to give compound 26 (65 mg, 96% yield) as an oil. m/z=454 (M+1).

Compound 27:

Compound 26 (65 mg, 0.14 mmol) was dissolved in THF (2 mL), and NaOMe (30 wt. % in methanol, 105 mg, 0.56 mmol) was added. The reaction mixture was stirred at room temperature overnight. The reaction was neutralized by addition of saturated KH$_2$PO$_4$, and extracted with ethyl acetate. The organic extract was washed with brine, then dried with MgSO$_4$, and concentrated to give compound 27 (65 mg, 94% yield) as an oil. m/z=496 (M+1).

Compound T4:

Compound 27 (65 mg, 0.14 mmol) was dissolved in dry DMF (2 mL), and the solution was cooled to 0° C. Br$_2$ (25 mg in 1 mL of dichloromethane, 1.1 eq)) was added, and the reaction stirred at 0° C. for 2 h. Pyridine (1 mL, 13 mmol) was added, and the reaction was allowed to warm to room temperature. The reaction mixture was stirred at 50° C. for 16 hours. The reaction mixture was concentrated. The crude residue was purified by column chromatography (silica gel, 5 to 55% EtOAc in hexanes) to give compound T4 (10 mg, 15% yield) as an off-white solid. m/z=494 (M+1); $^1$H NMR (400 MHz, CDCl$_3$) δ 8.69 (s, 1H), 7.34 (m, 3H), 7.23 (m, 4H), 7.01 (m, 2H), 3.98 (t, 2H, J=6.5 Hz), 2.67 (t, 2H, 7.6 Hz), 2.56 (m, 3H), 2.12 (m, 2H), 2.04 (s, 3H), 1.86 (m, 3H), 1.52 (s, 3H), 1.30 (d, 3H, J=6.8 Hz).

Compound 28:

Compound 8 (270 mg, 1.07 mmol) was taken up in benzene (10 mL), and biphenyl-4-amine (199 mg, 1.18 mmol) was added followed by p-TsOH.H$_2$O (10 mg). The solution was heated at 80° C. for 2 days. The mixture was cooled, diluted with saturated NaHCO$_3$ (25 mL), and extracted with EtOAc (2×50 mL). The combined organic extracts were washed with brine (25 mL), dried over MgSO$_4$, concentrated, and dried under vacuum to give 0.44 g of a dark foam. Flash chromatography (silica gel, 100% CH$_2$Cl$_2$) gave compound 28 (270 mg, 62% yield) as an orange-yellow foam. m/z=404 (M+1).

Compound 29:

Compound 28 (260 mg, 0.64 mmol) was suspended in THF (2 mL) and EtOH (2 mL). Ammonium acetate (497 mg, 6.44 mmol) was added followed by acetaldehyde (0.14 mL, 2.49 mmol). The mixture was stirred overnight at room temperature. Another portion of acetaldehyde (0.14 mL) was added, and stirring was continued for another 2 d. The mixture was concentrated, diluted with saturated NaHCO$_3$ (25 mL), and extracted with EtOAc (2×50 mL). The combined organic extracts were washed with brine (25 mL), dried over MgSO$_4$, and concentrated to give 318 mg of an orange-yellow foam. Flash chromatography (silica gel, 9:1 EtOAc/CH$_2$Cl$_2$ then 5% MeOH/EtOAc) gave compound 29 (210 mg, 76% yield) as a light yellow foam. m/z=429 (M+1).

Compound 30:

Compound 29 (210 mg, 0.49 mmol) was taken up in THF (5 mL) and 1M aq. HCl (1 mL) was added. The solution was stirred for 3 d, then diluted with saturated NaHCO$_3$ (20 mL) and extracted with EtOAc (2×50 mL). The combined organic extracts were washed with brine (20 mL), dried over MgSO$_4$, concentrated, and dried under vacuum to give compound 30 (198 mg, quantitative yield) as a light yellow foam. m/z=385 (M+1).

Compound 31:

Compound 30 (0.49 mmol) was taken up in ethyl formate (5 mL) and cooled in an ice bath. NaOMe (0.88 g, 30 wt. % in MeOH) was added dropwise, and the solution was allowed to warm to room temperature and stirred overnight. The mixture was cooled in an ice bath, quenched by the addition of saturated aq. KH$_2$PO$_4$ (25 mL), and extracted with EtOAc (2×50 mL). The combined organic extracts were washed with brine (25 mL), dried over MgSO$_4$, concentrated, and dried under vacuum to give compound 31 (210 mg, quantitative yield) as a light yellow foam. m/z=413 (M+1).

Compound 32:

Compound 31 (0.49 mmol) was taken up in EtOH (5 mL). Hydroxylamine hydrochloride (68 mg, 0.98 mmol) was added and the mixture was heated at 50° C. for 3 h, then allowed to cool to room temperature and stirred overnight. The solution was concentrated, diluted with saturated aq. NaHCO$_3$ (25 mL) and extracted with EtOAc (2×50 mL). The combined organic extracts were washed with brine (25 mL), dried over MgSO$_4$, concentrated, and dried under vacuum to give compound 32 (210 mg, quantitative yield) as a light yellow foam. m/z=410 (M+1).

Compound 33:

Compound 32 (0.49 mmol) was taken up in THF (6 mL) and MeOH (2 mL) and NaOMe (0.88 g, 30 wt. % in MeOH) was added. The solution was stirred overnight at room temperature and then concentrated. Saturated aq. KH$_2$PO$_4$ (25 mL) was added, and the mixture was extracted with EtOAc (2×50 mL). The combined organic extracts were washed with brine (25 mL), dried over MgSO$_4$, and concentrated to give 198 mg of a light yellow solid. Flash chromatography (3% MeOH/CHCl$_3$) gave compound 33 (152 mg, 76% yield from 29) as a light yellow solid. m/z=410 (M+1).

Compound T5:

Compound 33 (150 mg, 0.37 mmol) was taken up in DMF (4 mL) and cooled in an ice bath. N,N'-dibromodimethylhydantoin (63 mg, 0.22 mmol) was added and the solution was stirred 1 h at 0° C. Pyridine (0.4 mL) was added and the solution was heated at 60° C. for 3 h. After cooling, the solution was diluted with saturated aq. NaHCO$_3$ (20 mL) and extracted with EtOAc (2×50 ml). The combined organic extracts were washed with brine, dried over MgSO$_4$, concentrated, and dried under vacuum to give 150 mg of a brown oil. Flash chromatography (2% MeOH/CHCl$_3$) gave compound T5 (85 mg, 57% yield) as a light yellow foam. m/z=408 (M+1); $^1$H NMR (400 MHz, CDCl$_3$) δ 8.56 (s, 1H), 7.71 (m, 2H), 7.62 (m, 2H), 7.49 (m, 2H), 7.42 (m, 1H), 7.28 (m, 2H), 2.57 (qd, 1H, J=6.8, 13.5 Hz), 2.46 (m, 2H), 2.32 (s, 3H), 2.12 (dt, 1H, J=2.2, 12.8 Hz), 2.04 (m, 1H), 1.76 (tdd, 1H, J=6.6, 10.9, 13.2 Hz), 1.46 (s, 3H), 1.29 (d, 3H, J=6.8 Hz).

Compound 34:

Compound 20 (1.83 g, 4.5 mmol) was taken up in acetic anhydride (10 g, 100 mmol). NaOAc (1.8 g, 22.5 mmol) was added. The reaction was stirred at 140° C. for 16 h. The reaction mixture was filtered, concentrated. The crude residue was purified by column chromatography (silica gel, 0 to 50% EtOAc in hexanes) to give compound 34 (0.7 g, 35% yield) as an oil. m/z=448, 450 (1:1, M+1).

Compound 35:

Compound 34 (700 mg, 0.35 mmol) was taken up in DME/Et$_3$N (4:1, 5 mL). CuI (30 mg, 0.15 mmol), Pd(PPh$_3$)

$_2Cl_2$ (50 mg, 0.08 mmol) and propargyl alcohol (105 mg, 1.88 mmol) were added. The mixture was bubbled with $N_2$ for 15 min. The reaction was stirred at 80° C. for 16 h. The reaction mixture was filtered, concentrated. The crude residue was purified by column chromatography (silica gel, 25 to 75% EtOAc in hexanes) to give compound 35 (220 mg, 34% yield) as a foam. m/z=424 (M+1).

Compound 36:

Compound 35 (200 mg, 0.47 mmol) was hydrogenated at atmospheric pressure in EtOAc (15 mL) over 10% Pd/C (25 mg) for 16 h at room temperature. The reaction mixture was filtered using a Celite® pad. The filtrate was concentrated to give compound 36 (180 mg, 90% yield) as an oil. m/z=430 (M+1).

Compound 37:

Compound 36 (180 mg, 0.42 mmol) was dissolved in EtOH (6 mL). Ammonium acetate (5 g, 65 mmol) was added. The reaction mixture was stirred for 6 h at 90° C. The reaction mixture was concentrated. The residue was taken up in ethyl acetate, then washed with aq. $NaHCO_3$, dried with $MgSO_4$, and concentrated. The crude residue was purified by column chromatography (silica gel, 25 to 100% EtOAc in hexanes) to give compound 37 (67 mg, 39% yield) as a foam. m/z=411 (M+1).

Compound 38:

Compound 37 (67 mg, 0.16 mmol) was taken up in THF (1 mL), and 3 N HCl (aq, 1 mL) was added. The mixture was stirred overnight at room temperature. The reaction mixture was concentrated. The residue was neutralized with saturated aq. $NaHCO_3$, and extracted with ethyl acetate. The organic extract was washed with water, then dried with $MgSO_4$, and concentrated to give compound 38 (60 mg, quantitative yield) as a foam. m/z=367 (M+1).

Compound 39:

Compound 38 (60 mg, 0.16 mmol) was taken up in ethyl formate (10 mL, 125 mmol). NaOMe (30 wt. % in methanol, 120 mg, 0.65 mmol) was added. The mixture was stirred overnight at room temperature. The reaction mixture was neutralized with aq. $KH_2PO_4$, and was extracted with ethyl acetate. The organic extract was dried with $MgSO_4$ and concentrated to give compound 39 (50 mg, 82% yield) as an oil. m/z=395 (M+1).

Compound 40:

Compound 39 (50 mg, 0.13 mmol) was dissolved in EtOH. Hydroxylamine hydrochloride (30 mg, 0.4 mmol) was added. The reaction mixture was stirred overnight at 50° C. After cooling to room temperature, the reaction mixture was concentrated. The residue was taken up in ethyl acetate, then washed with aq. $NaHCO_3$, dried with $MgSO_4$, and concentrated to give compound 40 (50 mg, quantitative yield) an oil. m/z=392 (M+1).

Compound 41:

Compound 40 (50 mg, 0.13 mmol) was dissolved in THF (2 mL), and NaOMe (30 wt. % in methanol, 95 mg, 0.52 mmol) was added. The reaction mixture was stirred at room temperature overnight. The reaction was neutralized by addition of saturated $KH_2PO_4$, and extracted with ethyl acetate. The organic extract was washed with brine, then dried with $MgSO_4$, and concentrated to give compound 41 (40 mg, 80% yield) as an oil. m/z=392 (M+1).

Compound T6:

Compound 41 (40 mg, 0.1 mmol) was dissolved in dry DMF (2 mL), and the solution was cooled to 0° C. $Br_2$ (18 mg in 1 ml of dichloromethane, 1.1 eq) was added, and the reaction stirred at 0° C. for 2 h. Pyridine (1 mL, 13 mmol) was added, and the reaction was allowed to warm to room temperature. The reaction mixture was stirred at 50° C. for 16 h. The reaction mixture was concentrated. The crude residue was purified by column chromatography (silica gel, 25 to 100% EtOAc in hexanes) to give compound T6 (10 mg, 25% yield) as a foam. m/z=390 (M+1); $^1$H NMR (400 MHz, $CDCl_3$) δ 8.55 (s, 1H), 7.42 (m, 1H), 7.05 (m, 3H), 3.71 (t, 2H, J=6.8 Hz), 2.79 (t, 2H, J=7.9 Hz), 2.27 (s, 3H), 2.21 (m, 9H), 1.45 (s, 3H), 1.28 (d, 3H, J=6.7 Hz).

Compound 42:

Compound 8 (309 mg, 1.22 mmol) was taken up in benzene (15 mL), and biphenyl-3-amine (228 mg, 1.35 mmol) was added followed by p-toluenesulfonic acid (10 mg). The solution was heated at 80° C. for 2 days then allowed to cool to room temperature and stirred overnight. Saturated $NaHCO_3$ (25 mL) was added and the mixture was extracted with EtOAc (2×50 mL). The combined organic extracts were washed with brine (25 mL), dried over $MgSO_4$, concentrated, and dried under vacuum to give 0.54 g of a dark foam. Flash chromatography (silica gel, 100% $CH_2Cl_2$) gave compound 42 (370 mg, 75% yield) as a light orange-yellow foam. m/z=404 (M+1).

Compound 43:

Compound 42 (365 mg, 0.90 mmol) was suspended in THF (3 mL) and EtOH (2 mL). Ammonium acetate (700 mg, 9.0 mmol) was added followed by acetaldehyde (0.20 mL, 3.62 mmol). The mixture was stirred overnight at room temperature. Another portion of acetaldehyde (0.20 mL) was added, and stirring was continued for another 2 d. The mixture was concentrated, diluted with saturated $NaHCO_3$ (25 mL), and extracted with EtOAc (2×50 mL). The combined organic extracts were washed with brine (25 mL), dried over $MgSO_4$, and concentrated to give 0.42 g of an orange-yellow foam. Flash chromatography (silica gel, 3% MeOH/EtOAc) gave of compound 43 (288 mg, 74% yield) as a light yellow foam. m/z=429 (M+1).

Compound 44:

Compound 43 (288 mg, 0.67 mmol) was taken up in THF (5 mL) and 1M HCl (1 mL) was added. The solution was stirred for 3 d. Saturated $NaHCO_3$ (25 mL) was added and the mixture was extracted with EtOAc (2×50 mL). The combined organic extracts were washed with brine (25 mL), dried over $MgSO_4$, concentrated, and dried under vacuum to give compound 44 (223 mg, 86% yield) as a light yellow foam. m/z=385 (M+1).

Compound 45:

Compound 44 (223 mg, 0.58 mmol) was taken up in ethyl formate (5 mL) and THF (2 mL) and cooled in an ice bath. NaOMe (30 wt. % in MeOH, 1.04 g, 5.8 mmol) was added dropwise, and the solution was allowed to warm to room temperature and stirred overnight. The mixture was cooled in an ice bath, quenched by the addition of saturated aq. $KH_2PO_4$ (25 mL), and extracted with EtOAc (2×50 mL). The combined organic extracts were washed with brine (25 mL), dried over $MgSO_4$, concentrated, and dried under vacuum to give compound 45 (265 mg, quantitative yield) as a light yellow foam. m/z=413 (M+1).

Compound 46:

Compound 45 (265 mg, 0.58 mmol) was taken up in EtOH (6 mL). Hydroxylamine hydrochloride (81 mg, 1.16 mmol) was added and the mixture was heated at 50° C. for 3 h, then allowed to cool to room temperature and stirred overnight. The solution was concentrated. Saturated aq. $NaHCO_3$ (20 mL) was added and the mixture was extracted with EtOAc (2×50 mL). The combined organic extracts were washed with brine (20 mL), dried over $MgSO_4$, concentrated, and dried under vacuum to give compound 46 (238 mg, quantitative yield) as a yellow foam. m/z=410 (M+1).

Compound 47:

Compound 46 (238 mg, 0.58 mmol) was taken up in THF (10 mL) and MeOH (2 mL) and NaOMe (30 wt. % in MeOH, 1.04 g, 5.8 mmol) was added. The solution was stirred overnight at room temperature and then concentrated. Saturated aq. $KH_2PO_4$ (25 mL) was added, and the mixture was extracted with EtOAc (2×50 mL). The combined organic extracts were washed with brine (20 mL), dried over $MgSO_4$, and concentrated to give 240 mg of a yellow foam. Flash chromatography (silica gel, 2% MeOH/$CHCl_3$) gave compound 47 (181 mg, 76% yield from 44) as a light yellow foam. m/z=410 (M+1).

Compound T7:

Compound 47 (176 mg, 0.43 mmol) was taken up in DMF (4 mL) and cooled in an ice bath. N,N'-Dibromodimethylhydantoin (74 mg, 0.26 mmol) was added and the solution was stirred 1 h at 0° C. Pyridine (0.4 mL) was added and the solution was heated at 60° C. for 3 h. After cooling, saturated aq. $NaHCO_3$ (20 mL) was added and the mixture was extracted with EtOAc (2×50 mL). The combined organic extracts were washed with brine (20 mL), dried over $MgSO_4$, concentrated, and dried under vacuum to give 160 mg of a brown oil. Flash chromatography (silica gel, 1:1 EtOAc/$CH_2Cl_2$) gave compound T7 (85 mg, 54% yield) as a light yellow foam. m/z=408 (M+1); $^1$H NMR (400 MHz, $CDCl_3$) δ 8.56 (s, 1H), 7.69 (d, 1H, J=7.9 Hz), 7.59 (m, 3H), 7.48 (t, 2H, J=7.5 Hz), 7.41 (m, 2H), 7.18 (d, 1H, J=7.9 Hz), 2.56 (qd, 1H, J=6.6, 13.1 Hz), 2.50 (m, 1H), 2.46 (ddd, 1H, J=6.3, 10.1, 16.4 Hz), 2.32 (s, 3H), 2.12 (dt, 1H, J=2.1, 13.0 Hz), 2.03 (m, 1H), 1.76 (dq, 1H, J=6.4, 12.6 Hz), 1.46 (s, 3H), 1.28 (d, 3H, J=6.7 Hz);

Compound 48:

Compound 8 (1 g, 4 mmol) was taken up in benzene (200 mL). 2-Methyl-2H-tetrazol-5-amine (475 mg, 4.8 mmol) and TsOH.$H_2O$ (100 mg, 0.5 mmol) were added. The reaction was stirred at refluxing for 2 days. The reaction mixture was filtered, and concentrated. The crude residue was purified by column chromatography (silica gel, 0 to 50% EtOAc in hexanes) to give compound 48 (1.05 g, 63% yield) as a foam. m/z=334 (M+1).

Compound 49:

Compound 48 (940 mg, 2.8 mmol) was dissolved in EtOH (40 mL). Benzaldehyde (600 mg, 5.6 mmol) and ammonium acetate (2.2 g, 28 mmol) were added. The reaction mixture was stirred for 16 h at room temperature, and then heated at 50° C. for another day. The reaction mixture was concentrated. The residue was taken up in ethyl acetate, then washed with aq. $NaHCO_3$, dried with $MgSO_4$, and concentrated. The crude residue was purified by column chromatography (silica gel, 0 to 50% EtOAc in hexanes) to give compound 49 (1.05 g, 90% yield) as an off-white solid. m/z=421 (M+1).

Compound 50:

Compound 49 (1.05 g, 1.93 mmol) was taken up in THF (5 mL), and 3N HCl (aq, 5 mL) was added. The mixture was stirred overnight at room temperature. The reaction mixture was concentrated. The residue was neutralized with saturated aq. $NaHCO_3$, and extracted with ethyl acetate. The organic extract was washed with water, dried with $MgSO_4$, and concentrated to give compound 50 (940 mg, quantitative yield) as a foam. m/z=377 (M+1).

Compound 51:

Compound 50 (940 mg, 2.5 mmol) was taken up in ethyl formate (15 mL). NaOMe (30 wt. % in methanol, 1.7 g, 9.4 mmol) was added. The mixture was stirred overnight at room temperature. The reaction mixture was neutralized with aq. $KH_2PO_4$, and extracted with ethyl acetate. The organic extract was dried with $MgSO_4$ and concentrated to give compound 51 (1 g, quantitative yield) as an oil. m/z=405 (M+1).

Compound 52:

Compound 51 (1 g, 2.5 mmol) was dissolved in EtOH. Hydroxylamine hydrochloride (500 mg, 7.2 mmol) was added. The reaction mixture was stirred overnight at 50° C. After cooling to room temperature, the reaction mixture was concentrated. The residue was taken up in ethyl acetate, then washed with aq. $NaHCO_3$, then dried with $MgSO_4$, and concentrated to give compound 52 (1 g, quantitative yield) as an oil. m/z=402 (M+1).

Compound 53:

Compound 52 (1 g, 2.5 mmol) was dissolved in THF (5 mL), and NaOMe (30 wt. % in methanol, 1.8 g, 10 mmol) was added. The reaction mixture was stirred at room temperature overnight. The reaction was neutralized by addition of saturated $KH_2PO_4$, and extracted with ethyl acetate. The organic extract was washed with brine, then dried with $MgSO_4$, and concentrated to give compound 53 (790 mg, 79% yield from 49) as an oil. m/z=402 (M+1).

Compound T8:

Compound 53 (790 mg, 1.96 mmol) was dissolved in dry DMF (4 mL), and the solution was cooled to 0° C. $Br_2$ (350 mg in 1 mL of dichloromethane, 1.1 eq) was added, and the reaction stirred at 0° C. for 2 h. Pyridine (2 ml, 26 mmol) was added, and the reaction was allowed to warm to room temperature. The reaction mixture was stirred at 50° C. for 16 hours, and was concentrated. The crude residue was purified by column chromatography (silica gel, 0 to 40% EtOAc in hexanes) to give compound T8 (255 mg, 33% yield) as a foam. m/z=400 (M+1); $^1$H NMR (400 MHz, $CDCl_3$) δ 8.63 (s, 1H), 7.36 (m, 5H), 4.36 (s, 3H), 2.63 (m, 3H), 2.17 (dt, 1H, J=1.8, 12.7 Hz), 2.11 (m, 1H), 1.85 (m, 1H), 1.51 (s, 3H), 1.31 (d, 3H, J=6.7 Hz).

Compound 54:

Compound 9 (0.26 g, 0.79 mmol) was taken up in EtOH (6 mL). A solution of 1-methyl-1H-pyrazole-4-carbaldehyde (175 mg, 1.59 mmol) in EtOH (1 mL) was added followed by ammonium acetate (612 mg, 7.9 mmol). The mixture was stirred 4 d at room temperature and then concentrated. Saturated $NaHCO_3$ (25 mL) was added and the mixture was extracted with EtOAc (2×50 mL). The combined organic extracts were washed with brine (25 mL), dried over $MgSO_4$, and concentrated to give 0.43 g of a dark yellow foam. Flash chromatography (silica gel, 2-5% MeOH/$CH_2Cl_2$) gave compound 54 (0.29 g, 87% yield) as a white solid. m/z=419 (M+1).

Compound 55:

Compound 54 (290 mg, 0.69 mmol) was taken up in THF (7 mL) and 1M HCl (1 mL) was added. The solution was stirred overnight and then concentrated. Saturated $NaHCO_3$ (20 mL) was added and the mixture was extracted with EtOAc (2×50 mL). The combined organic extracts were washed with brine (20 mL), dried over $MgSO_4$, concentrated, and dried under vacuum to give compound 55 (250 mg, 97% yield) as a white solid. m/z=375 (M+1).

Compound 56:

Compound 55 (227 mg, 0.61 mmol) was taken up in ethyl formate (5 mL) and cooled in an ice bath. NaOMe (1.09 g, 30 wt. % in MeOH) was added dropwise, and the solution was allowed to warm to room temperature and stirred 4 h. The mixture was cooled in an ice bath, quenched by the addition of saturated aq. $KH_2PO_4$ (25 mL), and extracted with EtOAc (2×50 mL). The combined organic extracts were washed with brine (25 mL), dried over $MgSO_4$, concentrated, and dried under vacuum to give compound 56 (265 mg, quantitative yield) as a light tan foam. m/z=403 (M+1).

Compound 57:

Compound 56 (0.61 mmol) was taken up in EtOH (6 mL). Hydroxylamine hydrochloride (85 mg, 1.22 mmol) was added. The mixture was heated at 50° C. for 3 h, then allowed to cool to room temperature and stirred overnight. The solution was concentrated. Saturated aq. NaHCO$_3$ (20 mL) was added, and the mixture was extracted with EtOAc (2×50 mL). The combined organic extracts were washed with brine (20 mL), dried over MgSO$_4$, concentrated, and dried under vacuum to give compound 57 (250 mg, quantitative yield) as a light yellow foam. m/z=400 (M+1).

Compound 58:

Compound 57 (0.61 mmol) was taken up in THF (10 mL) and MeOH (1 mL) and NaOMe (30 wt. % in MeOH, 1.09 g, 6.1 mmol) was added. The solution was stirred 4 h at room temperature, becoming a thick heterogeneous mixture. Most of the solvent was removed via rotary evaporation. Saturated aq. KH$_2$PO$_4$ (25 mL) was added and the mixture was extracted with EtOAc (2×50 mL). The combined organic extracts were washed with brine (20 mL), dried over MgSO$_4$, and concentrated to give 260 mg of a yellow foam. Flash chromatography (silica gel, 4% MeOH/CHCl$_3$) gave compound 58 (232 mg, 95% yield) as a light yellow foam. m/z=400 (M+1).

Compound T9:

Compound 58 (232 mg, 0.58 mmol) was taken up in DMF (5 mL) and cooled in an ice bath. N,N'-dibromodimethylhydantoin (83 mg, 0.29 mmol) was added and the solution was stirred 1 h at 0° C. Pyridine (0.5 mL) was added and the solution was heated at 60° C. for 4 h. After cooling, saturated aq. NaHCO$_3$ (20 mL) was added and the mixture was extracted with EtOAc (2×50 mL). The combined organic extracts were washed with brine (20 mL), dried over MgSO$_4$, concentrated, and dried under vacuum to give 176 mg of an orange solid. Flash chromatography (silica gel, 3% MeOH/CHCl$_3$) gave compound T9 (101 mg, 44% yield) as a light orange solid. m/z=398 (M+1); $^1$H NMR (400 MHz, CDCl$_3$) δ 8.63 (s, 1H), 7.51 (m, 3H), 7.34 (s, 1H), 7.25 (m, 2H), 7.06 (s, 1H), 3.81 (s, 3H), 2.57 (qd, 1H, J=6.8, 13.5 Hz), 2.43 (m, 2H), 2.13 (dt, 1H, J=2.3, 12.8 Hz), 2.05 (m, 1H), 1.79 (m, 1H), 1.49 (s, 3H), 1.29 (d, 3H, J=6.8 Hz);

Compound 59:

Compound 8 (0.7 g, 2.7 mmol) was taken up in benzene (100 mL). 2-Methyl-aniline (360 mg, 3.4 mmol) and TsOH.H$_2$O (50 mg, 0.25 mmol) were added. The reaction was stirred at refluxing for 2 days. The reaction mixture was filtered, concentrated. The crude residue was purified by column chromatography (silica gel, 0 to 35% EtOAc in hexanes) to give compound 59 (0.49 g, 53% yield) as an oil. m/z=342 (M+1).

Compound 60:

Compound 59 (490 mg, 1.43 mmol) was dissolved in EtOH (10 mL). Acetaldehyde (130 mg, 2.9 mmol) and ammonium acetate (1.1 g, 14 mmol) were added. The reaction mixture was stirred for 16 h at room temperature. Acetaldehyde (130 mg) was added and stirred for 2 days. The reaction mixture was concentrated. The residue was taken up in ethyl acetate, washed with aq. NaHCO$_3$, dried with MgSO$_4$, and concentrated. The crude residue was purified by column chromatography (silica gel, 0 to 5% MeOH in EtOAc) to give compound 60 (140 mg, 27% yield) as a foam. m/z=367 (M+1).

Compound 61:

Compound 60 (140 mg, 0.38 mmol) was taken up in THF (2 mL), and 3N HCl (aq, 2 mL) was added. The mixture was stirred overnight at room temperature. The reaction mixture was concentrated. The residue was neutralized with saturated aq. NaHCO$_3$, and extracted with ethyl acetate. The organic extract was washed with water, then dried with MgSO$_4$, and concentrated to give 61 (120 mg, quantitative yield) as a foam. m/z=323 (M+1).

Compound 62:

Compound 61 (120 mg, 0.37 mmol) was taken up in ethyl formate (10 mL, 125 mmol). NaOMe (30 wt. % in methanol, 0.3 g, 1.67 mmol) was added. The mixture was stirred overnight at room temperature. The reaction mixture was neutralized with aq. KH$_2$PO$_4$, and was extracted with ethyl acetate. The organic extract was dried with MgSO$_4$ and concentrated to give compound 62 (130 mg, quantitative yield) as an oil. m/z=351 (M+1).

Compound 63:

Compound 62 (130 mg, 0.37 mmol) was dissolved in EtOH. Hydroxylamine hydrochloride (55 mg, 0.8 mmol) was added. The reaction mixture was stirred overnight at 50° C. After cooling to room temperature, the reaction mixture was concentrated. The residue was taken up in ethyl acetate, then washed with aq. NaHCO$_3$, dried with MgSO$_4$, and concentrated to give compound 63 (130 mg, quantitative yield) as an oil. m/z=348 (M+1).

Compound 64:

Compound 63 (130 mg, 0.37 mmol) was dissolved in THF (2 mL), and NaOMe (30 wt. % in methanol, 300 mg, 1.67 mmol) was added. The reaction mixture was stirred at room temperature overnight. The reaction was neutralized by addition of saturated KH$_2$PO$_4$, and extracted with ethyl acetate. The organic extract was washed with brine, then dried with MgSO$_4$, and concentrated to give compound 64 (110 mg, 86% yield from 60) as an oil. m/z=348 (M+1).

Compound T10:

Compound 64 (110 mg, 0.32 mmol) was dissolved in dry DMF (2 mL), and the solution was cooled to 0° C. Br$_2$ (56 mg in 1 mL of dichloromethane, 1.1 eq) was added, and the reaction stirred at 0° C. for 2 h. Pyridine (2 mL, 26 mmol) was added, and the reaction was allowed to warm to room temperature. The reaction mixture was stirred at 50° C. for 16 hours, then concentrated. The crude residue was purified by column chromatography (silica gel, 0 to 5% MeOH in EtOAc) to give compound T10 (30 mg, 27% yield) as a foam. m/z=346 (M+1); $^1$H NMR (400 MHz, CDCl$_3$, 1:1 atropisomers) δ [8.57 (s), 8.56 (s)] (1H), 7.35 (m, 4H), [7.15 (d, J=7.4 Hz), 7.09 (d, J=7.4 Hz)] (1H), 2.55 (qd, 1H, J=6.8, 13.4 Hz), 2.18 (m, 3H), 2.14 (s, 3H), [2.01 (s), 1.99 (s)] (3H), 1.75 (m, 1H), [1.45 (s), 1.45 (s)] (3H), 1.28 (d, 3H, J=6.9 Hz).

Compound 65:

Compound 9 (0.76 g, 2.32 mmol) was taken up in EtOH (15 mL) and ammonium acetate (1.79 g, 23.2 mmol) was added followed by a solution of 3-(benzyloxy)propanal (762 mg, 4.64 mmol) in EtOH (2 mL). The mixture was stirred overnight at room temperature. An additional portion of 3-(benzyloxy)propanal (240 mg) was added and the mixture was stirred 3 d at room temperature. The mixture was heated at 80° C. for 24 h, then cooled and concentrated. Saturated NaHCO$_3$ (50 mL) was added and the mixture was extracted with EtOAc (2×75 mL). The combined organic extracts were washed with brine (25 mL), dried over MgSO$_4$, concentrated, and dried under vacuum to give 1.40 g of an orange oil. Flash chromatography (silica gel, 2% MeOH/CHCl$_3$) gave compound 65 (384 mg, 35% yield) as a yellow foam. m/z=473 (M+1).

Compound 66:

Compound 65 (384 mg, 0.81 mmol) was taken up in THF (7 mL) and 1M HCl (1 mL) was added. The solution was stirred 3 d and then concentrated. Saturated NaHCO$_3$ (20 mL) was added and the mixture was extracted with EtOAc (2×50 mL). The combined organic extracts were washed with brine (20 mL), dried over MgSO$_4$, concentrated, and dried under vacuum to give compound 66 (316 mg, 91% yield) as a yellow oil. m/z=429 (M+1).

Compound 67:

Compound 66 (316 mg, 0.74 mmol) was taken up in ethyl formate (5 mL) and cooled in an ice bath. NaOMe (1.3 g, 30 wt. % in MeOH) was added dropwise, and the solution was allowed to warm to room temperature and stirred 5 h. The mixture was cooled in an ice bath, quenched by the addition of saturated aq. KH$_2$PO$_4$ (25 mL), and extracted with EtOAc (2×50 mL). The combined organic extracts were washed with brine (25 mL), dried over MgSO$_4$, concentrated, and dried under vacuum to give compound 67 (336 mg, 99% yield) as a light brown foam. m/z=457 (M+1).

Compound 68:

Compound 67 (336 mg, 0.74 mmol) was taken up in EtOH (6 mL). Hydroxylamine hydrochloride (102 mg, 1.47 mmol) was added and the mixture was heated at 50° C. for 3 h, then cooled and concentrated. Saturated aq. NaHCO$_3$ (20 mL) was added and the mixture was extracted with EtOAc (2×50 mL). The combined organic extracts were washed with brine (20 mL), dried over MgSO$_4$, concentrated, and dried under vacuum to give compound 68 (317 mg, 95% yield) as a yellow-brown foam. m/z=454 (M+1).

Compound 69:

Compound 68 (317 mg, 0.70 mmol) was taken up in THF (10 mL) and MeOH (1 mL) and NaOMe (1.26 g, 30 wt. % in MeOH) was added. The solution was stirred 5 h at room temperature and then concentrated. Saturated aq. KH$_2$PO$_4$ (25 mL) was added, and the mixture was extracted with EtOAc (2×50 mL). The combined organic extracts were washed with brine (20 mL), dried over MgSO$_4$, and concentrated to give 320 mg of a dark yellow foam. Flash chromatography (silica gel, 2% MeOH/CHCl$_3$) gave compound 69 (240 mg, 76% yield) as a yellow foam. m/z=454 (M+1).

Compound T11:

Compound 69 (62 mg, 0.14 mmol) was taken up in DMF (2 mL) and cooled in an ice bath. N,N'-dibromodimethylhydantoin (20 mg, 0.068 mmol) was added and the solution was stirred 1 h at 0° C. Pyridine (0.1 mL) was added and the solution was heated at 60° C. for 4 h. After cooling, saturated aq. NaHCO$_3$ (20 mL) was added and the mixture was extracted with EtOAc (2×50 mL). The combined organic extracts were washed with brine (20 mL), dried over MgSO$_4$, concentrated, and dried under vacuum to give 67 mg of a yellow oil. Flash chromatography (silica gel, 1:3 EtOAc/CH$_2$Cl$_2$) gave compound T11 (32 mg, 52% yield) as a light yellow foam. m/z=452 (M+1); $^1$H NMR (400 MHz, CDCl$_3$) δ 8.56 (s, 1H), 7.45 (m, 3H), 7.28 (m, 3H), 7.20 (m, 4H), 4.45 (s, 3H), 3.74 (m, 2H), 2.88 (m, 1H), 2.55 (qd, 1H, J=6.8, 13.5 Hz), 2.38 (m, 2H), 2.10 (dt, 1H, J=2.2, 12.8 Hz), 2.02 (m, 1H), 1.75 (m, 1H), 1.45 (s, 3H), 1.28 (d, 3H, J=6.7 Hz).

Compound 70:

Compound 69 (165 mg, 0.36 mmol) was taken up in MeOH (10 mL) and placed under nitrogen. 10% Pd/C (40 mg) was added, and the flask was evacuated and purged with hydrogen (3×), then stirred overnight under a hydrogen balloon. 20% Pd(OH)$_2$/C (40 mg) was added, and the mixture was resubjected to hydrogenation for 24 h. Another portion of 20% Pd(OH)$_2$/C (40 mg) was added and the mixture was resubjected to hydrogenation for 48 h. The mixture was filtered through a fine frit and the filtrate was concentrated. Flash chromatography (silica gel, 5% MeOH/CHCl$_3$) gave 55 mg of impure compound 70 as a white foam. This material was re-chromatographed (silica gel, 5% MeOH/EtOAc) to give compound 70 (15 mg, 9% yield) as a white solid. m/z=364 (M+1).

Compound T12:

Compound 70 (15 mg, 0.041 mmol) was taken up in DMF (1 mL) and cooled in an ice bath. N,N'-dibromodimethylhydantoin (5.9 mg, 0.021 mmol) was added and the solution was stirred 1 h at 0° C. Pyridine (0.1 mL) was added and the solution was heated at 60° C. for 4 h. The solution was cooled and concentrated to a brown oil. Flash chromatography (silica gel, 3-5% MeOH/CHCl$_3$) gave compound T12 (8.6 mg, 58% yield) as a yellow solid. m/z=362 (M+1); $^1$H NMR (400 MHz, CDCl$_3$) δ 8.49 (s, 1H), 7.50 (m, 3H), 7.20 (m, 2H), 3.93 (m, 2H), 2.71 (m, 2H), 2.56 (qd, 1H, J=6.8, 13.4 Hz), 2.41 (m, 2H), 2.11 (dt, 1H, J=2.3, 12.9 Hz), 2.02 (m, 1H), 1.76 (m, 1H), 1.58 (br s, 1H), 1.44 (s, 3H), 1.28 (d, 3H, J=6.8 Hz).

Compound 71:

Compound 8 (0.5 g, 2 mmol) was taken up in benzene (100 mL). 1-Methyl-1H-pyrazol-4-amine (250 mg, 2.57 mmol) and TsOH.H$_2$O (50 mg, 0.25 mmol) were added. The reaction was stirred at refluxing for 2 days, and was filtered, concentrated. The crude residue was purified by column chromatography (silica gel, 0 to 35% EtOAc in hexanes) to give compound 71 (0.52 g, 79% yield) as an oil. m/z=332 (M+1).

Compound 72:

Compound 71 (520 mg, 1.56 mmol) was dissolved in EtOH (10 mL). Acetaldehyde (150 mg, 3.4 mmol) and ammonium acetate (1.3 g, 17 mmol) were added. The reaction mixture was stirred for 16 h at room temperature. Acetaldehyde (150 mg) was added and stirring continued for 2 days. The reaction mixture was concentrated. The residue was taken up in ethyl acetate, washed with aq. NaHCO$_3$, dried with MgSO$_4$, and concentrated. The crude residue was purified by column chromatography (silica gel, 0 to 5% MeOH in EtOAc) to give compound 72 (520 mg, 93% yield) as a solid. m/z=357 (M+1).

Compound 73:

Compound 72 (520 mg, 1.46 mmol) was taken up in THF (5 mL), and 3N HCl (aq, 3 mL) was added. The mixture was stirred overnight at room temperature, then concentrated. The residue was neutralized with saturated aq. NaHCO$_3$, and was extracted with ethyl acetate. The organic extract was washed with water, dried with MgSO$_4$, and concentrated to give compound 73 (455 mg, quantitative yield) as a foam. m/z=313 (M+1).

Compound 74:

Compound 73 (455 mg, 1.46 mmol) was taken up in ethyl formate (15 mL, 187.5 mmol). NaOMe (30 wt. % in methanol, 1.05 g, 6 mmol) was added. The mixture was stirred overnight at room temperature, neutralized with aq. KH$_2$PO$_4$, and extracted with ethyl acetate. The organic extract was dried with MgSO$_4$ and concentrated to give compound 74 (495 mg, quantitative yield) as an oil. m/z=341 (M+1).

Compound 75:

Compound 74 (495 mg, 1.46 mmol) was dissolved in EtOH. Hydroxylamine hydrochloride (205 mg, 3 mmol) was added. The reaction mixture was stirred overnight at 50° C., cooled to room temperature, and concentrated. The residue was taken up in ethyl acetate, washed with aq. NaHCO$_3$, dried with MgSO$_4$, and concentrated to give compound 75 (485 mg, quantitative yield) as an oil. m/z=338 (M+1).

Compound 76:

Compound 75 (485 mg, 1.46 mmol) was dissolved in THF (2 mL), and NaOMe (30 wt. % in methanol, 1.05 g, 5.8 mmol) was added. The reaction mixture was stirred at room temperature overnight. The reaction was neutralized by addition of saturated KH$_2$PO$_4$, and extracted with ethyl acetate. The organic extract was washed with brine, dried with MgSO$_4$, and concentrated to give compound 76 (380 mg, 77% yield from 72) as a solid. m/z=338 (M+1).

Compound T13:

Compound 76 (380 mg, 1.12 mmol) was dissolved in dry DMF (2 mL), and the solution was cooled to 0° C. Br$_2$ (200 mg in 1 mL of dichloromethane, 1.1 eq) was added, and the reaction stirred at 0° C. for 2 h. Pyridine (2 mL, 26 mmol) was added, and the reaction was allowed to warm to room temperature. The reaction mixture was stirred at 50° C. for 16 h, then concentrated. The crude residue was purified by column chromatography (silica gel, 0 to 5% MeOH in EtOAc) to give compound T13 (135 mg, 36% yield) as a foam. m/z=336 (M+1); $^1$H NMR (400 MHz, CDCl$_3$) δ 8.52 (s, 1H), 7.48 (s, 1H), 7.44 (s, 1H), 3.98 (s, 3H), 2.54 (qd, 1H, J=6.8, 13.5 Hz), 2.42 (m, 2H), 2.29 (s, 3H), 2.06 (m, 2H), 1.74 (m, 1H), 1.43 (s, 3H), 1.28 (d, 3H, J=6.7 Hz).

Compound 77:

Compound 8 (1.8 g, 7.1 mmol) was taken up in benzene (200 mL). (E)-Methyl 3-(3-aminophenyl) acrylate (1.6 g, 9 mmol) and TsOH.H$_2$O (150 mg, 0.75 mmol) were added. The reaction was stirred at refluxing for 16 h. The reaction mixture was filtered, and concentrated. The crude residue was purified by column chromatography (silica gel, 0 to 50% EtOAc in hexanes) to give compound 77 (2.7 g, 92% yield) as an oil. m/z=412 (M+1).

Compound 78:

Compound 77 (2.6 g, 6.3 mmol) was dissolved in EtOH (100 mL). Acetaldehyde (560 mg, 12.6 mmol) and ammonium acetate (4.8 g, 63 mmol) were added. The reaction mixture was stirred for 16 h at room temperature. Acetaldehyde (560 mg) was added and stirred for another day. The reaction mixture was concentrated. The residue was taken up in ethyl acetate, washed with aq. NaHCO$_3$, dried with MgSO$_4$, and concentrated. The crude residue was purified by column chromatography (silica gel, 0 to 5% MeOH in EtOAc) to give compound 78 (800 mg, 29% yield) as an oil. m/z=437 (M+1).

Compound 79:

Compound 78 (800 mg, 1.83 mmol) was taken up in THF (10 mL), and 3N HCl (aq, 5 mL) was added. The mixture was stirred overnight at room temperature. The reaction mixture was concentrated, neutralized with saturated aq. NaHCO$_3$, and extracted with ethyl acetate. The organic extract was washed with water, dried with MgSO$_4$, and concentrated to give compound 79 (650 mg, 90% yield) as a foam. m/z=393 (M+1).

Compound 80:

Compound 79 (650 mg, 1.65 mmol) was taken up in ethyl formate (15 mL, 187.5 mmol). NaOMe (30 wt. % in methanol, 0.8 g, 4.4 mmol) was added. The mixture was stirred overnight at room temperature, neutralized with aq. KH$_2$PO$_4$, and extracted with ethyl acetate. The organic extract was dried with MgSO$_4$ and concentrated to give compound 80 (685 mg, 95% yield) as a foam. m/z=435 (M+1).

Compound 81:

Compound 80 (685 mg, 1.57 mmol) was dissolved in EtOH.

Hydroxylamine hydrochloride (250 mg, 3.6 mmol) was added. The reaction mixture was stirred overnight at 50° C., cooled to room temperature, and concentrated. The residue was taken up in ethyl acetate, washed with aq. NaHCO$_3$, dried with MgSO$_4$, and concentrated to give compound 81 (642 mg, 95% yield) as an oil. m/z=432 (M+1).

Compound 82 and 83:

Compound 81 (642 mg, 1.48 mmol) was dissolved in THF (10 mL), and NaOMe (30 wt. % in methanol, 1.1 g, 6 mmol) was added. The reaction mixture was stirred at room temperature overnight, then neutralized by addition of saturated KH$_2$PO$_4$, and extracted with ethyl acetate. The organic extract was washed with brine, dried with MgSO$_4$, and concentrated to give a mixture of compound 82 and compound 83 (485 mg) as an oil. m/z=418 (M+1 for 82) and 404 (M+1 for 83).

Compound 84 and 85:

The mixture of compound 82 and 83 (480 mg) was hydrogenated at atmospheric pressure in EtOAc/THF (10:1, 22 mL) over 10% Pd/C (35 mg) for 16 h at room temperature. The reaction mixture was filtered using a Celite pad. The filtrate was concentrated, purified by column chromatography (silica gel, 0 to 15% MeOH in EtOAc) to isolate compound 84 (184 mg, 29% yield from 81) and compound 85 (169 mg, 28% yield from 81) as an oil. Compound 84: m/z=420 (M+1); Compound 85: m/z=406 (M+1).

Compound T14:

Compound 84 (184 mg, 0.458 mmol) was dissolved in dry DMF (4 mL), and the solution was cooled to 0° C. Br$_2$ (80 mg in 1 mL of dichloromethane, 1.1 eq) was added, and the reaction stirred at 0° C. for 2 h. Pyridine (2 mL, 26 mmol) was added, and the reaction was allowed to warm to room temperature. The reaction mixture was stirred at 50° C. for 16 hours. The reaction mixture was concentrated. The crude residue was purified by column chromatography (silica gel, 50 to 100% EtOAc in hexanes) to give compound T14 (50 mg, 27% yield) as a foam. m/z=418 (M+1); $^1$H NMR (400 MHz, CDCl$_3$) δ 8.55 (s, 1H), 7.42 (m, 1H), 7.30 (d, 1H, J=8.0 Hz), 7.05 (m, 2H), 3.67 (s, 3H), 3.02 (t, 2H, J=7.6 Hz), 2.67 (t, 2H, J=7.6 Hz), 2.55 (qd, 1H, J=6.7, 13.4 Hz), 2.39 (m, 2H), 2.26 (s, 3H), 2.10 (dt, 1H, J=2.2, 12.9 Hz), 2.02 (m, 1H), 1.74 (m, 1H), 1.45 (s, 3H), 1.28 (d, 3H, J=6.8 Hz).

Compound T15:

Compound 85 (160 mg, 0.39 mmol) was dissolved in dry DMF (4 mL), and the solution was cooled to 0° C. Br$_2$ (70 mg in 1 mL of dichloromethane, 1.1 eq) was added, and the reaction stirred at 0° C. for 2 h. Pyridine (2 mL, 26 mmol) was added, and the reaction was allowed to warm to room temperature. The reaction mixture was stirred at 50° C. for 16 hours. The reaction mixture was concentrated. The crude residue was purified by column chromatography (silica gel, 0 to 15% MeOH in EtOAc) to give compound T15 (25 mg, 16% yield) as a foam. m/z=404 (M+1); $^1$H NMR (400 MHz, CDCl$_3$) δ 8.42 (s, 1H), 7.44 (t, 1H, J=7.7 Hz), 7.35 (d, 1H, J=7.7 Hz), 7.15 (s, 1H), 7.02 (d, 1H, J=8.0 Hz), 3.06 (t, 2H, J=6.6 Hz), 2.72 (t, 2H, J=6.6 Hz), 2.53 (qd, 1H, J=6.7, 13.4 Hz), 2.39 (m, 2H), 2.15 (s, 3H), 2.05 (m, 2H), 1.71 (m, 1H), 1.40 (s, 3H), 1.27 (d, 3H, J=6.9 Hz).

Compound 86:

Compound 48 (228 mg, 0.68 mmol) was taken up in THF (2 mL) and EtOH (2 mL). Ammonium acetate (524 mg, 6.8 mmol) was added followed by a solution of 1-methyl-1H-pyrazole-4-carbaldehyde (150 mg, 1.36 mmol) in EtOH (1 mL). The mixture was stirred 7 d at room temperature.

Saturated NaHCO$_3$ (25 mL) was added and the mixture was extracted with EtOAc (2×50 mL). The combined organic extracts were washed with brine (25 mL), dried over MgSO$_4$, and concentrated to give 0.47 g of a yellow oil. Flash chromatography (silica gel, 2-5% MeOH/CH$_2$Cl$_2$) gave impure compound 86 (85 mg, 29% yield) as a yellow oil. m/z=425 (M+1).

Compound 87:

Impure compound 86 (85 mg, 0.20 mmol) was taken up in THF (3 mL) and 1M HCl (0.5 mL) was added. The solution was stirred 3 d at room temperature, saturated NaHCO$_3$ (20 mL) was added, and the mixture was extracted with EtOAc (2×50 mL). The combined organic extracts were washed with brine (20 mL), dried over MgSO$_4$, concentrated, and dried under vacuum to give 80 mg of an oil. Flash chromatography (silica gel, 2-5% MeOH/CHCl$_3$) gave compound 87 (45 mg, 59% yield) as a white foam. m/z=381 (M+1).

Compound 88:

Compound 87 (45 mg, 0.12 mmol) was taken up in ethyl formate (2 mL) and cooled in an ice bath. NaOMe (0.21 g, 30 wt. % in MeOH) was added dropwise, and the solution was allowed to warm to room temperature and stirred 2 h. The mixture was cooled in an ice bath, quenched by the addition of saturated aq. KH$_2$PO$_4$ (20 mL), and extracted with EtOAc (2×50 mL). The combined organic extracts were washed with brine (20 mL), dried over MgSO$_4$, concentrated, and dried under vacuum to give compound 88 (48 mg, quantitative yield) as a light yellow foam. m/z=409 (M+1).

Compound 89:

Compound 88 (48 mg, 0.12 mmol) was taken up in EtOH (2 mL). Hydroxylamine hydrochloride (25 mg, 0.36 mmol) was added and the mixture was heated at 50° C. for 4 h, then allowed to cool to room temperature and stirred overnight. The solution was concentrated, saturated aq. NaHCO$_3$ (20 mL) was added, and the mixture was extracted with EtOAc (2×50 mL). The combined organic extracts were washed with brine (20 mL), dried over MgSO4, concentrated, and dried under vacuum to give compound 89 (44 mg, 92% yield from 87) as a light yellow foam. m/z=406 (M+1).

Compound 90:

Compound 89 (44 mg, 0.11 mmol) was taken up in THF (3 mL) and MeOH (1 mL) and NaOMe (0.21 g, 30 wt. % in MeOH) was added. The solution was stirred 6 h at room temperature, and most of the solvent was removed via rotary evaporation. Saturated aq. KH$_2$PO$_4$ (20 mL) was added, and the mixture was extracted with EtOAc (2×50 mL). The combined organic extracts were washed with brine (20 mL), dried over MgSO$_4$, and concentrated to give 44 mg of a light yellow foam. Flash chromatography (silica gel, CHCl$_3$ then 2% MeOH/CHCl$_3$) gave compound 90 (33 mg, 75% yield) as a pale yellow glass. m/z=406 (M+1).

Compound T16:

Compound 90 (33 mg, 0.081 mmol) was taken up in DMF (2 mL) and cooled in an ice bath. N,N'-dibromodimethylhydantoin (11.6 mg, 0.041 mmol) was added and the solution was stirred 1 h at 0° C. Pyridine (0.1 mL) was added and the solution was heated at 60° C. for 4 h. After cooling, saturated aq. NaHCO$_3$ (20 mL) was added and the mixture was extracted with EtOAc (2×50 mL). The combined organic extracts were washed with brine (20 mL), dried over MgSO$_4$, concentrated, and dried under vacuum to give 27 mg of a brown oil. Flash chromatography (silica gel, 2% MeOH/CHCl$_3$) gave compound T16 (12 mg, 37% yield) as a light yellow foam. m/z=404 (M+1); $^1$H NMR (400 MHz, CDCl$_3$) δ 8.57 (s, 1H), 7.72 (s, 1H), 7.43 (s, 1H), 4.42 (s, 3H), 3.90 (s, 3H), 2.60 (m, 3H), 2.12 (m, 2H), 1.84 (m, 1H), 1.48 (s, 3H), 1.31 (d, 3H, J=6.7 Hz).

Compound 91:

Compound 71 (380 mg, 1.14 mmol) was dissolved in EtOH (10 mL). Benzaldehyde (250 mg, 2.3 mmol) and ammonium acetate (0.9 g, 11 mmol) were added. The reaction mixture was stirred for 16 h at room temperature, then concentrated. The residue was taken up in ethyl acetate, then washed with aq. NaHCO$_3$, dried with MgSO$_4$, and concentrated. The crude residue was purified by column chromatography (silica gel, 25 to 100% EtOAc in hexanes) to give compound 91 (420 mg, 88% yield) as a solid. m/z=419 (M+1).

Compound 92:

Compound 91 (420 mg, 1 mmol) was taken up in THF (5 mL), and 3N HCl (aq, 3 mL) was added. The mixture was stirred overnight at room temperature, then concentrated. The residue was neutralized with saturated aq. NaHCO$_3$, and extracted with ethyl acetate. The organic extract was washed with water, dried with MgSO$_4$, and concentrated to give compound 92 (385 mg, quantitative yield) as a solid. m/z=375 (M+1).

Compound 93:

Compound 92 (385 mg, 1 mmol) was taken up in ethyl formate (15 mL, 187.5 mmol). NaOMe (30 wt. % in methanol, 0.75 g, 4 mmol) was added. The mixture was stirred overnight at room temperature, neutralized with aq. KH$_2$PO$_4$, and extracted with ethyl acetate. The organic extract was dried with MgSO$_4$ and concentrated to give compound 93 (410 mg, quantitative yield) as a solid. m/z=403 (M+1).

Compound 94:

Compound 93 (410 mg, 1 mmol) was dissolved in EtOH. Hydroxylamine hydrochloride (140 mg, 2 mmol) was added. The reaction mixture was stirred overnight at 50° C., cooled to room temperature, and concentrated. The residue was taken up in ethyl acetate, washed with aq. NaHCO$_3$, dried with MgSO$_4$, and concentrated to give compound 94 (400 mg, quantitative yield) as an oil. m/z=400 (M+1).

Compound 95:

Compound 94 (400 mg, 1 mmol) was dissolved in THF (5 mL), and NaOMe (30 wt. % in methanol, 0.75 g, 4 mmol) was added. The reaction mixture was stirred at room temperature overnight, neutralized by addition of saturated KH$_2$PO$_4$, and extracted with ethyl acetate. The organic extract was washed with brine, dried with MgSO$_4$, and concentrated to give compound 95 (400 mg, quantitative yield) as a solid. m/z=400 (M+1).

Compound T17:

Compound 95 (400 mg, 1 mmol) was dissolved in dry DMF (4 mL), and the solution was cooled to 0° C. Br$_2$ (180 mg in 1 mL of dichloromethane, 1.1 eq) was added, and the reaction stirred at 0° C. for 2 h. Pyridine (2 mL, 26 mmol) was added, and the reaction was allowed to warm to room temperature. The reaction mixture was stirred at 50° C. for 16 hours, then concentrated. The crude residue was purified by column chromatography (silica gel, 50 to 100% EtOAc in hexanes) to give compound T17 (185 mg, 46% yield from 91) as a foam. m/z=398 (M+1); $^1$H NMR (400 MHz, CDCl$_3$) δ 8.65 (s, 1H), 7.46 (m, 3H), 7.30 (m, 4H), 3.91 (s, 3H), 2.58 (qd, 1H, J=6.85, 13.5 Hz), 2.51 (m, 2H), 2.13 (dt, 1H, J=2.2, 12.9 Hz), 2.09 (m, 1H), 1.82 (m, 1H), 1.50 (s, 3H), 1.31 (d, 3H, J=6.8 Hz).

Compound T18:

Compound T15 (75 mg, 0.18 mmol) was dissolved in dichloromethane (5 mL) at 0° C. Oxalyl chloride (120 mg, 0.94 mmol) and DMF (1 drop) were added, and the solution was stirred for 1 h. After evaporation of the solvent, the crude carbonyl chloride was obtained. The crude carbonyl chloride in dichloromethane (2 mL) was added to a solution of $MeNH_2$ (30 wt. % in water, 0.3 g, 2.8 mmol) in THF (5 mL) at 0° C., then stirred at room temperature for 16 h. The reaction mixture was concentrated, diluted with saturated $NaHCO_3$ and extracted with EtOAc (2×65 mL). Combined organic extracts were dried with $MgSO_4$, concentrated, and purified by column chromatography (silica gel, 0 to 10% MeOH in EtOAc) to give compound T18 (25 mg, 32% yield) as a foam. m/z=417 (M+H); $^1$H NMR (400 MHz, $CDCl_3$) δ 8.54 (s, 1H), 7.41 (t, 1H, J=7.7 Hz), 7.30 (m, 1H), 7.04 (m, 2H), 5.34 (br s, 1H), 3.04 (t, 2H, J=7.5 Hz), 2.79 (d, 3H, J=4.9 Hz), 2.49 (t, 2H, J=7.5 Hz), 2.47 (m, 3H), 2.25 (s, 3H), 2.10 (dt, 1H, J=2.3, 12.3 Hz), 2.02 (m, 1H), 1.75 (m, 1H), 1.44 (s, 3H), 1.28 (d, 3H, J=6.9 Hz).

Compound T19:

Compound T15 (100 mg, 0.24 mmol) was dissolved in dichloromethane (5 mL) at 0° C. Oxalyl chloride (150 mg, 1.18 mmol) and DMF (1 drop) were added, and the solution was stirred for 1 h. After evaporation of the solvent, the crude carbonyl chloride was obtained. The crude carbonyl chloride in dichloromethane (2 mL) was added to a solution of $Me_2NH$ (2M, 1 mL, 2 mmol) in dichloromethane (5 mL) at 0° C., then stirred at room temperature for 16 h. The reaction mixture was concentrated, diluted with saturated $NaHCO_3$, and extracted with EtOAc (2×65 mL). Combined organic extracts were dried with $MgSO_4$, concentrated, and purified by column chromatography (silica gel, 0 to 10% MeOH in EtOAc) to give compound T19 (40 mg, 38% yield) as a foam. m/z=431 (M+H); $^1$H NMR (400 MHz, $CDCl_3$) δ 8.54 (s, 1H), 7.40 (t, 1H, J=7.7 Hz), 7.31 (d, 1H, J=7.8 Hz), 7.05 (m, 2H), 3.04 (t, 2H, J=7.6 Hz), 2.97 (s, 3H), 2.95 (s, 3H), 2.64 (t, 2H, J 7.6 Hz), 2.54 (qd, 1H, J=6.8, 13.5 Hz), 2.40 (m, 2H), 2.25 (s, 3H), 2.09 (dt, 1H, J 2.3, 13.0 Hz), 2.01 (m, 1H), 1.74 (ddd, 1H, J=6.7, 12.9, 18.0 Hz), 1.44 (s, 3H), 1.27 (d, 3H, J=6.7 Hz).

Compound T20:

Compound T15 (75 mg, 0.18 mmol) was dissolved in dichloromethane (5 mL) at 0° C. Oxalyl chloride (120 mg, 5 eq) and DMF (1 drop) were added, and the solution was stirred for 1 h. After evaporation of the solvent, the crude carbonyl chloride was obtained. The crude carbonyl chloride in dichloromethane (2 mL) was added to a solution of $NH_4OH$ (30 wt. %, 0.2 g, 3 mmol) in THF (5 mL) at 0° C., then stirred at room temperature for 16 h. The reaction mixture was concentrated, diluted with saturated $NaHCO_3$, and extracted with EtOAc (2×65 mL). Combined organic extracts were dried with $MgSO_4$, concentrated, and purified by column chromatography (silica gel, 0 to 10% MeOH in EtOAc) to give compound T20 (10 mg, 10% yield) as a foam. m/z=403 (M+H); $^1$H NMR (400 MHz, $CDCl_3$) δ 8.54 (s, 1H), 7.42 (t, 1H, J=7.7 Hz), 7.31 (d, 1H, J=7.9 Hz), 7.06 (m, 2H), 5.29 (br s, 2H), 3.05 (t, J=7.5 Hz, 2H), 2.57 (t, 2H, J=7.6 Hz), 2.43 (m, 3H), 2.26 (s, 3H), 2.06 (m, 2H), 1.74 (m, 1H), 1.44 (s, 3H), 1.28 (d, 3H, J=6.8 Hz).

Compound 96:

Compound 8 (1.0 g, 3.96 mmol) was mixed in EtOH (15 mL) along with ammonium acetate (3.0 g, 39 mmol) and acetaldehyde (350 mg, 7.95 mmol), and the mixture was stirred for 16 h. The mixture was concentrated, quenched with saturated $NaHCO_3$, and extracted with EtOAc (2×100 mL). The combined organic extracts were dried over $MgSO_4$ and concentrated. The crude product was purified by column chromatography (silica gel, 0-10% MeOH/EtOAc) to give compound 96 (0.85 g, 77% yield) as an oil. m/z=277 (M+1).

Compound 97:

Compound 96 (330 mg, 1.2 mmol) was mixed with cesium carbonate (1.5 g, 4.6 mmol) in acetonitrile (35 mL). 1-Bromo-3-methoxypropane (300 mg, 1.96 mmol) was added and the mixture was heated at 85° C. for 16 h. The mixture was cooled and filtered. The filtrate was concentrated and purification by flash chromatography (silica gel, 0-10% MeOH/EtOAc) to give compound 97 (385 mg, 92% yield) as an oil. m/z=349.21 (M+1).

Compound 98:

Compound 97 (385 mg, 1.10 mmol) was taken up in THF (5 mL) and 3N HCl (5 mL) was added. The mixture was stirred for 16 h, then concentrated, diluted with saturated $NaHCO_3$ (20 mL) and extracted with EtOAc (2×65 mL). The combined organic extracts were dried over $MgSO_4$ and concentrated to give compound 98 (290 mg, 79% yield) as an oil. m/z=305 (M+1).

Compound 99:

Compound 98 (290 mg, 0.95 mmol) was taken up in ethyl formate (15 mL) and NaOMe (30 wt. % in MeOH, 685 mg, 3.80 mmol) was added dropwise. After stirring at room temperature overnight, the reaction mixture was concentrated, quenched with saturated aq. $KH_2PO_4$, and extracted with EtOAc. The combined organic extracts were dried over $MgSO_4$ and concentrated to give compound 99 (250 mg, 79% yield) as an oil. m/z=333 (M+1).

Compound 100:

Compound 99 (250 mg, 0.75 mmol) was taken up in EtOH (50 mL). Hydroxylamine hydrochloride (110 mg, 1.58 mmol) was added, and the mixture was heated at 50° C. for 16 h. The solution was cooled and concentrated. Saturated $NaHCO_3$ was added, and the mixture was extracted with EtOAc (2×65 mL). The combined organic extracts were dried over $MgSO_4$ and concentrated to give compound 100 (215 mg, 87% yield) as a foam. m/z=330 (M+1).

Compound 101:

Compound 100 (215 mg, 0.65 mmol) was taken up in THF (2 mL) and NaOMe (470 mg, 30 wt. % in MeOH) was added. The solution was stirred at room temperature for 16 h and then concentrated. Saturated aq. $KH_2PO_4$ was added, and the mixture was extracted with EtOAc (2×65 mL). The combined organic extracts were dried over $MgSO_4$ and concentrated to give compound 101 (200 mg, 93% yield) as a foam. m/z=330 (M+1).

Compound T21:

Compound 101 (200 mg, 0.61 mmol) was taken up in DMF (4 mL) and cooled in an ice bath. A solution of bromine (110 mg, 0.69 mmol) in dichloromethane (1 mL) was added and the solution was stirred 2 h at 0° C. Pyridine (2 mL) was added and the solution was heated at 50° C. for 12 h. The solution was cooled and concentrated. Dichloromethane (2 mL) was added followed by saturated aq. $NaHCO_3$ (0.5 mL) and the mixture was stirred for 30 min. The crude product was purified by column chromatography (silica gel, 0 to 2.5 to 5% MeOH/EtOAc) to give compound T21 (30 mg, 15% yield) as a light orange gum. m/z=328 (M+1); $^1$H NMR (400 MHz, $CDCl_3$) δ 8.49 (s, 1H), 3.83 (m, 2H), 3.34 (s, 3H), 3.33 (m, 2H), 2.57 (m, 3H), 2.38 (s, 3H), 2.05 (m, 2H), 1.85 (m, 3H), 1.37 (s, 3H), 1.29 (d, 3H, J 6.7 Hz).

Compound 102:

To a solution of compound 8 (336 mg, 1.33 mmol) in benzene (16 mL) was added 3-pyrimidin-5-ylaniline (250 mg, 1.47 mmol), followed by p-toluenesulfonic acid monohydrate (51 mg, 0.27 mmol). The reaction mixture was stirred at 80° C. for 3 days under $N_2$. The reaction mixture was concentrated, dissolved in dichloromethane (100 mL) and then washed with saturated $NaHCO_3$ solution (2×25 mL). The organic extract was washed with brine (25 mL), dried ($Na_2SO_4$), filtered, and concentrated to give a residue. Purification by flash chromatography (silica gel, 1 to 1.25% MeOH in dichloromethane) afforded compound 102 (419 mg, 78% yield) as a yellow foamy solid. m/z=406 (M+1).

Compound 103:

To a solution of 102 (412 mg, 1.02 mmol) in a mixture of ethanol (3 mL) and tetrahydrofuran (4 mL) was added ammonium acetate (786 mg, 10.20 mmol), followed by acetaldehyde (180 mg, 4.08 mmol). The reaction mixture was stirred in a closed cap vial at room temperature for 5 days. Additional acetaldehyde was added as needed to drive the reaction to completion. The reaction mixture was concentrated, diluted with saturated $NaHCO_3$ solution (50 mL) and then extracted with ethyl acetate (3×100 mL). The organic extracts were combined, dried ($Na_2SO_4$), filtered and then concentrated to give a red oil. Purification by flash chromatography (silica gel, 1 to 5% MeOH in dichloromethane) afforded compound 103 (249 mg, 57% yield) as a light yellow tacky solid. m/z=431 (M+1).

Compound 104:

To a solution of compound 103 (249 mg, 0.578 mmol) in tetrahydrofuran (5 mL) was added 3 M aq. HCl (1.0 mL, 3.0 mmol). The reaction mixture was stirred at room temperature for 18 h under $N_2$. The reaction mixture was concentrated, diluted with saturated $NaHCO_3$ solution (25 mL) and then extracted with ethyl acetate (4×100 mL). The organic extracts were combined, washed with brine (50 mL), dried ($Na_2SO_4$), filtered, and concentrated to give compound 104 (222 mg, 99% yield) as a yellow solid, which was used in the next step without further purification. m/z=387 (M+1, 100%).

Compound 105:

To a cold (5° C.) solution of compound 104 (222 mg, 0.574 mmol) in a mixture of ethyl formate (5 mL) and tetrahydrofuran (2 mL) was added sodium methoxide (5.4 M solution in MeOH, 1.06 mL, 5.74 mmol). The reaction mixture was stirred for 3 days under $N_2$ at room temperature, then quenched with saturated $KH_2PO_4$ (10 mL), diluted with water (25 mL), and extracted with ethyl acetate (3×50 mL). The organic extracts were combined, washed with brine (50 mL), dried ($Na_2SO_4$), filtered, and concentrated to give compound 105 (234 mg, 98% yield) as a yellow foamy solid, which was used in the next step without further purification. m/z=415 (M+1).

Compound 106:

To a solution of compound 105 (234 mg, 0.565 mmol) in ethanol (6 mL) was added hydroxylamine hydrochloride (78 mg, 1.13 mmol). The reaction mixture was stirred at 50° C. under $N_2$ for 18 h. The reaction mixture was concentrated, diluted with saturated $NaHCO_3$ solution (25 mL) and then extracted with ethyl acetate (3×50 mL). The organic extracts were combined, washed with brine (50 mL), dried ($Na_2SO_4$), filtered and then concentrated to give a residue. Purification by flash chromatography (silica gel, 2 to 3% MeOH in dichloromethane) afforded compound 106 (152 mg, 65% yield) as a light yellow solid. m/z=412 (M+1).

Compound 107:

To a solution of compound 106 (152 mg, 0.369 mmol) in a mixture of tetrahydrofuran (6 mL) and methanol (1.2 mL) was added sodium methoxide (5.4 M solution in MeOH, 0.68 mL, 3.69 mmol). After stirring at room temperature under $N_2$ for 18 h, the reaction mixture was concentrated, diluted with saturated $KH_2PO_4$ solution (20 mL) and then extracted with ethyl acetate (3×50 mL). The organic extracts were combined, washed with brine (50 mL), dried ($Na_2SO_4$), filtered, and concentrated to afford compound 107 (152 mg, quantitative yield) as a yellow solid. m/z=412 (M+1).

Compound T22:

To a solution of compound 107 (150 mg, 0.36 mmol) in anhydrous N,N-dimethylformamide (4 mL) was added 1,3-dibromo-5,5-dimethylhydantoin (63 mg, 0.22 mmol). The reaction mixture was stirred at 0° C. for 1 h. Pyridine (0.40 mL) was added and then the reaction mixture was stirred at 60° C. for 3 h. The reaction mixture was diluted with saturated $NaHCO_3$ (20 mL) and then extracted with ethyl acetate (3×50 mL). The organic extracts were combined, washed with brine (50 mL), dried ($Na_2SO_4$), filtered, and concentrated to afford a residue. Purification by flash chromatography (silica gel, 1 to 2% MeOH in dichloromethane) afforded compound T22 (79 mg, 54% yield) as an off-white solid. m/z=410 (M+1); $^1$H NMR (400 MHz, $CDCl_3$) δ 9.27 (s, 1H), 8.98 (s, 2H), 8.55 (s, 1H), 7.69 (m, 2H), 7.44 (s, 1H), 7.34 (m, 1H), 2.49 (m, 3H), 2.33 (s, 3H), 2.10 (m, 2H), 1.77 (m, 1H), 1.46 (s, 3H), 1.29 (d, 3H, J=7.0 Hz).

Compound 108:

Compound 9 (3.7 g, 11.3 mmol) was dissolved in EtOH (20 mL). Formaldehyde (37 wt. % in water, 1.5 g, 16.8 mmol) and ammonium acetate (9 g, 116 mmol) were added. The reaction mixture was stirred for 16 h at room temperature. Formaldehyde (1.5 g) was added and stirred for another 2 days. The reaction mixture was concentrated. The residue was taken up in ethyl acetate, washed with aq. $NaHCO_3$, dried with $MgSO_4$, and concentrated. The crude residue was purified by column chromatography (silica gel, 0 to 10% MeOH in EtOAc) to give compound 108 (3.7 g, 96% yield) as a foam. m/z=339 (M+1).

Compound 109:

Compound 108 (430 mg, 1.27 mmol) was dissolved in dry acetonitrile (10 mL), and the solution was cooled to 0° C. NBS (265 mg, 1.5 mmol) was added, and the reaction was stirred at 0° C. for 1 h. The reaction was allowed to warm to room temperature and stirred for 16 h. After concentration, the crude residue was purified by column chromatography (silica gel, 0 to 35% EtOAc in hexane) to give compound 109 (510 mg, 96% yield) as an off-white solid. m/z=417, 419 (1:1, M+1).

Compound 110:

Compound 109 (160 mg, 0.38 mmol) was taken up in THF (5 mL), and 3N aq. HCl (3 mL) was added. The mixture was stirred overnight at room temperature, then concentrated. The residue was neutralized with saturated aq. $NaHCO_3$, and extracted with ethyl acetate. The organic extract was washed with water, then dried with $MgSO_4$, and concentrated to give compound 110 (140 mg, quantitative yield) as a foam. m/z=373, 375 (M+1).

Compound 111:

Compound 110 (140 mg, 0.38 mmol) was taken up in ethyl formate (10 mL, 125 mmol), and NaOMe (30 wt. % in methanol, 0.25 g, 1.5 mmol) was added. The mixture was stirred overnight at room temperature, then neutralized with aq. $KH_2PO_4$, and extracted with ethyl acetate. The organic extract was dried with $MgSO_4$ and concentrated to give compound 111 (100 mg, 66% yield) as a foam. m/z=401, 403 (M+1).

Compound 112:

Compound 111 (100 mg, 0.25 mmol) was dissolved in EtOH (15 mL), and hydroxylamine hydrochloride (35 mg, 0.5 mmol) was added. The reaction mixture was stirred overnight at 50° C., then cooled to room temperature, and concentrated. The residue was taken up in ethyl acetate, washed with aq. NaHCO$_3$, dried with MgSO$_4$, and concentrated to give compound 112 (100 mg) as a foam. m/z=398, 400 (M+1).

Compound 113:

Compound 112 (100 mg, 0.25 mmol) was dissolved in THF (5 mL), and NaOMe (30 wt. % in methanol, 0.18 g, 1 mmol) was added. The reaction mixture was stirred at room temperature overnight, then neutralized by addition of saturated KH$_2$PO$_4$, and extracted with ethyl acetate. The organic extract was washed with brine, dried with MgSO$_4$, and concentrated to give compound 113 (100 mg) as a foam. m/z=398, 400 (M+1).

Compound T23:

Compound 113 (100 mg, 0.25 mmol) was dissolved in dry DMF (2 mL), and the solution was cooled to 0° C. Bromine (45 mg in 1 mL of dichloromethane, 0.28 mmol) was added, and the reaction stirred at 0° C. for 2 h. Pyridine (2 mL, 26 mmol) was added, and the reaction was allowed to warm to room temperature. The reaction mixture was stirred at 50° C. for 16 h. After concentration, the crude residue was purified by column chromatography (silica gel, 5 to 35% EtOAc in hexanes) to give compound T23 (33 mg, 33% yield from 111) as a foam. m/z=396, 398 (M+1); $^1$H NMR (400 MHz, CDCl$_3$) δ 8.50 (s, 1H), 7.52 (m, 3H), 7.25 (m, 2H), 2.55 (qd, 1H, J=6.8, 13.5 Hz), 2.44 (m, 2H), 2.11 (dt, 1H, J=2.3, 12.8 Hz), 2.03 (m, 1H), 1.76 (m, 1H), 1.46 (s, 3H), 1.28 (d, 3H, J=6.8 Hz).

Compound 114:

Compound 109 (350 mg, 0.81 mmol) was taken up in dioxane/DMF (4:1, 10 mL). K$_2$CO$_3$ (370 mg, 2.53 mmol), Pd(dppf)Cl$_2$ (60 mg, 0.08 mmol) and pyridin-4-ylboronic acid (200 mg, 1.6 mmol) were added. The reaction mixture was bubbled with N$_2$ for 10 min. After stirring at 100° C. for 16 h, the reaction mixture was filtered, and concentrated. The crude residue was purified by column chromatography (silica gel, 0 to 10% MeOH in EtOAc) to give compound 114 (320 mg, 98% yield) as a solid. m/z=416 (M+1).

Compound 115:

Compound 114 (320 mg, 0.8 mmol) was taken up in THF (7 mL), and 3N HCl (aq, 3 mL) was added. After stirring overnight at room temperature, the reaction mixture was concentrated. The residue was neutralized with saturated aq. NaHCO$_3$, and extracted with ethyl acetate. The organic extract was washed with water, dried with MgSO$_4$, and concentrated to give compound 115 (200 mg, 70% yield) as a foam. m/z=372 (M+1).

Compound 116:

Compound 115 (200 mg, 0.54 mmol) was taken up in ethyl formate (15 mL, 187.5 mmol), and NaOMe (30 wt. % in methanol, 0.4 g, 2.2 mmol) was added. The mixture was stirred overnight at room temperature, then neutralized with aq. KH$_2$PO$_4$, and extracted with ethyl acetate. The organic extract was dried with MgSO$_4$ and concentrated to give compound 116 (205 mg, 94% yield) as a solid. m/z=400 (M+1).

Compound 117:

Compound 116 (205 mg, 0.5 mmol) was dissolved in EtOH (15 mL), and hydroxylamine hydrochloride (70 mg, 1 mmol) was added. The reaction mixture was stirred overnight at 50° C. After cooling to room temperature, the reaction mixture was concentrated. The residue was taken up in ethyl acetate, then washed with aq. NaHCO$_3$, dried with MgSO$_4$, and concentrated to give compound 117 (200 mg) as a foam. m/z=397 (M+1).

Compound 118:

Compound 117 (200 mg, 0.5 mmol) was dissolved in THF (5 mL), and NaOMe (30 wt. % in methanol, 0.36 g, 2 mmol) was added. The reaction mixture was stirred at room temperature overnight, then neutralized by addition of saturated KH$_2$PO$_4$, and extracted with ethyl acetate. The organic extract was washed with brine, dried with MgSO$_4$, and concentrated to give compound 118 (200 mg) as an oil. m/z=397 (M+1).

Compound T24:

Compound 118 (200 mg, 0.5 mmol) was dissolved in dry DMF (4 mL), and the solution was cooled to 0° C. Bromine (90 mg in 1 mL of dichloromethane, 0.56 mmol) was added, and the reaction stirred at 0° C. for 2 h. Pyridine (2 mL, 26 mmol) was added, and the reaction was allowed to warm to room temperature. The reaction mixture was stirred at 50° C. for 16 h. After concentration, the crude residue was purified by column chromatography (silica gel, 0 to 10% MeOH in EtOAc) to give compound T24 (85 mg, 43% yield from 116) as an off-white solid. m/z=395 (M+1); $^1$H NMR (400 MHz, CDCl$_3$) δ 8.64 (s, 1H), 8.46 (m, 2H), 7.51 (m, 3H), 7.22 (m, 4H), 2.59 (qd, 1H, J=6.8, 13.5 Hz), 2.50 (dd, 2H, J=4.0, 8.7 Hz), 2.15 (dt, 1H, J=2.3, 12.7 Hz), 2.09 (m, 1H), 1.82 (tt, 1H, J=8.9, 13.4 Hz), 1.55 (s, 3H), 1.30 (d, 3H, J=6.8 Hz).

Compound 119:

To a solution of compound 48 (350 mg, 1.05 mmol) in a mixture of tetrahydrofuran (3 mL) and ethanol (4 mL) was added ammonium acetate (809 mg, 10.50 mmol), followed by o-tolualdehyde (1.010 g, 8.40 mmol). The reaction mixture was stirred at 80° C. for 18 h. The reaction mixture was concentrated, diluted with saturated aq. NaHCO$_3$ solution (25 mL) and then extracted with ethyl acetate (3×50 mL). The organic extracts were combined, washed with brine (50 mL), dried (Na$_2$SO$_4$), filtered, and concentrated to give a red oil. Purification by flash chromatography (silica gel, 2 to 17% EtOAc in dichloromethane) afforded compound 119 (377 mg, 83% yield) as a yellow tacky solid. m/z=435 (M+1).

Compound 120:

To a solution of compound 119 (255 mg, 0.587 mmol) in tetrahydrofuran (5 mL) was added 3M aq. HCl (1.0 mL, 3 mmol). The reaction mixture was stirred at room temperature for 3.5 h under N$_2$, then diluted with saturated aq. NaHCO$_3$ solution (25 mL), and extracted with ethyl acetate (3×50 mL). The organic extracts were combined, washed with brine (50 mL), dried (Na$_2$SO$_4$), filtered, and concentrated to give compound 120 (250 mg, quantitative) as a yellow-green tacky solid, which was used in the next step without further purification. m/z=391 (M+1).

Compound 121:

To a 0° C. solution of compound 120 (250 mg, 0.640 mmol) in a mixture of ethyl formate (5 mL) and tetrahydrofuran (2 mL) was added sodium methoxide (5.4 M solution in methanol, 1.19 mL, 6.40 mmol). The reaction mixture was stirred for 18 h under N$_2$ at room temperature, then quenched with saturated KH$_2$PO$_4$ (25 mL), and extracted with ethyl acetate (3×50 mL). The organic extracts were combined, washed with brine (50 mL), dried (Na$_2$SO$_4$), filtered, and concentrated to give compound 121 (252 mg, 94% yield) as a yellow-orange foamy solid, which was used in the next step without further purification. m/z=419 (M+1).

Compound 122:

To a solution of compound 121 (252 mg, 0.602 mmol) in ethanol (6 mL) was added hydroxylamine hydrochloride (84 mg, 1.20 mmol). The reaction mixture was stirred at 50° C. under N$_2$ for 18 h, then concentrated, diluted with saturated aq. NaHCO$_3$ solution (25 mL), and extracted with ethyl acetate (3×50 mL). The organic extracts were combined, washed with brine (50 mL), dried (Na$_2$SO$_4$), filtered, and concentrated to give a residue. Purification by flash chromatography (silica gel, 9 to 50% EtOAc in hexanes) afforded compound 122 (105 mg, 42% yield) as an off-white tacky solid. m/z=416 (M+1).

Compound 123:

To a solution of compound 122 (103 mg, 0.248 mmol) in a mixture of tetrahydrofuran (5 mL) and methanol (1 mL) was added sodium methoxide (5.4 M solution in methanol, 0.46 mL, 2.48 mmol). The reaction mixture was stirred at room temperature under $N_2$ for 18 h, then concentrated. The residue was diluted with saturated $KH_2PO_4$ solution (20 mL), and extracted with ethyl acetate (3×50 mL). The organic extracts were combined, washed with brine (50 mL), dried ($Na_2SO_4$), filtered, and concentrated to afford compound 123 (115 mg) as a yellow solid, which was used in the next step without further purification. m/z=416 (M+1).

Compound T25:

To a solution of compound 123 (115 mg, 0.28 mmol) in anhydrous N,N-dimethylformamide (4 mL) was added 1,3-dibromo-5,5-dimethylhydantoin (48 mg, 0.17 mmol). The reaction mixture was stirred at 0° C. for 1 h. Pyridine (0.40 mL) was added and then the reaction mixture was stirred at 60° C. for 2.5 h. The reaction mixture was diluted with saturated aq. $NaHCO_3$ (20 mL), and extracted with ethyl acetate (3×50 mL). The organic extracts were combined, washed with brine (50 mL), dried ($Na_2SO_4$), filtered, and concentrated to afford a residue. Purification by flash chromatography (silica gel, 1 to 25% MeOH in dichloromethane) afforded compound T25 (48 mg, 42% yield from 122) as a yellow solid. m/z=414 (M+1); $^1$H NMR (400 MHz, $CDCl_3$) δ 8.64 (s, 1H), 8.46 (m, 2H), 7.51 (m, 3H), 7.22 (m, 4H), 2.59 (qd, 1H, J=6.8, 13.5 Hz), 2.50 (dd, 2H, J=4.0, 8.7 Hz), 2.15 (dt, 1H, J=2.3, 12.7 Hz), 2.09 (m, 1H), 1.82 (tt, 1H, J=8.9, 13.4 Hz), 1.55 (s, 3H), 1.30 (d, 3H, J=6.8 Hz).

Compound 124:

A mixture of compound 109 (0.50 g, 1.26 mmol), zinc cyanide (0.15 g, 1.28 mmol), tris(dibenzylideneacetone)dipalladium(0) (0.060 g, 0.066 mmol) and 1,1'-bis(diphenylphosphino)ferrocene (0.040 g, 0.072 mmol) in DMF (3 mL) was degassed then microwaved at 180° C. for 5 min. The sample was cooled, diluted with ethyl acetate (3 mL), filtered, concentrated and chromatographed (silica gel, 0 to 35% EtOAc in hexanes) to give compound 124 (0.380 g, 88% yield) as an off-white solid. m/z=364 (M+1).

Compound 125:

A solution of compound 124 (0.55 g, 1.51 mmol) and 1N aq. HCl (15 mL, 15 mmol) in methanol:THF (1:1, 30 mL) was stirred at room temperature under $N_2$ overnight. The sample was concentrated, cooled, basified with 10% $NH_4OH$ solution to pH~9-10, then extracted with $CHCl_3$ (50 mL). The organic extract was washed with brine (50 mL), dried ($MgSO_4$), filtered, and concentrated to give compound 125 (0.66 g) as yellow oil, which was used in the next step without purification. m/z=320 (M+1).

Compound 126:

To a stirring solution at room temperature under $N_2$ of compound 125 (entire amount from above, ≤1.51 mmol) and ethyl formate (13 mL, 161 mmol) in THF (20 mL) was added dropwise sodium methoxide (30 wt. % solution in methanol, 1.42 mL, 7.57 mmol). The sample was stirred overnight at room temperature then concentrated. Saturated aq. $KH_2PO_4$ solution (50 mL) was added and the mixture was extracted with $CHCl_3$ (50 mL). The organic extract was washed with brine (50 mL), dried ($MgSO_4$), filtered and concentrated to give crude compound 126 (0.59 g) as yellow foamy solid, which was used in the next step without purification. m/z=348 (M+1).

Compound 127 and 128:

Crude compound 126 (entire amount from above, ≤1.51 mmol) and hydroxylamine hydrochloride (0.16 g, 2.30 mmol) in ethanol (25 mL) under $N_2$ was heated at 60° C. for 2 h, and then, stirred at room temperature overnight. The sample was concentrated then partitioned between saturated aq. $NaHCO_3$ solution (50 mL) and $CHCl_3$ (50 mL). The organic extract was washed with brine (50 mL), dried ($MgSO_4$), filtered and concentrated to give a mixture compound 127 and 128 (0.63 g) as tan foamy solid, which was used in the next step without purification. m/z=345 (M+1 for 127) and 363 (M+1 for 128).

Compound 129 and 130:

To a stirring solution at room temperature under $N_2$ of compound 127 and 128 (entire amount from above, ≤1.51 mmol) in methanol (30 mL) was added dropwise sodium methoxide (30 wt. % solution in methanol, 1.7 mL, 9.1 mmol). The sample was stirred at room temperature overnight, concentrated then partitioned between saturated aq. $KH_2PO_4$ solution (50 mL) and $CHCl_3$ (50 mL). The organic extract was washed with brine (50 mL), dried ($MgSO_4$), filtered and concentrated to give a mixture compound 129 and 130 (0.57 g) as tan foamy solid, which was used in the next step without purification. m/z=345 (M+1 for 129) and 363 (M+1 for 130).

Compounds T26 and T27:

To a stirring solution at ~0° C. under $N_2$ of compound 127 and 128 (entire amount from above, ≤1.51 mmol) in DMF (6 mL) was added dropwise a solution of 1,3-dibromo-5,5-dimethylhydantoin (0.26 g, 0.91 mmol) in DMF (4 mL). After stirring for 30 min, pyridine (1.5 mL, 18.5 mmol) was added, the ice-bath was removed and the sample was heated at 60° C. under $N_2$ for 4 h. The sample was cooled, concentrated then partitioned between saturated aq. $KH_2PO_4$ solution (50 mL) and $CHCl_3$ (50 mL). The organic extract was washed with brine (50 mL), dried ($MgSO_4$), filtered, and concentrated. The residue was purified by column chromatography (silica gel, 50% EtOAc in hexanes) to give compound T26 (84 mg, 16% yield from 124) as a light yellow foamy solid and compound T27 (69 mg, 13% yield from 124) as a light yellow foamy solid. T26: m/z=343 (M+1); $^1$H NMR (400 MHz, $CDCl_3$) δ 8.47 (s, 1H), 7.58 (m, 3H), 7.35 (m, 2H), 2.60 (m, 3H), 2.14 (m, 2H), 1.81 (m, 1H), 1.47 (s, 3H), 1.31 (d, 3H, J=6.7 Hz). T27: m/z=361 (M+1); $^1$H NMR (400 MHz, $CDCl_3$) δ 8.50 (s, 1H), 7.47 (m, 3H), 7.24 (m, 2H), 7.11 (br s, 1H), 5.28 (br s, 1H), 2.57 (qd, 1H, J=6.8, 13.5 Hz), 2.42 (m, 2H), 2.12 (dt, 1H, J=2.3, 12.7 Hz), 2.07 (m, 1H), 1.77 (tdd, 1H, J=7.4, 10.2, 13.3 Hz), 1.46 (s, 3H), 1.29 (d, 3H, J=6.7 Hz).

Compound T28:

A solution of compound T3 (35.8 mg, 0.108 mmol) and hydrido(dimethylphosphinous acid-kP)[hydrogen bis(dimethylphosphinito-kP)]platinum(II) (12.5 mg, 0.0291 mmol) in ethanol/water (4:1, 1 mL) was heated to 90° C. for 2 h. The crude mixture was concentrated to a solid, and the residue purified by column chromatography (silica gel, 0 to 100% acetone in hexanes) to give compound T28 (19 mg, 50% yield) as a solid: m/z 350 (M+1); $^1$H NMR (400 MHz, $CDCl_3$) δ 9.08 (s, 1H), 8.42 (br s, 1H), 7.47 (m, 3H), 7.20 (dd, 2H, J=1.8, 6.9 Hz), 5.55 (br s, 1H), 2.57 (qd, 1H, J=6.8, 13.6 Hz), 2.44 (ddd, 1H, J=6.4, 11.1, 17.2 Hz), 2.35 (dd, 1H, J=5.5, 16.7 Hz), 2.27 (s, 3H), 2.08 (dt, 1H, J=2.2, 12.8 Hz), 1.99 (m, 1H), 1.74 (m, 1H), 1.43 (s, 3H), 1.27 (d, 3H, J=6.8 Hz).

All of the compounds, compositions, and methods disclosed and claimed herein can be made and executed without undue experimentation in light of the present disclosure.

While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

REFERENCES

The following references to the extent that they provide exemplary procedural or other details supplementary to those set forth herein, are specifically incorporated herein by reference.

U.S. Pat. No. 7,915,402
U.S. Pat. No. 7,943,778
U.S. Pat. No. 8,124,799
U.S. Pat. No. 8,129,429
PCT Application WO 2008/064133
PCT Application WO 2012/083306
PCT Application WO 2013/163344
PCT Application WO 2015/027206
Abraham and Kappas, *Free Radical Biol. Med.*, 39:1-25, 2005.
Ahmad et al., *Cancer Res.*, 68:2920-2926, 2008.
Ahmad et al., *J. Biol. Chem.*, 281:35764-9, 2006.
Araujo et al., *J. Immunol.*, 171(3):1572-1580, 2003.
Bach, *Hum. Immunol.*, 67(6):430-432, 2006.
Chauhan and Chauhan, *Pathophysiology*, 13(3):171-181 2006.
Dickerson et al., *Prog Neuropsychopharmacol Biol. Psychiatry*, Mar. 6, 2007.
Dinkova-Kostova et al., *Proc. Natl. Acad. Sci. USA*, 102 (12):4584-4589, 2005.
Dudhgaonkar et al., *Eur. J. Pain*, 10(7):573-9, 2006.
Favaloro, et al., *J. Med. Chem.*, 45:4801-4805, 2002.
Forstermann, *Biol. Chem.*, 387:1521, 2006.
*Handbook of Pharmaceutical Salts: Properties, and Use*, Stahl and Wermuth Eds.), Verlag Helvetica Chimica Acta, 2002.
Hanson et al., *BMC Medical Genetics*, 6(7), 2005.
Honda et al. *Bioorg. Med. Chem. Lett.*, 12:1027-1030, 2002.
Honda et al., *J. Med. Chem.*, 43:4233-4246, 2000a.
Honda, et al., *J. Med. Chem.*, 43:1866-1877, 2000b.
Honda et al., *Bioorg. Med. Chem. Lett.*, 7:1623-1628, 1997.
Honda et al., *Bioorg. Med. Chem. Lett.*, 9(24):3429-3434, 1999.
Honda et al., *Bioorg. Med. Chem. Lett.*, 8(19):2711-2714, 1998.
Honda et al., *Bioorg. Med. Chem. Lett.*, 16(24):6306-6309, 2006.
Honda et al., *Org. Biomol. Chem.*, 1:4384-4391, 2003.
Honda, et al., *J. Med. Chem.*, 54(6):1762-1778, 2011.
Hong, et al., 2012.
Ishikawa et al., *Circulation*, 104(15):1831-1836, 2001.
Kawakami et al., *Brain Dev.*, 28(4):243-246, 2006.
Kendall-Tackett, *Trauma Violence Abuse*, 8(2):117-126, 2007.
Kruger et al., *J. Pharmacol. Exp. Ther.*, 319(3):1144-1152, 2006.
Lee et al., *Glia.*, 55(7):712-22, 2007.
Lencz et al., *Mol. Psychiatry*, 12(6):572-80, 2007.
Liby et al., *Cancer Res.*, 65(11):4789-4798, 2005.
Liby et al., *Nat. Rev. Cancer*, 7(5):357-356, 2007a.
Liby et al., *Mol. Cancer Ther.*, 6(7):2113-9, 2007b.
Liu et al., *FASEB J.*, 20(2):207-216, 2006.
Lu et al., *J. Clin. Invest.*, 121(10):4015-29, 2011.
Smith, *March's Advanced Organic Chemistry: Reactions, Mechanisms, and Structure*, 7th Ed., Wiley, 2013.
McIver et al., *Pain*, 120(1-2):161-9, 2005.
Morris et al., *J. Mol. Med.*, 80(2):96-104, 2002.
Morse and Choi, *Am. J. Respir. Crit. Care Med.*, 172(6): 660-670, 2005.
Morse and Choi, *Am. J. Respir. Crit. Care Med.*, 27(1):8-16, 2002.
Pall, *Med. Hypoth.*, 69:821-825, 2007.
Pergola et al., 2011.
Place et al., *Clin. Cancer Res.*, 9(7):2798-806, 2003.
Rajakariar et al., *Proc. Natl. Acad. Sci. USA*, 104(52):20979-84, 2007.
Reagan-Shaw et al., *FASEB J.*, 22(3):659-661, 2008
Reisman et al., *Arch. Dermatol. Res.*, 306(5):447-454, 2014.
Ross et al., *Am. J. Clin. Pathol.*, 120(Suppl):553-71, 2003.
Ross et al., *Expert Rev. Mol. Diagn.*, 3(5):573-585, 2003.
Ruster et al., *Scand. J. Rheumatol.*, 34(6):460-3, 2005.
Sacerdoti et al., *Curr Neurovasc Res.* 2(2):103-111, 2005.
Salvemini et al., *J. Clin. Invest.*, 93(5):1940-1947, 1994.
Sarchielli et al., *Cephalalgia*, 26(9):1071-1079, 2006.
Satoh et al., *Proc. Natl. Acad. Sci. USA*, 103(3):768-773, 2006.
Schulz et al., *Antioxid. Redox. Sig.*, 10:115, 2008.
Suh et al., *Cancer Res.*, 58:717-723, 1998.
Suh et al., *Cancer Res.*, 59(2):336-341, 1999.
Szabo et al., *Nature Rev. Drug Disc.*, 6:662-680, 2007.
Takahashi et al., *Cancer Res.*, 57:1233-1237, 1997.
Tamir and Tannebaum, *Biochim. Biophys. Acta*, 1288:F31-F36, 1996.
Xie T et al., *J Biol Chem.* 270(12):6894-6900, 1995.
Zhou et al., *Am. J. Pathol.*, 166(1):27-37, 2005.

What is claimed is:

1. A compound of the formula:

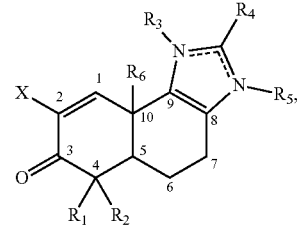

wherein:
X is —CN or —C(O)$R_a$, wherein $R_a$ is —$NH_2$;
$R_1$ and $R_2$ are each independently hydrogen, alkyl$_{(C \leq 12)}$, or substituted alkyl$_{(C \leq 12)}$;
$R_3$ is:
  absent or hydrogen, provided that $R_3$ is absent when the atom to which it is bound forms part of a double bond;
$R_4$ is:
  hydrogen, hydroxy, amino, halo, or cyano; or
  alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups; or
  -alkanediyl$_{(C \leq 6)}$-$Y_1$ wherein $Y_1$ is:

hydroxy, amino, halo, or cyano; or
    acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, arylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups;

$R_5$ is:
    absent, hydrogen, or hydroxy; or
    alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups; or
    -alkanediyl$_{(C \leq 6)}$-$Y_2$,
    -arenediyl$_{(C \leq 8)}$-$Y_3$, or
    -arenediyl$_{(C \leq 8)}$-alkanediyl$_{(C \leq 6)}$-$Y_4$,
        wherein $Y_2$, $Y_3$, and $Y_4$ are each independently:
            hydroxy, amino, halo, or cyano; or
            alkyl$_{(C \leq 12)}$, aryl$_{(C \leq 12)}$, heteroaryl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups;
    provided that $R_5$ is absent when the atom to which it is bound forms part of a double bond; and
$R_6$ is alkyl$_{(C \leq 12)}$ or aryl$_{(C \leq 12)}$, or a substituted version of any of these groups;
or a pharmaceutically acceptable salt thereof.

2. The compound of claim 1, further defined by the formula:

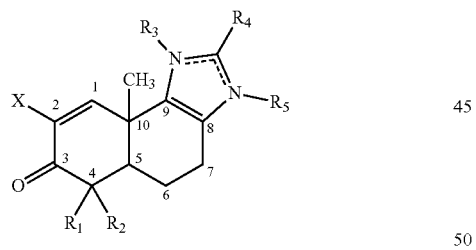

wherein:
    X is —CN or —C(O)$R_a$, wherein $R_a$ is —NH$_2$;
    $R_1$ and $R_2$ are each independently hydrogen, alkyl$_{(C \leq 12)}$, or substituted alkyl$_{(C \leq 12)}$;
    $R_3$ is:
        absent or hydrogen, provided that $R_3$ is absent when the atom to which it is bound forms part of a double bond;
    $R_4$ is:
        hydrogen, hydroxy, amino, halo, or cyano; or
        alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups; or
    -alkanediyl$_{(C \leq 6)}$-$Y_1$, wherein $Y_1$ is:
        hydroxy, amino, halo, or cyano; or
        acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups; and $R_5$ is:
    absent, hydrogen, or hydroxy; or
    alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups; or
    -alkanediyl$_{(C \leq 6)}$-$Y_2$,
    -arenediyl$_{(C \leq 8)}$-$Y_3$, or
    -arenediyl$_{(C \leq 8)}$-alkanediyl$_{(C \leq 6)}$-$Y_4$,
        wherein $Y_2$, $Y_3$, and $Y_4$ are each independently:
            hydroxy, amino, halo, or cyano; or
            alkyl$_{(C \leq 12)}$, aryl$_{(C \leq 12)}$, heteroaryl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, heteroarylamino$_{(C \leq 12)}$, amido$_{(C \leq 12)}$, or a substituted version of any of these groups;
    provided that $R_5$ is absent when the atom to which it is bound forms part of a double bond;
or a pharmaceutically acceptable salt thereof.

3. The compound of claim 2, further defined by the formula:

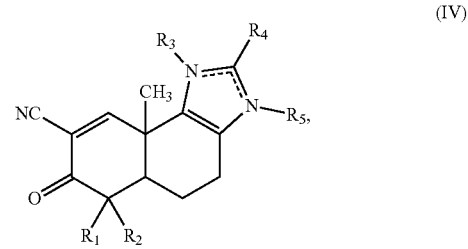

(IV)

wherein:
    $R_1$ and $R_2$ are each independently hydrogen, alkyl$_{(C \leq 12)}$, or substituted alkyl$_{(C \leq 12)}$;
    $R_3$ is:
        absent or hydrogen, provided that $R_3$ is absent when the atom to which it is bound forms part of a double bond;
    $R_4$ is:
        hydrogen, hydroxy, amino, halo, or cyano; or
        alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heterocycloalkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, heteroaryloxy$_{(C \leq 12)}$, acyloxy$_{(C \leq 12)}$, alkylamino$_{(C \leq 12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; or
-alkanediyl$_{(C\leq6)}$-Y$_1$, wherein Y$_1$ is:
hydroxy, amino, halo, or cyano; or
acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; and R$_5$ is:
absent, hydrogen, or hydroxy; or
alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; or
-alkanediyl$_{(C\leq6)}$-Y$_2$,
-arenediyl$_{(C\leq8)}$-Y$_3$, or
-arenediyl$_{(C\leq8)}$-alkanediyl$_{(C\leq6)}$-Y$_4$,
wherein Y$_2$, Y$_3$, and Y$_4$ are each independently:
hydroxy, amino, halo, or cyano; or
alkyl$_{(C\leq12)}$, aryl$_{(C\leq12)}$, heteroaryl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups;
provided that R$_5$ is absent when the atom to which it is bound forms part of a double bond;
or a pharmaceutically acceptable salt thereof.

4. The compound of claim 3, further defined by the formula:

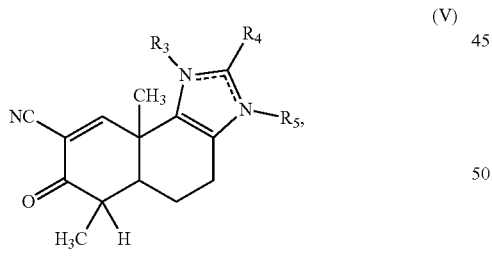

(V)

wherein:
R$_3$ is:
absent or hydrogen, provided that R$_3$ is absent when the atom to which it is bound forms part of a double bond;
R$_4$ is:
hydrogen, hydroxy, amino, halo, or cyano; or
alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; or
-alkanediyl$_{(C\leq6)}$-Y$_1$, wherein Y$_1$ is:
hydroxy, amino, halo, or cyano; or
acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; and R$_5$ is:
absent, hydrogen, or hydroxy; or
alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; or
-alkanediyl$_{(C\leq6)}$-Y$_2$,
-arenediyl$_{(C\leq8)}$-Y$_3$, or
-arenediyl$_{(C\leq8)}$-alkanediyl$_{(C\leq6)}$-Y$_4$,
wherein Y$_2$, Y$_3$, and Y$_4$ are each independently:
hydroxy, amino, halo, or cyano; or
alkyl$_{(C\leq12)}$, aryl$_{(C\leq12)}$, heteroaryl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups;
provided that R$_5$ is absent when the atom to which it is bound forms part of a double bond;
or a pharmaceutically acceptable salt thereof.

5. The compound of claim 4, further defined by the formula:

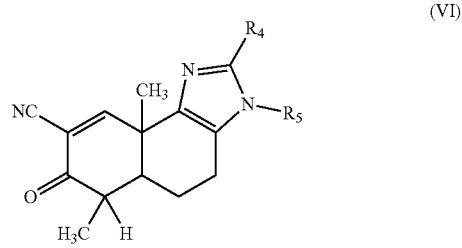

(VI)

wherein:
R$_4$ is:
hydrogen, hydroxy, amino, halo, or cyano; or
alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heterocycloalkyl$_{(C\leq12)}$, acyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, acyloxy$_{(C\leq12)}$, alkylamino$_{(C\leq12)}$, dialkylamino$_{(C\leq12)}$, arylamino$_{(C\leq12)}$, aralkylamino$_{(C\leq12)}$, heteroarylamino$_{(C\leq12)}$, amido$_{(C\leq12)}$, or a substituted version of any of these groups; or -alkanediyl$_{(C\leq 6)}$-Y$_1$, wherein Y$_1$ is:
  hydroxy, amino, halo, or cyano; or
  acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; and R$_5$ is:
  hydrogen or hydroxy; or
  alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups;
  -alkanediyl$_{(C\leq 6)}$-Y$_2$,
  -arenediyl$_{(C\leq 8)}$-Y$_3$, or
  -arenediyl$_{(C\leq 8)}$-alkanediyl$_{(C\leq 6)}$-Y$_4$,
    wherein Y$_2$, Y$_3$, and Y$_4$ are each independently:
    hydroxy, amino, halo, or cyano; or
    alkyl$_{(C\leq 12)}$, aryl$_{(C\leq 12)}$, heteroaryl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups;
or a pharmaceutically acceptable salt thereof.

6. The compound of claim 1, wherein:
  R$_4$ is:
    hydrogen, hydroxy, amino, halo, or cyano; or
    alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups; and
  R$_5$ is:
    hydrogen or hydroxy; or
    alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, alkoxy$_{(C\leq 12)}$, aryloxy$_{(C\leq 12)}$, aralkoxy$_{(C\leq 12)}$, heteroaryloxy$_{(C\leq 12)}$, acyloxy$_{(C\leq 12)}$, alkylamino$_{(C\leq 12)}$, dialkylamino$_{(C\leq 12)}$, arylamino$_{(C\leq 12)}$, aralkylamino$_{(C\leq 12)}$, heteroarylamino$_{(C\leq 12)}$, amido$_{(C\leq 12)}$, or a substituted version of any of these groups.

7. The compound of claim 2, further defined as:

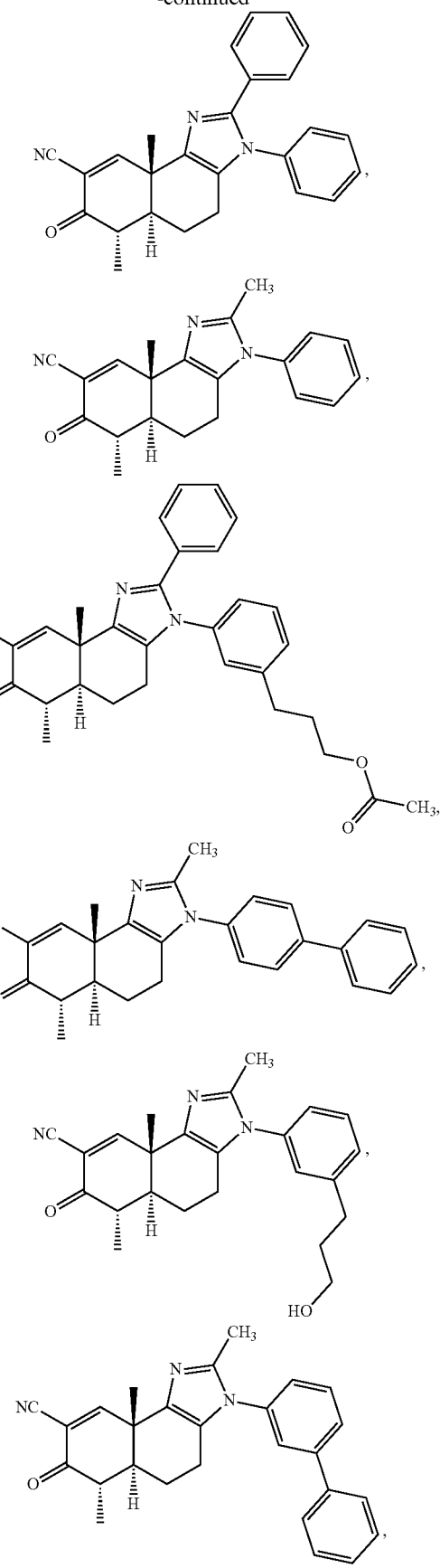

125
-continued
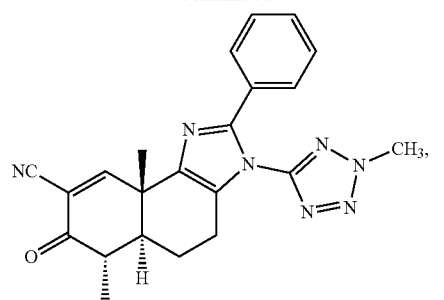
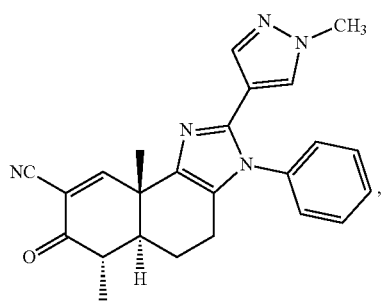
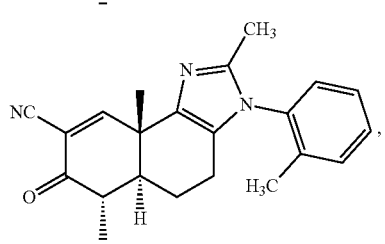
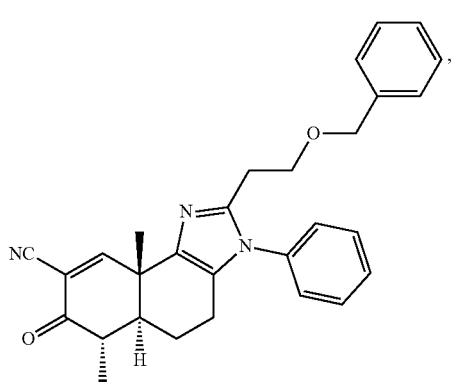
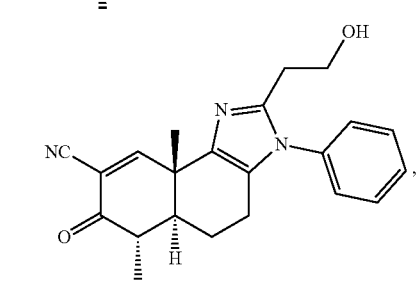
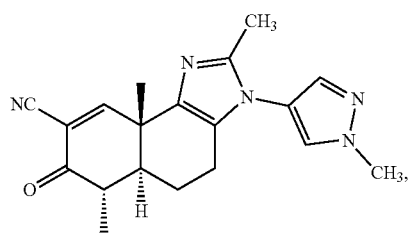
126
-continued
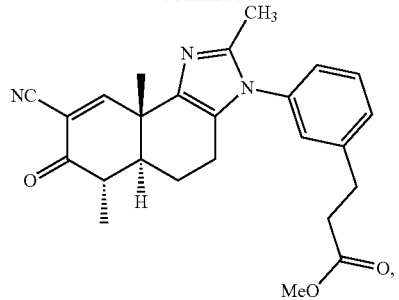
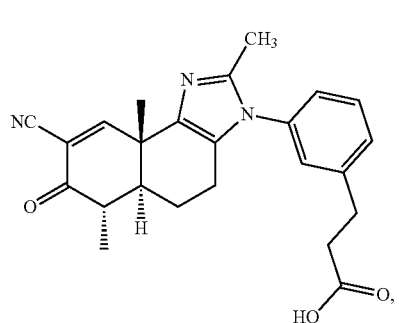
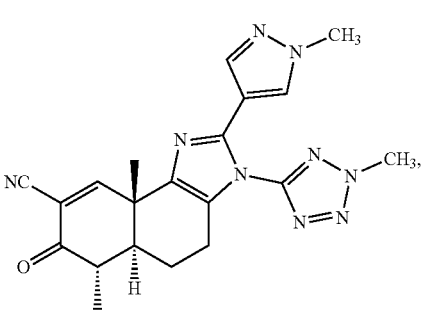
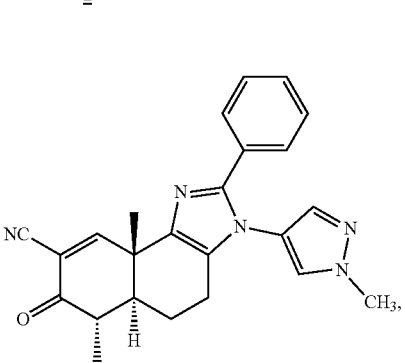
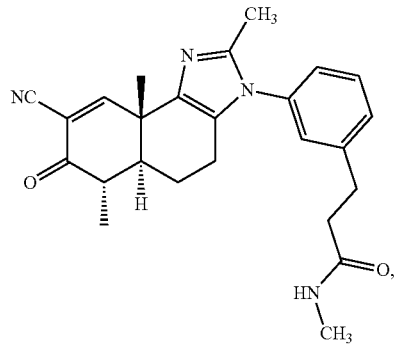

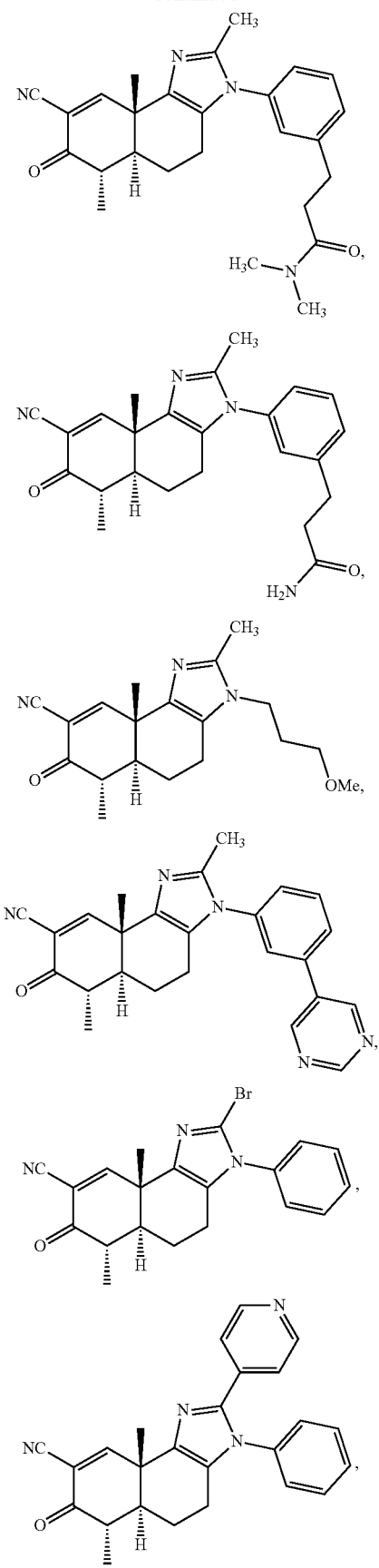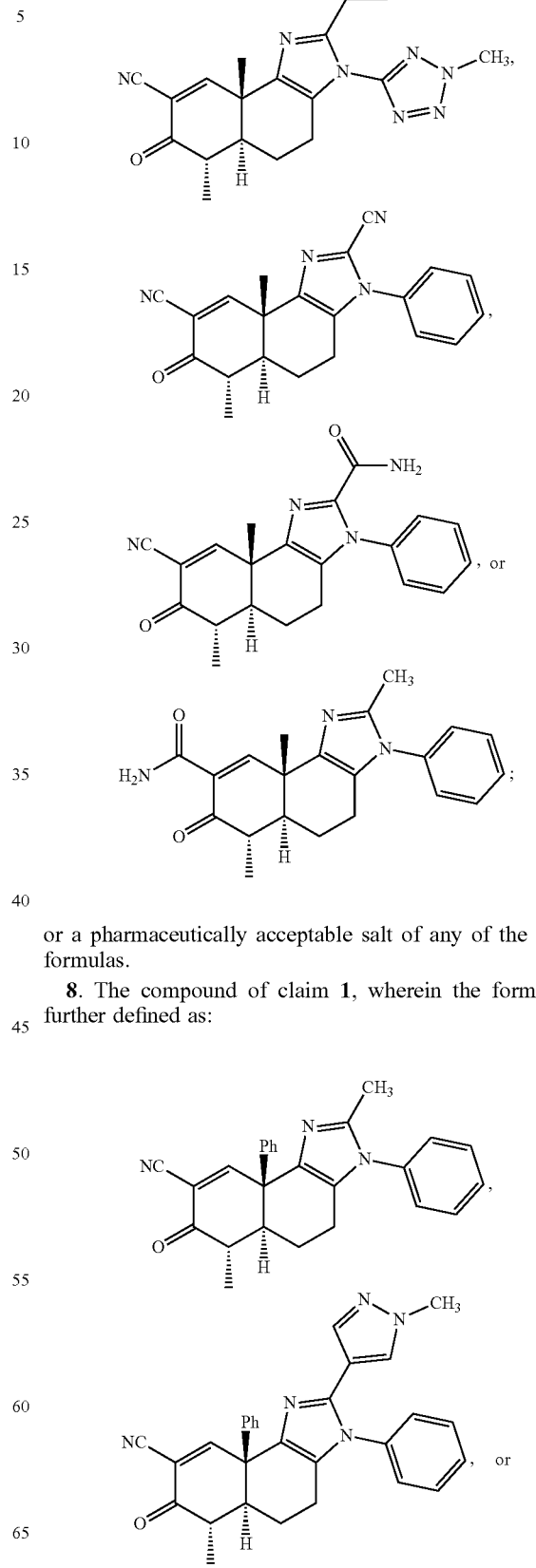
or a pharmaceutically acceptable salt of any of the above formulas.
8. The compound of claim 1, wherein the formula is further defined as:

-continued
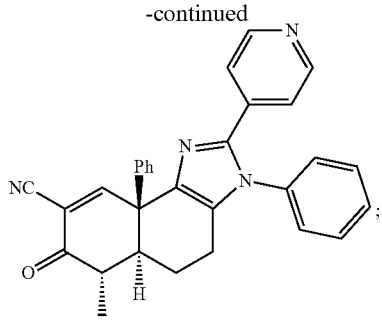
or a pharmaceutically acceptable salt of any of the above formulas.
9. A pharmaceutical composition comprising:
a) a compound of claim 1; and
b) an excipient.
* * * * *

UNITED STATES PATENT AND TRADEMARK OFFICE
CERTIFICATE OF CORRECTION

| | | |
|---|---|---|
| PATENT NO. | : 11,059,792 B2 | Page 1 of 1 |
| APPLICATION NO. | : 15/548909 | |
| DATED | : July 13, 2021 | |
| INVENTOR(S) | : Jiang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 409 days.

Signed and Sealed this
Tenth Day of January, 2023

Katherine Kelly Vidal
*Director of the United States Patent and Trademark Office*